United States Patent
Rathore et al.

(10) Patent No.: US 8,987,554 B2
(45) Date of Patent: *Mar. 24, 2015

(54) COTTON PLANT WITH SEED-SPECIFIC REDUCTION IN GOSSYPOL

(75) Inventors: Keerti S. Rathore, College Station, TX (US); Ganesan Sunilkumar, College Station, TX (US); LeAnne M. Campbell, Cypress, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/109,682

(22) Filed: May 17, 2011

(65) Prior Publication Data

US 2011/0314572 A1 Dec. 22, 2011

Related U.S. Application Data

(63) Continuation of application No. 11/707,760, filed on Feb. 16, 2007, now Pat. No. 7,999,148.

(51) Int. Cl.
| | |
|---|---|
| *C12N 15/113* | (2010.01) |
| *C12N 15/84* | (2006.01) |
| *C12N 5/10* | (2006.01) |
| *A01H 5/00* | (2006.01) |
| *A01H 5/10* | (2006.01) |
| *A01H 4/00* | (2006.01) |
| *C12N 15/82* | (2006.01) |
| *C12N 9/88* | (2006.01) |

(52) U.S. Cl.
CPC ............. *C12N 15/8243* (2013.01); *C12N 9/88* (2013.01)
USPC ........... 800/285; 800/287; 800/314; 800/294; 536/24.5; 435/468; 435/419; 435/427; 435/320.1; 435/469

(58) Field of Classification Search
None
See application file for complete search history.

(56) References Cited

U.S. PATENT DOCUMENTS

| | | | |
|---|---|---|---|
| 7,626,081 B2 | 12/2009 | Rathore et al. | |
| 7,999,148 B2 * | 8/2011 | Rathore et al. | 800/285 |
| 2002/0187538 A1 | 12/2002 | Essenberg et al. | |
| 2003/0154516 A1 | 8/2003 | Rathore et al. | |
| 2004/0133944 A1 | 7/2004 | Hake et al. | |

FOREIGN PATENT DOCUMENTS

| | | |
|---|---|---|
| WO | WO 03/052111 A2 | 6/2003 |
| WO | WO 03052111 A2 * | 6/2003 |

OTHER PUBLICATIONS

Townsend et al. (2005) Plant Phys. 138: 516-528.*
Martin et al. (2003) Phytochem. 62: 31-38.*
Smith et al. (2000) Nature 407: 319-320.*
International Search Report and Written Opinion dated Mar. 19, 2008.
Chen, et al., "Cloning, expression and characterization of (+)-δ-cadinene synthase: a catalyst for cotton phytoalexin biosynthesis," *Arch, Biochem, Biophys*, vol. 324, No. 2., pp. 255-266, 1995.
Davuluri, et al., "Fruit-specific RNAi-mediated suppression of DET1 enhances carotenoid and flavonoid content in tomatoes," *Nature Biotech*, vol. 23, No. 7, pp. 890-895, 2005.
Klahre, et al., "High molecular weight RNAs and small interfering RNAs induce systemic posttranscriptional gene silencing in plants," *PNAS*, vol. 99, No. 18, pp. 11981-11986, 2002.
Martin, et al., "Reduced levels of cadinane sesquiterpenoids in cotton plants expressing antisense (+)-δ-cadinene synthase," *Phytochemistry*, vol. 62, No. 1, pp. 31-38, 2003.
Smith, et al., "Total silencing by intron-spliced hairpin RNAs," Nature, vol. 407, No. 6872, pp. 310-320, 2000.
Thomas, et al., "Size constraints for targeting post-transcriptional gene silencing and for RNA-directed methylation in nicotiana bethamiana using a potato virus x vector," *Plant J*, vol. 25(4), pp. 417-425, 2001.
Townsend, et al., "Antisense suppression of a (+)-δ-cadinene synthase gene in cotton prevents the induction of this defense response gene during bacterial blight infection but not its constitutive expression," *Plant Physiol.*, vol. 138, pp. 516-528, 2005.
Waterhouse, et al., "Virus resistance and gene silencing in plants can be induced by simultaneous expression of sense and antisense RNA," *Proc. Natl. Acad. Sci.* USA, vol. 95, No. 11, pp. 13959-13964, 1998.
Benedict et al., Terpenoid aldehyde formation and lysigenous gland storage sites in cotton: variant with mature glands but suppressed levels of terpenoid aldehydes, Phytochemistry, 65:1351-1359, 2004.
Himber et al., Transitivity-dependent and -independent cell-to-cell movement of RNA silencing, EMBO Journal, 22 (17):4523-4533, 2003.

(Continued)

*Primary Examiner* — David T Fox
*Assistant Examiner* — Steven Bernacki
(74) *Attorney, Agent, or Firm* — Dentons US LLP

(57) ABSTRACT

A method is disclosed for reducing the level of gossypol in cottonseed. The method generally includes selectively inducing RNA gene silencing in the seed of a transgenic cotton plant, to interfere with expression of the δ-cadinene synthase gene or the δ-cadinene-8-hydroxylase gene in the seed of the cotton plant without substantially affecting expression of that gene in the foliage, floral parts, and roots of the plant. The transgenic cotton plant comprises at least one of a δ-cadinene synthase gene trigger sequence and/or a δ-cadinene-8-hydroxylase gene trigger sequence operably linked to one or more a seed-specific promoter gene sequences, and the trigger sequence(s) is/are able to induce RNA gene silencing when expressed in cottonseed of the plant. Also disclosed are expression cassettes, vectors, cells, seeds, and plants containing at least one of a δ-cadinene synthase gene trigger sequence and/or a δ-cadinene-8-hydroxylase gene trigger sequence operably linked to one ore more a seed-specific promoter DNA sequences.

27 Claims, 22 Drawing Sheets

(56) References Cited

OTHER PUBLICATIONS

Magill et al., An antisense-derived cultivar has smaller glands and low gossypol but lacks the expected T-DNA, Beltwide Cotton Conferences, Nashville, TN, Abstract, Jan. 6-10, 2003.

Mlotshvva et al., RNA silencing and the mobile silencing signal, Plant Cell, S289-S301, 2002.

Song et al., Expression of two tissue-specific promoters in transgenic cotton plants, Journal of Cotton Science, 4:217-223, 2000.

Wang and Waterhouse, Application of gene silencing in plants, Current Opinion in Plant Biology, 5:146-150, 2001.

* cited by examiner

```
  1 atgccgagaa cgacctctac accacatccc ttcgattccg attactccga gagcatggat
 61 tcaatgtttc atgcgacgta ttcaacaagt ttaaagacga gcaagggaat ttcaagtcat
121 ccgtgacaag cgatgttcga ggattgttgg aactttacca agcttcctat ttgagggttc
181 atgggaaga tatattggat gaagcaattt ctttcaccac caaccattta agccttgcag
241 tagcatcttt ggactatccg ttatccgaag aggtttcaca tgcttttgaaa caatcaattc
301 gaagaggctt gccaagggtt gaggcaagac actatctttc agtataccaa gatattgagt
361 cccataataa ggttttgttg gagtttttgcta agatcgattt caacatggta caacttttgc
421 ataggaaaga gctaagtgag atttctaggt ggtggaagga tttagacttt caaagaaagt
481 tgccatacgc aagagataga gtggttgaag gctattttg gatctcagga gtgtacttg
541 agccccaata ttctcttggt agaaagatgt tgacaaaagt gatagcaatg gcttctattg
601 taga
```

*FIGURE 2*

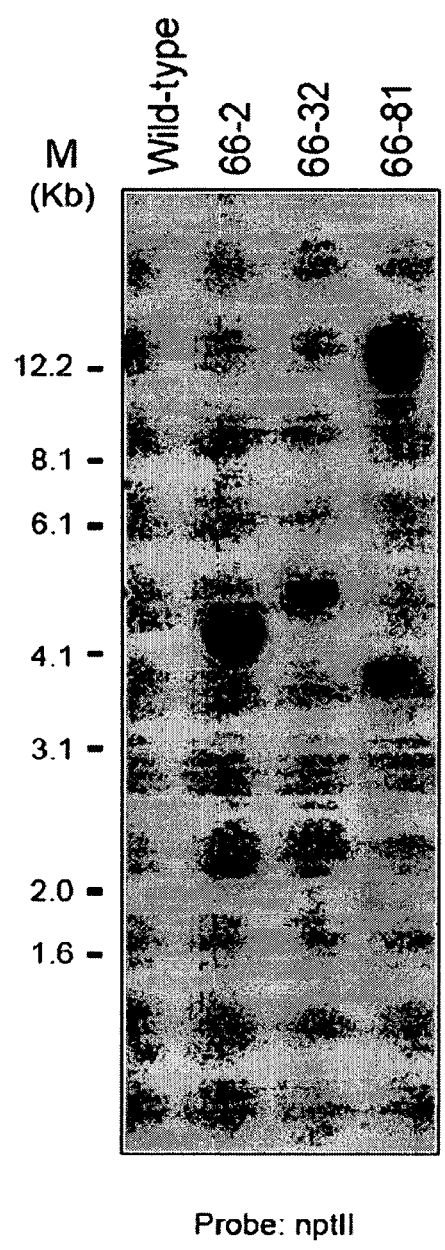 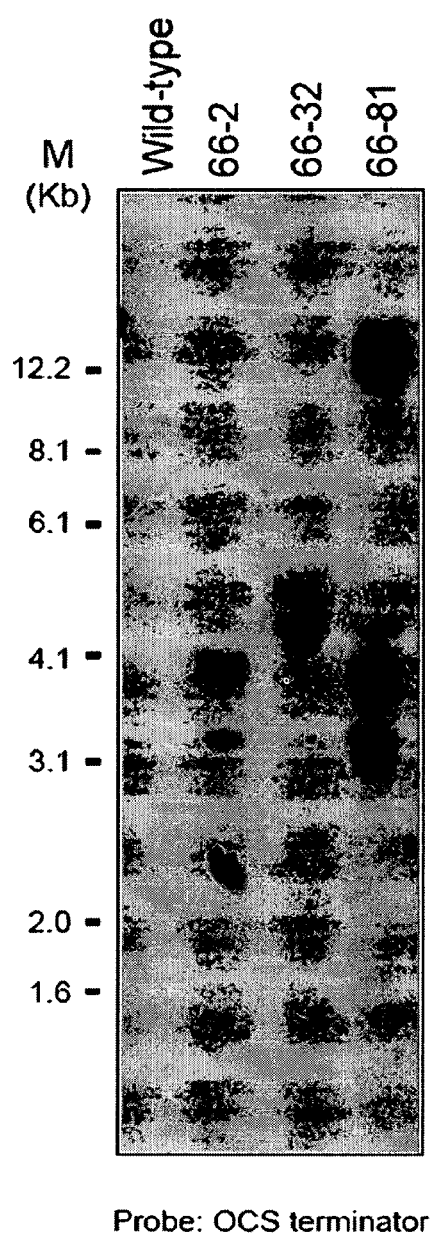
Probe: nptII    Probe: OCS terminator
*FIGURE 7*

```
U23205      TGATCAATC---GAAATGGCTTCACAAGTTTCTCAAATGCCTTCTTCATCA------CCCCTTTCTTCCAATAAGGATGAAATGCGTCCC
AF270425    ---------------------------CAAGTTTCTCAAATGCCTTCTTCATCA------CCCCTTTCTTCCAATAAGGATGAAATGCGTCCC
U88318      TAATCAATC---GAAATGGCTTCACAAGTTTCTCAAATGCCTTCTTCATCA------CCCCTTTCTTCCAATAAGGATGAAATGCGTCCC
Y16432      TGATCAATC---GAAATGGCTTCACAAGTTTCTCAAATGCCTTCTTCATCA------CCCCTTTCTTCCAATAAGGATGAAATCCGTCCC
AF174294    TGATCAATC---GAAATGGCTTCACAAGTTTCTCAAATGCCTTCTTCATCA------CCCCTTTCTTCCAATAAGGATGAAATCCGTCCC
U23206      TGATCAATC---GAAATGGCTTCACAAGTTTCTCAAATGCCTTCTTCATCA------CCCCTTTCTTCCAATAAGGATGAAATGCGTCCC
X95323      TGATCAATC---GAAATGACTTCACAAGTTTCCCAAATGCCTTCTTCATCATCACCCCTTTCTTCCAATAAGGATGAAATGCGTCCC
AY800107    TCATCAACC---GAAATGGCCAAACAAGTTTCTCAACTTCTCTTCTTTCATCA-------CCCCTTACTTCCAACAAAGATGAAATGCGTCTG
X96429      AACACATCCTAGAAAATGGCTTCACAAGCTTCTCAAGTTTCTGCTTCA-------CCCATCCCGCCATTTCATCCGAAAATCGACCC
                   *  *  *  ****** *** ****** *   * ****   *       *** * *   ***  *   **  *

U23205      AAAGCCGATTTTCAGCCTAGCATTTGGGGAGATCTCTTCCTCAACTGTCCCGACAAGAATATTGATGCTGAAACTGAAAAGCGCCAC
AF270425    AAAGCCGATTTTCAGCCTAGCATTTGGGGAGATTCTTCCTCAATTGTCCCGACAAGAATATTGATGCTGAAACTCAAAAACGCCAC
U88318      AAAGCCGATTTTCAGCCTAGCATTTGGGGAGATTCTTCCTCAATTGTCCCGACAAGAATATTGATGCTGAAACTCAAAAACGCCAC
Y16432      AAAGCCGATTTTCAGCCTAGCATTTGGGGAGATTCTTCCTCAATTGTCCCGACAAGAATATTGATGCTGAAACTGAAAAACGCCAC
AF174294    AAAGCCGATTTTCAGCCTAGCATTTGGGGAGATTCTTCCTCAATTGTCCCGACAAGAATATTGATGCTGGAACTGAAAAACGCCAC
U23206      AAAGCCGATTTTCAGCCTAGCATTTGGGGAGATCTCTTCCTCAATTGTCCCGACAAGAATATTGATGCTGAAACTGAAAAACGCCAC
X95323      AAAGCCGATTTTCAGCCTAGCATTTGGGGAGATTCTTCCTCCACAACTGTCCCGACAAGAATATTGATGCTGAAACTGAAAAGCGCCAC
AY800107    AAAGCCGATTATCCGCTAGCATTTGGGGAGATCTCTTCCTTACTTGTCTCGACAATGATATCGATGCTGAAACTGAACAACGCCAC
X96429      AAGGCTGATTTTCATCCCGGTATTTGGGGTGATATGTTCATCATCGTCCTGATACGGATATCGATGCTGCAACTGAATTACAATAT
            ** ** ****  *  *   ********* ***     * *           *     *** ******* **** **     **
```

FIGURE 13

| | |
|---|---|
| U23205 | CAACAATTGAAAGAAGAAGTAAGGAAGATGATTGTGGCACCAATGGCTAATTCAACCCAAAAGTTAGCCTTCATTGATTCAGTCCAA |
| AF270425 | CAACAATTGAAAGAAGAAGTGAGGAAGATGATTGTGGCACCAATGGCTAATTCAACCCAAAAGTTAGCCTTCATTGATTCAGTCCAA |
| U88318 | CAACAATTGAAAGAAGAAGTGAGGAAGATGATTGTGGCACCAATGGCTAATTCAACCCTAAAGTTAGCCTTCATTGATTCAGTCCAG |
| Y16432 | CAACAATTGAAAGAAGAAGTGAGGAAGATGATTGTGGCACCAATGGCTAATTCGACCCAAAAGTTAGCCTTCATTGATTCAGTCCAA |
| AF174294 | CAACAATTGAAAGAAGAAGTGAGGAAGATGATTGTGGCACCGATGGCTAATTCGACCCAAAAGTTAGCCTTCATTGATTCACTCCAA |
| U23206 | CAACAATTGAAAGAAGAAGTGAGGAAGATGATTGTGGCACCAATGGCTAATTCAACCCAAAAGTTAGCCTTCATTGATTCAGTCCAA |
| X95323 | CAACAATTGAAAGAAGAAGTGAGGAAGATGATTGTGGCACCAATGGCTAATTCAACCCAAAAGTTAACCTTCATTGATTCAGTTCAA |
| AY800107 | CAACAGTTGGAAGGAGGAGTGAGGAAGATGATTGTGCCACCAATGGCTAATTCAACCCAAAAGTTAACCTTCATTGATTCGGTCCAA |
| X96429 | GAAGAATTAAAAGCACAAGTGAGGAAGATGATTATGGAACCTGTTGATGATTCAAACCAAAAGTTGCCCTTCATTGATGCTGTTCAA |
| | *  *  ***  ** ********* *** * * ******* *  * ******* * ****** |
| | |
| U23205 | AGGCTGGGTGTGAGTTACCATTTCACTAAGGAGATCGAAGATGAACTAGAGAATATCTACCATAACA---ACAAT---GATGCCGAG |
| AF270425 | AGACTGGGTGTGAGTTACCATTTCACCATTTCACCAAGGAGATCGAAGATGAACTAGAGAATATCTACCATAACA---ACAAT---GATGCCGAG |
| U88318 | GGACTGGGTGTGAGTTACCATTTCACCAAGGAGATCGAAGATGAACTAGAGAATATCTACCATAACA---ACAAT---GATGCCGAG |
| Y16432 | AGACTGGGTGTGAGTTACCATTTCACCAAGGAGATCGAAGATGAACTAGAGAATATCTACCATAACA---ACAAT---GATGCCGAG |
| AF174294 | AGACTGGGTGTGAGTTACCATTTCACCAAGGAGATCGAAGATGAACTAGAGAATATCTACCATAACA---ACAAT---GATGCCGAG |
| U23206 | AGACTGGGTGTGAGTTACCATTTCACCAAGGAGATCGAAGATGAACTAGAGAATATCTACCATAACA---ACAAT---GATGCCGAG |
| X95323 | AGACTGGGTGTGAGTTACCATTTCACCAAGGAGATCGAAGATGAACTAGAGAATATCTACCATAACA---ACAATATTGATGCCGAG |
| AY800107 | AGACTGGGTGTGAGTTACCGATTCACCAAAGAGATCGAAGATCGAGAACATGAGAACATCTACCATAACA---ACAAT---GATGCCGAA |
| X96429 | AGATTAGGTGTGAGTTATCATTTTGAGAAAGAGATTGAAGATGAACTAGAGAATATTTACCGTGACACCAACAACAATGATGCGGAC |
| | *  *  ***** ****** *  **  **  ****** **** ***** ******* *** *****  *   *  ****** |

*FIGURE 13 (CONT'D)*

```
U23205     AACGACCTCTACACCACATCCCTTCGATTCGATTACTCCGAGAGAGCATGGATTCAATGTTTCATGCGACGTATTCAACAAGTTTAAA
AF270425   AACGACCTCTACACCACATCCCTTCGATTCCTTCGATTCCGACTACTCCGAGAGAGCATGGATTCAATGTTTCATGCGACGTATTCAACAAGTTTAAA
U88318     AACGACCTCTACACCACATCCCTTCGATTCTCTTCGATTCCGACTACTCCGAGAGAGCATGGATTCCATGTTTCATGCGACGTATTCAACAAGTTTAAA
Y16432     AACGACCTCTACACTACATCTCTTCGATTCTCTTCGATTCCGACTACTCCGAGAGAGCATGGATACAATGTTTCATGCGACGTATTCAACAAGTTTAAA
AF174294   AACGACCTCTACACTACATCTCTTCGATTCTCTTCGATTCCGACTACTCCGAGAGAGCATGGATACAATGTTTCATGCGACGTATTCAACAAGTTTAAA
U23206     AACGACCTCTACACCACATCCATTCGATTCTCTTCGATTCCGACTACTCCGAGAGAGCATGGATACAATGTTTCATGCGACGTATTCAACAAGTTTAAA
X95323     AACGACCTCTACACTACATCTCTTAGATTCGATTCCTTAGATTCCGATTACTCCGAGAGAGCATGGATTCAATGTTTCATGCGACGCATTCAACAAGTTAAG
AY800107   AATGACCTCTACACTACATCTCTTCGATTTCGATTCCGATTCCGATTACTCCGAGAGAGCATGGATTCAATGTTTCATGTGAGGTATTCAACAAGTTTAAA
X96429     ACCGATCTCTACACTACAGCTCTTCGATTCCGGTTACTTAGAGAGAGCATGGCTTCGATATTTCTTGTGATGCATTCAACAAGTTCAAA
           *  ** ********* ***  *  **  *****  *  *****  ****  *  ** ***** *  ** ***********  **

U23205     GACGAGCAAGGGAATTTCAAGTCATCCGTGACAAGCGATGTTGTTGGAACTTACCAAGCTTCCTATTTGAGGGTTCAT
AF270425   GACGAGCAAGGAATTTCAAGTCATCCGTGACAAGCGATGTTGTTGGAACTTACCAAGCTTCCTATTTGAGGGTTCAT
U88318     GACGAGCAAGGAATTTCAAGTCATCCGTGACAAGCGATGTTGTTGGAACTTACCAAGCTTCCTATTTGAGGGTTCAT
Y16432     GACGAGCAAGGAATTTCAAGTCATCCGTGACAAGCGATGTTGTTGGAACTTACCAAGCTTCCTATTTGAGGGTTCAT
AF174294   GACGAGCAAGGAATTTCAAGTCATCCGTGACAAGCGATGTTGTTGGAACTTACCAAGCTTCCTATTTGAGGGTTCAT
U23206     GATGAGCAAGGAATTTCAAGTCATCCGTGACACTCGTGACAAGCGATGTTGTTGGAACTTACCAAGCTTCTTATTTGAGGGTTCAT
X95323     GAAGAGCAAGGAATTTCAAGTCATCATCCGTGACAAACAATGTTGTTGGAACTTACCAAGCTTACGAGGCCTCCTATTTGAGGGTTCAT
AY800107   GACGAGCAAGGGATTTTAAGTCATCATTGACAAGCGATGTTGTGGAGCTTACGAAGCTTGTCGTATTTGAGGGTTCAT
X96429     GATGAGGCAGGAACTTCAAGGCATCATTGACAAGTGATGTGCAAGGTTGTTGGAACTTTATGAAGCTTCCTATATGAGGGTCCAT
           **  *** ** **  ** ***  ****  **** *  ** *** *** * *********       * *** ******** ***
```

*FIGURE 13 (CONT'D)*

| | |
|---|---|
| U23205 | GGGGAAGATATATTGGATGAAGCAATTCTTTCACCACCAACCATTTAAGCCTTGCAGTAGCATCTTTGGACTATCCGTTATCCGAA |
| AF270425 | GGGGAAGATATATTGGATGAAGAAGCAATTTCTTTCACCAGCAACCATTTAAGCCTTGCAGTAGCATCTTTGGACCATCCTTATCCGAA |
| U88318 | GGGGAAGATATATTGGATGAAGCAATTTCTTTCACCAGCAACCATTTAAGCCTTGCAGTAGCATCTTTGGACCATCCTTATCCGAA |
| Y16432 | GGGGAAGATATATTGGATGAAGCAATTCTTTCACCACCAACCATTTAAGCCTTGCAGTATCATCTTTGGACCATCCTTGTCCGAA |
| AF174294 | GGGGAAGATATATTGGATGAAGCAATTCTTTCACCACCAACCATTTAAGCCTTGCAGTAGCATCTTTGGACCATCCTTATCCGAA |
| U23206 | GGGGAAGATATATTGGATGAAGCAATTCTTTCACCACCACCATTTAAGCCTTGCAGTAGCATCTTTGGACCATCCTTGTCCGAA |
| X95323 | GGGGAAGATATATTGGATGAAGAAGCAATTTCTTCTCCGCCAACAATTTAAGCCTTGCAGTGCATCTTTGGACTATCCTTGTCCGAA |
| AY800107 | GGGGAAGATATATTGGATGAAGCGATTTCTTTCACTACTGACCATTTAACCCTTGCAGTAGCAACTTTAGAATATCCTTTGTCTGAA |
| X96429 | GGGGAAGATACTCGATGAAGCCATTCTTTCACCATTCTTTCACCCATTGCTCTACCAACTTACACTTTATCGGAA |
|  | * ********** * ******** ****** * * * * * ***** * *** ** ** *** |
| U23205 | GAGGTTTCACATGCTTTGAAACAATCAATTCGAAGAGGCTTGAGGCAAGACACTATCTTTCAGTATACCAAGATATT |
| AF270425 | GAGGTTTCTCATGCTTTGAAACAATCAATTCGAAGAGGCTTGCCAAGGGTTGAGGCAAGACACTATCTTTCAGTATACCAAGATATT |
| U88318 | GAGGTTTCTCATGCTTTGAAACAATCAATTCGAAGAGGCTTGCCAAGGGTTGAGGCAAGACACTATCTTTCAGTATACCAAGACATT |
| Y16432 | GAGGTTTCTCATGCTTTGAAACAATCAATTCGAAGAGGCTTGCCAAGGGTTGAGGCAAGCACTATCTTTCAGTATACCAAGATATT |
| AF174294 | GAGGTTTCTCATGCTTTGAAACAATCAATTCGAAGAGGCTTGTCAAGGGTTGAGGCAAGCACTATCTTTCAGTATACCAAGATATT |
| U23206 | GAGGTTTCTCATGCTTTGAAACAATCAATTCGAAGAGGCTTGCCCAGGGTTGAGGCAAGGCACTATCTTTCAGTATACCAAGATATT |
| X95323 | CAGGTTTCTCATGCTTTGAAACAATCAATTCGAAGAGGCTTGCCAAGGGTTGAGGCAAGGCACTATCTTTCAGTATACCAAGATATT |
| AY800107 | CATGTTTCTCATGCTTTGAAAAATCAATCCGAAGAGGATTGCCAAGGATTGAGGCAAGGCACTATCTTTCAGTATACCAAGATATT |
| X96429 | CAGGTCGGCCATGCCTTAAAGCAGTCTATCCGAAGGGGCTTGAGGCCCGGAATTTCATTCGATATACCAAGATTTA |
|  | * ** ******** ** * * ** * ***** **** *********** * |

```
U23205      GAGTCCCATAATAAGGTTTTGTTGGAGTTTGCTAAGATCGATTTCAACATGGTACAACTTTTGCATAGGAAAGAGCTAAGTGAGAAT
AF270425    GAGTCCCATAATAAGGTTTTGTTGGAGTTTGCTAAGATCGATTTCAACATGGTACAACTTTTGCATAGAAAAGAGCTAAGTGAGAAT
U88318      GAGTCCCATAATAAGGTTTTGTTGGAGTTTGCTAAGATCGATTTCAACATGGTACAACTTTTGCATAGAAAAGAGCTAAGCGAGAAT
Y16432      GAGTCCCACAATAAGGCTTTGTTGGAGTTTGCTAAGATCGACTTCAACATGTTACAATTTTTGCATAGGAAAGAGCTAAGCGAGAAT
AF174294    GAGTCCCATAATAAGGCTTTGTTGGAGTTTGCTAAGATCGACTTCAACATGTTACAATTTTTGCATAGGAAAGAGCTAAGCGAGAAT
U23206      GAGTCCCATAATAAGGCTTTGTTGGAGTTTGCTAAGATCGATTTCAACATGTTACAATTTTTGCATAGGAAAGAGCTAAGTGAGAAT
X95323      GAGTCCCATAATAAGGCTTTGTTGGAGTTTGCTAAGATCGATTTCAACATGTTACAACTTTTGCATAGGAAAGAGCTAAGTGAGAAT
AY800107    GAATCCCACAATACGGCTTTGTTGTTGGAGTTTGCTAAGATCGATTTCAACATGTTACAACTTTTGCATAGGAAAGAGCTAAGTGAGAAT
X96429      GAATCCCATAACAAATCGTTCTTCAATTGCAAAGATTGATTTCAACTTGTTGCAGCTTGTTGCATAGAAGAGCTAAGTGAGATC
            ** ****** **    *     ***  *     *******  ** * *******  **  *     *  *************

U23205      TCTAGGTGGTGGAAGGATTAGACTTTCAAAGAAAGTTGCCATACGCAAGAGATAGAGTTGTTGAAGGCTATTTTTGGATCTCAGGA
AF270425    TCTAGGTGGTGGAAGGATTAGACTTTCAAAGAAAGTTGCCATACGCAAGAGATAGAGTTGTTGAAGGCTATTTTTGGATCTCAGGA
U88318      TCTAGGTGGTGGAAGGCTTAGACTTTCAAAGAAAGTTGCCATACGCAAGAGATAGAGTTGTTGAAGGCTATTTTTGGATCTCAGGA
Y16432      TGTAGGTGGTGGAAAGATTAGACTTTCAAAGAAAGTTGCCATATGCAAGAGATAGAGTTGTTGAAGGCTATTTTTGGATCTCAGGA
AF174294    TGCAGGTGGTGGAAGGATTAGACTTTCAAAGAAAGTTGCCATATGCAAGAGATAGAGTTGTTGAAGGCTACTTTTGGATCTCAGGA
U23206      TGTAGGTGGTGGAAGGATTAGACTTTCAAAGAAAGTTGCCATATGCAAGAGATAGAGTTGTTGAAGGCTTACTTTTGGATCTCTGGA
X95323      TTTAGGTGGCGGAATGATTAGACTTTCAAACAAAGTTGCCATATACAAAAGATAGAGTTGTTGAATGCTATTTTTGGATCTTGGA
AY800107    TGTAG-TGGTGGAAGGATTAGACTTTCAAAAGAAGTTGCCATATGTTAAGAGACAGAGTTGGTTGAATGTTTTTTTTGGATCCTGGGA
X96429      TGCAGGTGGTGGAAAGATTAGACTTTACAAGAAAACTACCATTTGCAAGAAAATAGAGTTGGTTGAAGGCTATTTTGGATAATGGGA
            *  ** ***  ****** ******** *** ***   **   **    *   ***  * ****  *  ***  * **     *** 
```

*FIGURE 13 (CONT'D)*

| | |
|---|---|
| U23205 | GTGTACTTTGAGCCCCAATATTCTCTTGGTAGAAAGATGTTGACAAAAGTGATAGCAATGGCTTCTATTGTAGATGATACATATGAC |
| AF270425 | GTGTACTTTGAGCCCCAATATTCTCTTGGTAGAAAGATGTTGACAAAAGTGATAGCAATGGCATCTATTGTAGATGATACATATGAC |
| U88318 | GTGTACTTTGAGCCCCAATATTCTCTTGGTAGAAAGATGTTGACAAAAGTGATAGCAATGGCATCTATTGTAGATGATACATATGAC |
| Y16432 | GTGTACTTTGAGCCCCAATATTCACTTGGTAGAAAGATGTTGACAAAAGTGATAGCAATGGCATCTATTGTAGATGATACATATGAC |
| AF174294 | GTGTACTTTGAGCCCCAATATTCACTTGGTAGAAAGATGTTGACAAAAGTGATAGCAATGGCATCTATTGTAGATGATACATATGAC |
| U23206 | GTGTACTTTGAGCCCCAATATTCACTTGGTAGAAAGATGTTGACAAAAGTGATAGCAATGGCATCCATTGTAGATGATACATATGAC |
| X95323 | GTGTACTTTGAGCCCCACTATTCACTTGGTAGAAAGATGATGACAAAAGTGACAAAAGTGATAATAATGACACCTGTTATAGATGATACATATGAC |
| AY800107 | GTGTACTTTGAGCCCCAATATTCACTTGGTAGAAAGATATTGACAAAAGTGATAGCTATGACTTCTGTTATAGATGATACATATGAC |
| X96429 | GTTTACTTTGAACCCCAATACTCTCTTGGTAGAAAGATGTTGACAAAAGTCATAGCAATGGCTTCCATTGTTGATGATACTTATGAT |
| | ** ********* ****** ** ** ************** *** *** * * ********* ***** |
| U23205 | TCATATGCAACATATGAAGAGCTCATTCCCTATACAAAAGCAATTGAGA-GGTGGGATATCAAATGCATAGATGAACTTCCTGAATA |
| AF270425 | TCATATGCAACATATGAAGAGCTCATTCCCTATACAAATGCAATTGAGA-GGTGGGATATCAAATGCATAGATGAACTTCCTGAATA |
| U88318 | TCATATGCAACATATGAAGAGCTCATTCCCTATACAAATGCAATTGAGA-GGTGGGATATCAAATGCATAGATGAACTTCCTGAATA |
| Y16432 | TCATATGCAACATATGAAGAGCTCATTCCCTATCCAAATGCAATTGAGA-GGTGGGATATCAAATGCATAGATGAACTTCCTGAATA |
| AF174294 | TCATATGCAACATATGAAGAGCTCATTCCCTATACAAATGCAATTGAGA-GGTGGGATATCAAATGCATAGATGAACTTCCTGAATA |
| U23206 | TCATATGCAACATATGAAGAGCTCATTCCCTATACAAATGCAATTGAGA-GGTGGAGGTGGGATATCAAATGCATAGATGAACTTCCTGAATA |
| X95323 | TCATATGCAACATATGATGAGCTCAATCCCTATACAAGTGCTATTGAG----TGGGAAATTAAATGCATAGACCAACTTCCAGAATA |
| AY800107 | TCATATGCAACATATGATGAGCTCAATCCCTATACAAATGCAATTGAGA-GGTGGGATATCAAATGCATAGACCAACTTCCAGAATA |
| X96429 | TCATATGCAACCTATGATGAACTCATTCCCTATACAAATGCAATTGAAA-GGTGGGATATTAAATGCATGAACCAACTCCCGAATTA |
| | ********** ***** ** * *** ** ******** * ****** ** * ** ****** * * |

*FIGURE 13 (CONT'D)*

| | |
|---|---|
| U23205 | CATGAAACCAAGCTACAAAGCGCTATTAGATGTTTATGAAGAAATTGGTGGCTAAGCATGGGAGACAATATCGTGTCGA |
| AF270425 | CATGAAGCCGAGCTACAAGGCACTATTAGATGTTTATGAAGAAATGGAACAACTGGTGGCTGAGCATGGGAGACAATATCGTGTCGA |
| U88318 | CATGAAACCGAGCTACAAGGCACTATTAGATGTTTATGAAGAAATGGAACAACTGGTGGCTGAGCATGGGAGACAATATCGTGTCGA |
| Y16432 | CATGAAGCCGAGCTACAAGGCACTATTAGATGTTTATAAAGAAATGGAACAACTGGTGGCTGAGCATGGGAGACAATATCGTGTCGA |
| AF174294 | CATGAAGCCGAGCTACAAGGCACTATTAGATGTTTACGAAGAAATGGAACAACTGGTGCCTGAGCATGGGAGACAATATCGTGTCGA |
| U23206 | CATGAAACCAAGCTACAAGGCTCTATTAGATGTTTATGAAGAAATTGGTGGCTGAGCATGGGAGACAATATCGTGTCGA |
| X95323 | TATGAAACTGAGCTACAAGGCACTATTAGATGTTTATGAAGAAATGAAACAACTACTGCTGAGCACGGAGACAATATCGTGTCGA |
| AY800107 | CATGAAACTGAGCTACAAGGCATTATTAGATGTTTATGAAGAAATGGAACAACTGATGCTGAGGATGAAGACAATATCGTGTAGA |
| X96429 | CATGAAAATAAGCTACAAGGCACTATTAAATGTTTATGAAGAAATGGAACAGCTGTT-GGCAAATCAAGGGAGACAGTACCGAGTTGA |
|  | ***** ********** ** ****** ******* ** * ** ****** *** * ** * ** |
|  | |
| U23205 | ATATGCGAAAAATGCGA--TGATACGACTTGCTCAATCTTATCTTGTGAGGCCAGATGACTCTTCAAAACTACAAACCATCATT |
| AF270425 | ATATGCGAAAAATGCGA--TGATACGACTTGCTCAATCTTATCTTGTGGAGGCCAGATGGACTCTTCAAAACTACAGCCATCATC |
| U88318 | ATATGCGAAAAATGCGA--TGATACGACTTGCTCAATCTTATCTTGTGGAGGCCAGATGGACTCTTCAAAACTACAAGCCATCATC |
| Y16432 | ATATGCGAAAAATGCGA--TGATACGACTTGCTCAATCTTATCTTGTGGAGGCCAGATGGACTCTTCAAAACTACAAGCCATCATC |
| AF174294 | ATATGCGAAAGAATGCGAGATGATACGACTTGCTCAATCTTGCTCAATCTTACCTTGTGGAGGCCAGATGACTCTTCAAAACTACAAACCATCATC |
| U23206 | GTATGCGAAGAATGCGA--TGATACGACTTGCTCAATCTTATCTTGTGGAGGCCAAATGGACTCTTCAAAACTATAAACCATCATC |
| X95323 | ATATGCGAAAAATGCAA--TGATACGACTTGCTCAATCCTATTTGTGGAGGCCAAATGGACTCTTCAAAACTACAAACCATCATC |
| AY800107 | ATATGCCAAAAATATAA--TGATACAACTTGCTCAAGCTTTCCTTATGGAGGCCAAATGGACTCTTCAAAACCACAAACCATCATC |
| X96429 | GTATGCGAAAAGGCGA--TGATACGTCTTGTTCAAGCTTACCTTTTGGAGGCCAAATGGACTCATCAAAATTATAAACCAACCTTT |
|  | ***** *** * ** ** ** * *** *** ********* ****** ***** * ** **** |

*FIGURE 13 (CONT'D)*

| | |
|---|---|
| U23205 | GAGGAGTTTAAGGCTAATGCATTGCCAACTTGTGGTTATGCCATGCTTGCTATTACATCTTTCGTCGGCATGGGAGATATTGTAACA |
| AF270425 | GAGGAGTTTAAGGCTAATGCATTGCCAACTTGTGGTTATGCCATGCTTGCTATTACATCTTTCGTTGGCATGGGAGATATTGTAACA |
| U88318 | GAGGAGTTTAAGGCTAATGCATTGCCAACTTGTGGTTATGCCATGCTTGCTATTACATCTTTCGTTGGCATGGGAGATATTGTAACA |
| Y16432 | GAAGAGTTTAAGGCTAATGCATTGCCAACTTGTGGTTATGCCATGCTTGCTATTACATCTTTCGTCGGCATGGGAGATATCGTAACA |
| AF174294 | GAGGAGTTTAAGGCTAATGCATTGCCAACTTGTGGTTATGCCATGCTTGCTATTACATCTTTCGTCGGCATGGGAGATATCGTAACA |
| U23206 | GAGGAGTTTAAGGCTAATGCATTGCCAACTTGTGGTTATGCCATGCTTGCTATTACATCTTTCGTCGGCATGGGAGATATCGTAACA |
| X95323 | GAGGAATTTAAGATTAATGCATTGTCATCTACTGGTTATGCCATGCTTGCTATTACATCTTCGTCGGTATGAGAGATATCGTAACA |
| AY800107 | GAGGAGTTTAAGGCTACTGCATTGCAAACTACTGGTTATGCCATGCTTGCTATTACAGCTTTAGTTGACATGGGAGATATTGTAACA |
| X96429 | GAGGAATTTAGAGATAATGCATTGCCAACCTCTGGCTATGCCATGCTTGCTATAACGGCGTTTGTCGGCATGGGCGAAGTTATAACC |
| | ** ** ****   **  ** ********  **    **  *** ** ** * ***  ** * **  *** * **** |
| | |
| U23205 | CCAGAAACCTTTAAATGGGCAGCCAATGACCCTAAGATCATTCAAGCTTCCACAATTATTGTAGTTTATGGATGATGTTGCTGAA |
| AF270425 | CCAGAAACCTTTAAATGGGCAGCCAATGACCCTAAGATCATTCAAGCTTCCACAATTATTGTAGTTTATGGATGATGTTGCTGAA |
| U88318 | CCAGAAACCTTTAAATGGGCAGCCAATGACCCTAAGATAATTCAAGCTTCCACAATTATTGTAGTTTATGGATGATGTTGCTGAA |
| Y16432 | CCAGAGACCTTTAAATGGGCAGCCAATGACCCTAAGATAATTCAAGATAATTCAAGCTTCCACAATTATTGTAGTTTATGGATGATGTTACTGAA |
| AF174294 | CCAGAGACCTTTAAATGGGCAGCCAATGACCCTAAGATCATTCAAGCTTCCACAATTATTGTAGTTTATGGATGATGTTGCGGAA |
| U23206 | CCAGAGACCTTTAAATGGGCAGCCAATGACCCTAAGATCATTCAAGCTTCCACAATTATTGTAGTTTATGGATGATGTTGCGGAA |
| X95323 | CCAGAGACCTTTAAATGGGCAGCCAGTAGTGACCCAGTGACCCAGTGACCCAGCCAGTAGTGACCCAGCCAGTAGTCAAGCGTCCACAATTATTGTAGTTTATGGATGATGTTGCTGAA |
| AY800107 | CCAGAGACCTTTAAATGGGCAGCCAGTGACCCAGTAATAACCCTAAGATCTTCCGCAATTATTCAAGCTTCCACAATTATTGTAGTTTATGGATGATATTGCTGAA |
| X96429 | CCTGAGACCTTCAAATGGGCCGCCCAGTGACCCCAGTGACCCCAAGATCATTAAGGCTTCCACCATTATTGCAGGTTCATGGACGATATTGCTGAG |
| | ** * *****  ****** ***   ** ***  *  *** **  **   *  *  ** ** ****  ***  ***** |

*FIGURE 13 (CONT'D)*

| | |
|---|---|
| U23205 | CACAAGTTCAAACATAGGAGAGAAGACGATTGCTCAGCAATTGAGTGTTTACATGGAAGAATATGGCGTAACAGCACAAGAGGCATAT |
| AF270425 | CACAAGTTCAAACATAGGAGAGAAGACGATTGCTCAGCAATTGAGTGTTTACATGGAAGAATATGGTGTAACAGCACAAGAGGCATAT |
| U88318 | CACAAGTTCAAACATAGGAGAGAAGACGATTGCTCAGCAATTGAGTGTTTACATGGAAGAATATGTGTAACAGCACAAGAGGCATAT |
| Y16432 | CACAAGTTTAAGCATAGGAGAGAAGACGAAGATGATTGCTCAGCAATAGAGTGTTTACATGGAAGAATATGGCGTATCAGCACAAGAGGCATAC |
| AF174294 | CACAAGTTTAAGCATAGGAGAGAAGACGATTGCTCAGCAATTGAGTGTTTACATGGAAGAATATGGCGTATCAGCACAAGAGGCATAT |
| U23206 | CACAAGTTCAAGCATAGGAGAGAAGACGATTGCTCAGCAGTGTTTACATCGAGTGTTTACATGGAAGAATATGGCGTAACAGCACAAGAGGCATAT |
| X95323 | CACAAGTTCAAGCATAGGAGAGAAGACGATTGGTCAGTCAGTATTACATCGACTAATCATGAAAGAATATAACGTAACAGCACACACATAC |
| AY800107 | CACAAGTTCAAGCAGAGAGAGAAGAAGATGATTCTCGGGAATTGAGTGTTTACATGGAAGAATATGGCGTAATGGTACAAGAAGCATAC |
| X96429 | CATAAGTTCAACCATAGGAGAGAAGACGATTGCTCAGCAATTGCTCAGCAATCGAATTGCTACATGAAACAATATGGGGTGACAGCGCAGGAAGCATAC |
| | ** ****** ** ** ********* **** ** *** ** ** ******** ** ***** * ** * ** ** ***** |
| U23205 | GATGTATTCAACAAGCATGTTGAAAGTGCTTGGAAGGATGTGAATAAAGAGTTCCTGAAACCAACAGAAATGCCAACAGAAGTTTTG |
| AF270425 | GATGTATTCAACAAGCATGTTGAGAGTGCTTGGAAGGATGTGAATCAAGAGTTTCTGAAACCAACAGAAATGCCAACAGAAGTTTTG |
| U88318 | GATGTATTCAACAAGCATGTTGAGAGTGCTTGGAAGGATGTGAATCAAGAGTTTCTGAAACCAACAGAAATGCCAACAGAAGTTTTG |
| Y16432 | GATGTATTCAACAAGCATGTTGAGAGTGCCTGGAAGGATGTCAAGAGTTTCAGAAGTTTCAGAACCAACAGAAATGCCAACAGAAGTTTTA |
| AF174294 | GATGTATTCAACAAGCATGTTGAGAGTGCTTGGAAGGATGCTTGGAAGGATGTGAATCAAGAGTTCTGAAACCAACAGAAATGCCAACAGAAGTTTTA |
| U23206 | GATGTATTCAACAAGCATGTTGAGAGTGCTTGGAAGGATGCTTGGAAGGATTAAATCAAGAGTTTTGAAACCAACAGAAATGCCAACAGAAGTTTTG |
| X95323 | GATGTATTCAACAAGCATGTTGAGAGTGCTTGGAAAGATATGAATCAAGAGCTTCTGAAACCAACAGAAATGCCAACAGAAGTTTTG |
| AY800107 | GATGTATTCAACAAATATATTGAGAGTGCCTGGAAGATGTGAATAAAAGGTTTTGAAACCAACCGAAATGCCAATAGAAGTTTTG |
| X96429 | AATGTGTTTTACAAGCATATCGAGAGTTCATGGAAGAGTTCATGGAAAGATGTAAATGAAGATGTAAATGAAGTTCTTGAAACCGACACCCGTTCTT |
| | *** ** ** ** **** * * * * *** * ** * *** * ** *** * ****** ** ********** * * * |

*FIGURE 13 (CONT'D)*

| | |
|---|---|
| U23205 | AATCGTAGCCTAAACCTTGCAAGGGTGATGGATGTACTTTACAGAGAAGGTGATGGCTACACATATGTTGGAAAAGCTGCTAAGGGT |
| AF270425 | AATCGTAGCTTAAACCTTGCAAGGGTGATGATGTACTCCTACAGAGAAGGTGATGGCTACACATATGTTGGAAAAGCGGCTAAGGGT |
| U88318 | AATCGTAGCTTAAACCTTGCAAGGGTGATGATGTACTCCTACAGAGAAGGTGATGGCTACACATATGTTGGAAAAGCGGCTAAGGGT |
| Y16432 | AATCGTAGCCTAAACCTTGCAAGGGTGATGATGTACTTTACAGGGAAGGAGATACATATGTTGGAAAAGCGGCTAAGGGT |
| AF174294 | AATCGTAGCCTAAACCTTGCAAGGGTGATGATGTACTTTACAGGGAAGGAGATACATATGTTGGAAAAGCGGCTAAGGGT |
| U23206 | AATCGTAGCCTAAACCTTGCAAGGGTGATGATGTGCTTTACAGGGAAGGCGATGGCTATACATATGTTGGAAAAGCGGCAAAGGGT |
| X95323 | AATCGTAGCCTAAACCTTTCGAGGGTAATGATGTGTTTACAAGGAAGGAGATGGCTATACATATGTTAGAAAAGCGATGAAAGAT |
| AY800107 | AATCGTATACTAAATCTTGCAAGGGTGATGAATGTGCTTTACAACGAAGGTGATGGCTATACATATGTTGGGAAGCAACTAAGGGT |
| X96429 | TGTCGTAGCCTCAACCTTGCTAGGGTTATGGATGTACTTTACAGAGAAGGTGATGGTTATACACATGTTGGGAAAGCTGCTAAAGGT |
| | ***** * *** * ****** * **** ** *** ****** * ***** ** ***** ****** |

| | |
|---|---|
| U23205 | GGAATCACTTCATTACTCATTGAACCAGTTGCACTTTGAAATC |
| AF270425 | GGAATCACTTCATTACTCATTGAACCAATTGCACTTTGAAATC |
| U88318 | GGAATCACTTCATTACTCATTGAACCAATTGCACTTTGAAATC |
| Y16432 | GGAATCACTTCATTGCTTATTGAACCAATTGCACTTTGAAATT |
| AF174294 | GGAATCACTTCATTGCTCATTGAACCAATTGCACTTTAAAATT |
| U23206 | GGAATCACTTCATTGCTCATTGAACCAATTGCACTTTGAAATT |
| X95323 | GGAATCACTTCATTGCTCATTGAACCAATTGCACTTTGAAATT |
| AY800107 | GTAATCACTTCATTGTTGATTGAGCCAGTCACACTTTGAAATT |
| X96429 | ATTATCAGCATATTGATTGATCCAATACAAATTTGAAATT |
| | **** *** * ****** ** * *** *** |

*FIGURE 13 (CONT'D)*

SEQUENCE LISTING

```
<160> NUMBER OF SEQ ID NOS: 22

<210> SEQ ID NO 1
<211> LENGTH: 604
<212> TYPE: DNA
<213> ORGANISM: Gossypium sp.

<400> SEQUENCE: 1
atgccgagaa cgacctctac accacatccc ttcgattccg attactccga gagcatggat      60
tcaatgtttc atgcgacgta ttcaacaagt ttaaagacga gcaagggaat ttcaagtcat     120
ccgtgacaag cgatgttcga ggattgttgg aactttacca agcttcctat ttgagggttc     180
atggggaaga tatattggat gaagcaattt ctttcaccac caaccattta agccttgcag     240
tagcatcttt ggactatccg ttatccgaag aggtttcaca tgctttgaaa caatcaattc     300
gaagaggctt gccaagggtt gaggcaagac actatctttc agtataccaa gatattgagt     360
cccataataa ggtttttgttg gagtttgcta agatcgattt caacatggta caacttttgc     420
ataggaaaga gctaagtgag atttctaggt ggtggaagga tttagacttt caaagaaagt     480
tgccatacgc aagagataga gtggttgaag gctatttttg gatctcagga gtgtactttg     540
agccccaata ttctcttggt agaaagatgt tgacaaaagt gatagcaatg gcttctattg     600
taga                                                                   604

<210> SEQ ID NO 2
<211> LENGTH: 21
<212> TYPE: DNA
<213> ORGANISM: Artificial Sequence
<220> FEATURE:
<223> OTHER INFORMATION: Artificially synthesized PCR primer

<400> SEQUENCE: 2
atgccgagaa cgacctctac a                                                21

<210> SEQ ID NO 3
<211> LENGTH: 26
<212> TYPE: DNA
<213> ORGANISM: Artificial Sequence
<220> FEATURE:
<223> OTHER INFORMATION: Artificially synthesized PCR primer

<400> SEQUENCE: 3 actttttgtca acatctttct accaag                                          26

<210> SEQ ID NO 4
```

```
<211> LENGTH: 20
<212> TYPE: DNA
<213> ORGANISM: Artificial Sequence
<220> FEATURE:
<223> OTHER INFORMATION: Artificially synthesized PCR primer

<400> SEQUENCE: 4
gaagcctcat cgataccgtc                                              20

<210> SEQ ID NO 5
<211> LENGTH: 19
<212> TYPE: DNA
<213> ORGANISM: Artificial Sequence
<220> FEATURE:
<223> OTHER INFORMATION: Artificially synthesized PCR primer

<400> SEQUENCE: 5
ctaccactac catcatggc                                               19

<210> SEQ ID NO 6
<211> LENGTH: 26
<212> TYPE: DNA
<213> ORGANISM: Artificial Sequence
<220> FEATURE:
<223> OTHER INFORMATION: Artificially synthesized PCR primer

<400> SEQUENCE: 6
cataggagag aagacgattg ctcagc                                       26

<210> SEQ ID NO 7
<211> LENGTH: 20
<212> TYPE: DNA
<213> ORGANISM: Artificial Sequence
<220> FEATURE:
<223> OTHER INFORMATION: Artificially synthesized PCR primer

<400> SEQUENCE: 7
ggaaatgaat acaaagacag                                              20

<210> SEQ ID NO 8
<211> LENGTH: 20
<212> TYPE: DNA
<213> ORGANISM: Artificial Sequence
<220> FEATURE:
<223> OTHER INFORMATION: Artificially synthesized PCR primer

<400> SEQUENCE: 8
tctacaatag aagccattgc                                              20

<210> SEQ ID NO 9
<211> LENGTH: 18
<212> TYPE: DNA
<213> ORGANISM: Artificial Sequence
<220> FEATURE:
<223> OTHER INFORMATION: Artificially synthesized PCR primer

<400> SEQUENCE: 9
gcgatcatag gcgtctcg                                                18

<210> SEQ ID NO 10
<211> LENGTH: 1144
<212> TYPE: DNA
<213> ORGANISM: Gossypium hirsutum

<400> SEQUENCE: 10
ctattttcat cctatttaga aatccaagtt gacacctaaa atttagttgg actgccatgt   60
```

```
aggattatcg ttagagagat aacggagctt aacggtagag tgatcacttt gtaacaaaat      120
aataacaaaa gtgactaaag tgtaacattt caaacataaa tgattaaaat ataacctgag      180
gcaaacaaaa atgactattt ttatagatta ccctaaaatt aaagagtcat ggccctagcc      240
cctcgcctac ttgtttgttt ttaataaact aacatagtat aatatattgt taggattata      300
taaaattatt aataaatagt ataattaatt taaaatttat gaaaaataaa ttaccatatt      360
tcttaaatac gtggcacctt atgttggatt ggactgtata acttatatac tattatctat      420
attgaatcca aatccttact tttaagcgtt tttagtgaaa catttttattt tccattctta      480 ttatataaat ttatataatg atataatatg taatacttag ataatattat tgaaaaagaa      540
taaaaatacc tcaaactttg aaaggactaa tttgtatgag catcaaacgt acaggatacc      600
aaaagtatac atatctgaat tgttcatat ctcctgcaac tcatagatca tcaccatgca      660
cagcaacatg tgtacacttg acttgtcctc tatcaactca acccttaact cagtgaatcg      720
ggacatctct gtctcacttt aaaaccttc ccagtttcaa cactctttga attcaactga      780
gttcacatac aacacaacac agtccatcat cttttctgctg ttaaagcatc atcatttcgc      840
cccttccagt tacagatgca acatgaaccc ccctgcaaca agtttgtcc gaaccttgct      900 agtaccatgt gaagggatgt ggcatctcga tatctaccca ccactataca aaaaaaaaa      960 aaagagacaa tatttcgtct tctttaattt gcacactcgt catcttgcat gtcaatgtct     1020
tcaacacgtt gatgaagatt tgcatgcaaa aatatcacct tccacagctc caccttctat     1080
aaatacatta ccactctttg ctattaccat cacacagtaa caaaatacag agcttatcgt     1140
aatc                                                                 1144

<210> SEQ ID NO 11
<211> LENGTH: 1108
<212> TYPE: DNA
<213> ORGANISM: Gossypium hirsutum

<400> SEQUENCE: 11
ctattttcat cctatttaga aatccaagtt gacacctaaa atttagttgg actgccatgt       60
aggattatcg ttagagagat aacggagctt aacggtagag tgatcacttt gtaacaaaat      120
aataacaaaa gtgactaaag tgtaacattt caaacataaa tgattaaaat ataacctgag      180
gcaaacaaaa atgactattt ttatagatta ccctaaaatt aaagagtcat ggccctagcc      240
cctcgcctac ttgtttgttt ttaataaact aacatagtat aatatattgt taggattata      300
taaaattatt aataaatagt ataattaatt taaaatttat gaaaaataaa ttaccatatt      360
tcttaaatac gtggcacctt atgttggatt ggactgtata acttatatac tattatctat      420
attgaatcca aatccttact tttaagcgtt tttagtgaaa catttttattt tccattctta      480 ttatataaat ttatataatg atataatatg taatacttag ataatattat tgaaaaagaa      540
taaaaatacc tcaaactttg aaaggactaa tttgtatgag catcaaacgt acaggatacc      600
aaaagtatac atatctgaat tgttcatat ctcctgcaac tcatagatca tcaccatgca      660
cagcaacatg tgtacacttg acttgtcctc tatcaactca acccttaact cagtgaatcg      720
ggacatctct gtctcacttt aaaaccttc ccagtttcaa cactctttga attcaactga      780
gttcacatac aacacaacac agtccatcat cttttctgctg ttaaagcatc atcatttcgc      840
cccttccagt tacagatgca acatgaaccc ccctgcaaca agtttgtcc gaaccttgct      900 agtaccatgt gaagggatgt ggcatctcga tatctaccca ccactataca aaaaaaaaa      960
```

```
aaagagacaa tatttcgtct tctttaattt gcacactcgt catcttgcat gtcaatgtct    1020
tcaacacgtt gatgaagatt tgcatgcaaa aatatcacct tccacagctc caccttctat    1080
aaatacatta ccactctttg ctattacc                                       1108

<210> SEQ ID NO 12
<211> LENGTH: 336
<212> TYPE: DNA
<213> ORGANISM: Gossypium hirsutum

<400> SEQUENCE: 12 ctatttcat cctatttaga aatccaagtt gacacctaaa atttagttgg actgccatgt      60
aggattatcg ttagagagat aacggagctt aacggtagag tgatcacttt gtaacaaaat   120
aataacaaaa gtgactaaag tgtaacattt caaacataaa tgattaaaat ataacctgag   180
gcaaacaaaa atgactattt ttatagatta ccctaaaatt aaagagtcat ggccctagcc   240
cctcgcctac ttgtttgttt taataaact aacatagtat aatatattgt taggattata    300
taaaattatt aataaatagt ataattaatt taaaat                             336

<210> SEQ ID NO 13
<211> LENGTH: 1681
<212> TYPE: DNA
<213> ORGANISM: Gossypium arboreum

<400> SEQUENCE: 13
tgatcaatcg aaatggcttc acaagtttct caaatgcctt cttcatcacc cctttcttcc     60
aataaggatg aaatgcgtcc caaagccgat tttcagccta gcatttgggg agatctcttc   120
ctcaactgtc ccgacaagaa tattgatgct gaaactgaaa agcgccacca acaattgaaa   180
gaagaagtaa ggaagatgat tgtggcacca atggctaatt caacccaaaa gttagccttc   240
attgattcag tccaaaggct gggtgtgagt taccatttca ctaaggagat cgaagatgaa   300
ctagagaata tctaccataa caacaatgat gccgagaacg acctctacac cacatccctt   360
cgattccgat tactccgaga gcatggattc aatgtttcat gcgacgtatt caacaagttt   420
aaagacgagc aagggaattt caagtcatcc gtgacaagcg atgttcgagg attgttggaa   480
ctttaccaag cttcctattt gagggttcat ggggaagata tattggatga agcaatttct   540
ttcaccacca accatttaag ccttgcagta gcatctttgg actatccgtt atccgaagag   600
gtttcacatg ctttgaaaca atcaattcga agaggcttgc caagggttga ggcaagacac   660
tatctttcag tataccaaga tattgagtcc cataataagg ttttgttgga gtttgctaag   720
atcgatttca acatggtaca acttttgcat aggaaagagc taagtgagaa ttctaggtgg   780
tggaaggatt tagactttca aagaaagttg ccatacgcaa gagatagagt tgttgaaggc   840 tattttttgga tctcaggagt gtactttgag ccccaatatt ctcttggtag aaagatgttg   900
acaaaagtga tagcaatggc ttctattgta gatgatacat atgactcata tgcaacatat   960
gaagagctca ttccctatac aaaagcaatt gagaggtggg atatcaaatg catagatgaa   1020
cttcctgaat acatgaaacc aagctacaaa gcgctattag atgtttatga agaaatggaa   1080
caattggtgg ctaagcatgg gagacaatat cgtgtcgaat atgcgaaaaa tgcgatgata   1140
cgacttgctc aatcttatct tgtggaggcc agatggactc ttcaaaacta caaaccatca   1200
tttgaggagt ttaaggctaa tgcattgcca acttgtggtt atgccatgct tgctattaca   1260
tctttcgtcg gcatgggaga tattgtaaca ccagaaacct ttaaatgggc agccaatgac   1320
cctaagatca ttcaagcttc cacaattatt tgtaggttta tggatgatgt tgctgaacac   1380
```

```
aagttcaaac ataggagaga agacgattgc tcagcaattg agtgttacat ggaagaatat    1440
ggcgtaacag cacaagaggc atatgatgta ttcaacaagc atgttgaaag tgcttggaag    1500
gatgtgaata aagagttcct gaaaccaaca gaaatgccaa cagaagtttt gaatcgtagc    1560
ctaaaccttg caagggtgat ggatgtactt tacagagaag gtgatggcta cacatatgtt    1620
ggaaaagctg ctaagggtgg aatcacttca ttactcattg aaccagttgc actttgaaat    1680
c                                                                    1681

<210> SEQ ID NO 14
<211> LENGTH: 1660
<212> TYPE: DNA
<213> ORGANISM: Gossypium hirsutum

<400> SEQUENCE: 14
caagtttctc aaatgccttc ttcatcaccc ctttcttcca ataaggatga aatgcgtccc      60
aaagccgatt ttcagcctag catttgggga gatttcttcc tcaattgtcc cgacaagaat     120
attgatgctg aaactcaaaa acgccaccaa caattgaaag aagaagtgag gaagatgatt     180
gtggcaccaa tggctaattc aacccaaaag ttagccttca ttgattcagt ccaaagactg     240
ggtgtgagtt accatttcac caaggagatc gaagatgaac tagagaatat ctaccataac     300
aacaatgatg ccgagaacga cctctacacc acatcccttc gattccgact actccgagag     360
catggattca atgtttcatg cgacgtattc aacaagttta agacgagca agggaatttc      420 aagtcatccg tgacaagcga tgttcgagga ttgttggaac tttaccaagc ttcctatttg     480
agggttcatg gggaagatat attggatgaa gcaatttctt tcaccagcaa ccatttaagc     540
cttgcagtag catcttttga ccatccttta tccgaagagg tttctcatgc tttgaaacaa     600
tcaattcgaa gaggcttgcc aagggttgag gcaagacact atctttcagt ataccaagat     660
attgagtccc ataataaggt tttgttggag tttgctaaga tcgatttcaa catggtacaa     720
cttttgcata gaaaagagct aagtgagaat tctaggtggt ggaaggatttt agactttcaa     780 agaaagttgc catacgcaag agatagagtg gttgaaggct attttttggat ctcaggagtg     840 tactttgagc cccaatattc tcttggtaga aagatgttga caaaagtgat agcaatggca     900
tctattgtag atgatacata tgactcatat gcaacatatg aagagctcat tccctataca     960
aatgcaattg agaggtggga tatcaaatgc atagatgaac ttcctgaata catgaagccg    1020
agctacaagg cactattaga tgtttatgaa gaaatggaac aactggtggc tgagcatggg    1080
agacaatatc gtgtcgaata tgcgaaaaat gcgatgatac gacttgctca atcttatctt    1140
gtggaggcca gatggactct tcaaaactac aagccatcat tcgaggagtt taaggctaat    1200
gcattgccaa cttgtggtta tgccatgctt gctattacat ctttcgttgg catgggagat    1260
attgtaacac cagaaaccct taaatgggca gccaatgacc ctaagataat tcaagcttcc    1320
acaattattt gtaggtttat ggatgatgtt gctgaacaca agttcaaaca taggagaaa     1380 gacgattgct cagcaattga gtgttacatg gaagaatatg gtgtaacagc acaagaggca    1440
tatgatgtat tcaacaagca tgttgagagt gcttggaagg atgtgaatca agagtttctg    1500
aaaccaacag aaatgccaac agaagttttg aatcgtagct aaaccttgc aagggtgatg    1560 gatgtactct acagagaagg tgatggctac acatatgttg gaaaagcggc taagggtgga    1620
atcacttcat tactcattga accaattgca ctttgaaatc                          1660

<210> SEQ ID NO 15
```

```
<211> LENGTH: 1681
<212> TYPE: DNA
<213> ORGANISM: Gossypium hirsutum

<400> SEQUENCE: 15
taatcaatcg aaatggcttc acaagtttct caaatgcctt cttcatcacc cctttcttcc      60
aataaggatg aaatgcgtcc caaagccgat tttcagccta gcatttgggg agatttcttc     120
ctcaattgtc ccgacaagaa tattgatgct gaaactcaaa aacgccacca acaattgaaa     180
gaagaagtga ggaagatgat tgtggcacca atggctaatt caaccctaaa gttagccttc     240
attgattcag tccagggact gggtgtgagt taccatttca ccaaggagat cgaagatgaa     300
ctagagaata tctaccataa caacaatgat gccgagaacg acctctacac cacatccctt     360
cgattccgac tactccgaga gcatggattc catgtttcat gcgacgtatt caacaagttt     420
aaagacgagc aagggaattt caagtcatcc gtgacaagcg atgttcgagg attgttggaa     480
ctttaccaag cttcctattt gagggttcat ggggaagata tattggatga agcaatttct     540
ttcaccagca accatttaag ccttgcagta gcatctttgg accatccttt atccgaagag     600
gtttctcatg ctttgaaaca atcaattcga agaggcttgc caagggttga ggcaagacac     660
tatctttcag tataccaaga cattgagtcc cataataagg ttttgttgga gtttgctaag     720
atcgatttca acatggtaca acttttgcat agaaaagagc taagtgagaa ttctaggtgg     780
tggaaggatt tagactttca aagaaagttg ccatacgcaa gagatagagt ggttgaaggc     840
tattttttgga tctcaggagt gtactttgag ccccaatatt ctcttggtag aaagatgttg     900
acaaaagtga tagcaatggc atctattgta gatgatacat atgactcata tgcaacatat     960
gaagagctca ttccctatac aaatgcaatt gagaggtggg atatcaaatg catagatgaa    1020
cttcctgaat acatgaaacc gagctacaag gcactattag atgtttatga agaaatggaa    1080
caactggtgg ctgagcatgg gagacaatat cgtgtcgaat atgcgaaaaa tgcgatgata    1140
cgacttgctc aatcttatct tgtggaggcc agatggactc ttcaaaacta caagccatca    1200
ttcgaggagt ttaaggctaa tgcattgcca acttgtggtt atgccatgct tgctattaca    1260
tctttcgttg gcatgggaga tattgtaaca ccagaaacct ttaaatgggc agccaatgac    1320
cctaagataa ttcaagcttc cacaattatt tgtaggttta tggatgatgt tactgaacac    1380
aagttcaaac ataggagaga agacgattgc tcagcaattg agtgttacat ggaagaatat    1440
ggtgtaacag cacaagaggc atatgatgta ttcaacaagc atgttgagag tgcttggaag    1500
gatgtgaatc aagggtttct gaaaccaaca gaaatgccaa cagaagtttt gaatcgtagc    1560
ttaaaccttg caagggtgat ggatgtactc tacagagaag gtgatggcta cacatatgtt    1620
ggaaaagcgg ctaagggtgg aatcacttca ttactcattg aaccaattgc actttgaaat    1680
c                                                                   1681

<210> SEQ ID NO 16
<211> LENGTH: 1681
<212> TYPE: DNA
<213> ORGANISM: Gossypium arboreum

<400> SEQUENCE: 16
tgatcaatcg aaatggcttc acaagtttct caaatgcctt cttcatcacc cctttcttcc      60
aataaggatg aaatccgtcc caaagccgat tttcagccta gcatttgggg agatttcttc     120
ctcaattgtc ccgacaagaa tattgatgct ggaactgaaa aacgccacca acaattgaaa     180
gaagaagtga ggaagatgat tgtggcacca atggctaatt cgacccaaaa gttagccttc     240
```

| | |
|---|---|
| attgattcag tccaaagact gggtgtgagt taccatttca ccaaggagat cgaagatgaa | 300 |
| ctagagaata tctaccataa caacaatgat gccgagaacg acctctacac tacatctctt | 360 |
| cgattccgac tactccgaga gcatggatac aatgtttcat gcgacgtatt caacaagttt | 420 |
| aaagacgagc aagggaattt caagtcatcc gtgacaagcg atgttcaagg attgttggaa | 480 |
| ctttaccaag cttcctattt gagggttcat ggggaagata tattggatga agcaatttct | 540 |
| ttcaccacca accatttaag ccttgcagta tcatctttgg accatccttt gtccgaagag | 600 |
| gtttctcatg ctttgaaaca atcaattcga agaggcttgc caagggttga ggcaaggcac | 660 |
| tatctttcag tataccaaga tattgagtcc cacaataagg ctttgttgga gtttgctaag | 720 |
| atcgacttca acatgttaca atttttgcat aggaaagagc taagcgagaa ttgtaggtgg | 780 |
| tggaaagatt tagactttca aagaaagttg ccatatgcaa gagatagagt ggttgaaggc | 840 |
| tatttttgga tctcaggagt gtactttgag ccccaatatt cacttggtag aaagatgttg | 900 |
| acaaaagtga tagcaatggc atctattgta gatgatacat atgactcata tgcaacatat | 960 |
| gaagagctca ttccatatac aaatgcaatt gagaggtggg atatcaaatg catagatgaa | 1020 |
| cttcctgaat acatgaagcc gagctacaag gcactattag atgtttataa agaaatggaa | 1080 |
| caactggtgg ctgagcatgg gagacaatat cgtgtcgaat atgcgaaaaa tgcgatgata | 1140 |
| cgacttgctc aatcttatct tgtggaggcc agatggactc ttcaaaacta caaaccatca | 1200 |
| ttcgaagagt ttaaggctaa tgcattgcca acttgtggtt atgccatgct tgctattaca | 1260 |
| tctttcgtcg gcatgggaga tatcgtaaca ccagagacct taaatgggc agccaatgac | 1320 |
| cctaagatca ttcaagcttc cacaattatt tgtaggttta tggatgatgt tgcggaacac | 1380 |
| aagtttaagc ataggagaga agatgattgc tcagcaatag agtgttacat ggaagaatat | 1440 |
| ggcgtatcag cacaagaggc atacgatgta ttcaacaagc atgttgagag tgcctggaag | 1500 |
| gatgtgaatc aagagtttca gaaaccaaca gaaatgccaa cagaagtttt aaatcgtagc | 1560 |
| ctaaaccttg caagggtgat ggatgtactt tacagggaag gagatggata tacatatgtt | 1620 |
| ggaaaagcgg ctaagggtgg aatcacttca ttgcttattg aaccaattgc actttgaaat | 1680 |
| t | 1681 |

<210> SEQ ID NO 17
<211> LENGTH: 1684
<212> TYPE: DNA
<213> ORGANISM: Gossypium arboreum

<400> SEQUENCE: 17

| | |
|---|---|
| tgatcaatcg aaatggcttc acaagtttct caaatgcctt cttcatcacc cctttcttcc | 60 |
| aataaggatg aaatccgtcc caaagccgat tttcagccta gcatttgggg agatttcttc | 120 |
| ctcaattgtc ccgacaagaa tattgatgct ggaactgaaa acgccacca caattgaaa | 180 |
| gaagaagtga ggaagatgat tgtggcaccg atggctaatt cgacccaaaa gttagccttc | 240 |
| attgattcac tccaaagact gggtgtgagt taccatttca ccaaggagat cgaagatgaa | 300 |
| ctagagaata tctaccataa caacaatgat gccgagaacg acctctacac tacatctctt | 360 |
| cgattccgac tactccgaga gcatggatac aatgtttcat gcgacgtatt caacaagttt | 420 |
| aaagacgagc aagggaattt caagtcatcc gtgacactcg atgttcgagg attgttggaa | 480 |
| ctttaccaag cttcctattt gagggttcat ggggaagata tattggatga agcaatttct | 540 |
| ttcaccacca accatttaag ccttgcagta gcatctttgg accatccttt atccgaagag | 600 |

```
gtttctcatg ctttgaaaca atcaattcga agaggcttgt caagggttga ggcaaggcac    660
tatctttcag tataccaaga tattgagtcc cataataagg ctttgttgga gtttgctaag    720
atcgacttca acatgttaca attttttgcat aggaaagagc taagcgagaa ttgcaggtgg   780
tggaaggatt tagactttca aagaaagttg ccatatgcaa gagatagagt tgttgaaggc    840
tacttttgga tctcaggagt gtactttgag ccccaatatt cacttggtag aaagatgttg    900
acaaaagtga tagcaatggc atctattgta gatgatacat atgactcata tgcaacatat    960
gaagagctca ttccctatac aaatgcaatt gagaaggtgg gatatcaaat gcatagatga   1020
acttcctgaa tacatgaagc cgagctacaa ggcattatta gatgtttacg aagaaatgga   1080
acaactggtg cctgagcatg aagacaata tcgtgtcgaa tatgcaaaga atgcgagatg    1140
atacgacttg ctcaatctta ccttgtggag gccagatgga ctcttcaaaa ctacaaacca   1200
tcattcgagg agtttaaggc taatgcattg ccaacttgtg gttatgccat gcttgctatt   1260
acatctttcg tcggcatggg agatatcgta acaccagaga cctttaaatg ggcagccaat   1320
gaccctaaga tcattcaagc ttccacaatt atttgtaggt ttatggatga tgttgcggaa   1380
cacaagttta gcataggag agaagacgat tgctcagcaa tagagtgtta catggaagaa    1440
tatggcgtat cagcacaaga ggcatacgat gtattcaaca agcatgttga gagtgcttgg   1500
aaggatgtga atcaagagtt tctgaaacca acagaaatgc caacagaggt tttaaatcgt   1560
agcctaaacc ttgcaagggt gatggatgta ctttacaggg aaggagatgg atatacatat   1620
gttggaaaag cggctaaggg tggaatcact tcattgctca ttgaaccaat tgcactttaa   1680
aatt                                                                 1684

<210> SEQ ID NO 18
<211> LENGTH: 1594
<212> TYPE: DNA
<213> ORGANISM: Gossypium arboreum

<400> SEQUENCE: 18
tgatcaatcg aaatggcttc acaagtttct caaatgcctt cttcatcacc cctttcttcc     60
aataaggatg aaatgcgtcc caaagccgat tttcagccta gcatttgggg agatctcttc    120
ctcaattgtc ccgacaagaa tattgatgct gaaactgaaa agcgccacca acaattgaaa    180
gaagaagtga ggaagatgat tgtggcacca atggctaatt caacccaaaa gttagccttc    240
attgattcag tccaaagact gggtgtgagt taccatttca ccaaggagat cgaagatgaa    300
ctagagaata tctaccataa caacaatgat gccgagaacg acctctacac cacatccatt    360
cgattccgac tactccgaga gcatggatac aatgtttcat gcgacgtatt caacaagttt    420
aaagatgagc aagggaattt caagtcatcc gtgacaagcg atgttcgagg attgttggaa    480
ctttaccaag cttcttattt gagggttcat ggggaagata tattggatga agcaatttct    540
ttcaccaccc accatttaag ccttgcagta gcatctttgg accatccttt gtccgaagag    600
gtttctcatg ctttgaaaca atcaattcga agaggcttgc ccagggttga ggcaaggcac    660
tatctttcag tataccaaga tattgagtcc cataataagg ctttgttgga gtttgctaag    720
atcgatttca acatgttaca attttttgcat aggaaagagc taagtgagaa ttgtaggtgg    780
tggaaggatt tagactttca aagaaagttg ccatatgcaa gagatagagt tgttgaaggt    840
tacttttgga tctctggagt gtactttgag ccccaatatt cacttggtag aaagatgttg    900
acaaaagtga tagcaatggc atccattgta gatgatacat atgactcata tgcaacatat    960
gaagagctca ttccctatac aaatgcaatt gagaggtggg atatcaaatg tatagatgaa   1020
```

```
attcccgaat acatgaaacc aagctacaag gctctattag atgtttatga agaaatggta    1080
caattggtgg ctgagcatgg gagacaatat cgtgtcgagt atgcgaagaa tgcgatgata    1140
cgacttgctc aatcttatct tgtggaggcc aaatggactc ttcaaaacta taaaccatca    1200
ttcgaggagt ttaaggctaa tgcattgcca acttgtggtt atgccatgct tgctattaca    1260
tctttcgtcg gcatgggaga tatcgtaaca cacaagttca agcataggag agaagacgat    1320
tgctcagcaa tcgagtgtta catggaagaa tatggcgtaa cagcacaaga ggcatatgat    1380
gtattcaaca agcatgttga gagtgcttgg aaggatttaa atcaagagtt tttgaaacca    1440
acagaaatgc caacagaggt tttgaatcgt agcctaaacc ttgcaagggt gatggatgtg    1500
ctttacaggg aaggcgatgg ctatacatat gttggaaaag cggcaagggg tggaatcact    1560
tcattgctca ttgaaccaat tgcactttga aatt                                1594

<210> SEQ ID NO 19
<211> LENGTH: 1684
<212> TYPE: DNA
<213> ORGANISM: Gossypium arboreum

<400> SEQUENCE: 19
tgatcaatcg aaatgacttc acaagtttcc caaatgcctt cttcatcatc acccctttct      60
tccaataagg atgaaatgcg tcccaaagcc gattatccgc ctagcatttg gggagatttc     120
ttccacaact gtcccgacaa gaatattgat gctgaaactg aaaaacgcca ccaacaattg     180
aaagaagaag tgaggaagat gattgtggca ccaatggcta attcaaccca aaagttaacc     240
ttcattgatt cagttcaaag actgggtgtg agttaccatt tcaccaagga gatcgaagat     300
gaactagaga acatctacca taacaacaat attgatgccg agaacgacct ctacactaca     360
tctcttagat tccgattact ccgagagcat ggattcaatg tttcatgcga cgcattcaac     420
aagtttaagg aagagcaagg gaatttcaag tcatctgtga caaacaatgt tcgaggattg     480
ttggaacttt acgaggcctc ctatttgagg gttcatgggg aagatatatt ggatgaagca     540
atttctttct ccgccaacaa tttaagcctt gcagtggcat cttggactat ccttttgtcc     600
gaacaggttt ctcatgcttt gaaacaatca attcgaagag gcttgccaag ggttgaggca     660
aggcactatc tttcagtata ccaagatatt gagtcccata taaggctttt gttggagttt     720
gctaagatcg atttcaacat gttacaactt ttgcatagga aagagctaag tgagaatttt     780
aggtggcgga atgatttaga ctttcaaaca aagttgccat atacaaaaga tagagtggtt     840
gaatgctatt tttggatctt gggagtgtac tttgagcccc actattcact tggtagaaag     900
atgatgacaa aagtgataat aatgacaccct gttatagatg atacatatga ctcatatgca     960
acatatgatg agctcaatcc ctatacaagt gctattgagt gggaaattaa atgcatagac    1020
caacttccag aatatatgaa actgagctac aaggcactat tagatgttta tgaagaaatg    1080
aaacaactac tggctgagca cgggagacaa tatcgtgtcg aatatgcgaa aaatgcaatg    1140
atacgacttg ctcaatccta ttttgtggag gccaaatgga ctcttcaaaa ctacaaacca    1200
tcattcgagg aatttaagat taatgcattg tcatctactg gttatgccat gcttgctatt    1260
acatctttcg tcggtatgag agatatcgta acaccagaga cctttaaatg ggcagccagt    1320
gaacctaaga tcattcaagc ttccgcaatt atttgtaggt ttatggatga tattgctgaa    1380
cacaagttca gcataggag agaagacgat tggtcagtaa tcgactatta catgaaagaa    1440
tataacgtaa cagcacacga cacatacgat gtattcaaca aatatattga gagtgcttgg    1500
```

| aaagatatga atcaagagct tctgaaacca acagaaatgc caacagaggt tatgaatcgt | 1560 |
| agcctaaacc tttcgagggt aatggatgtg gtttacaagg aaggagatgg ctatacatat | 1620 |
| gttagaaaag cgatgaaaga tgtaatcact tcattgttga ttgagccagt cacactttga | 1680 |
| aatt | 1684 |

<210> SEQ ID NO 20
<211> LENGTH: 1678
<212> TYPE: DNA
<213> ORGANISM: Gossypium hirsutum

<400> SEQUENCE: 20

| tcatcaaccg aaatggccaa acaagtttct caacttcttt cttcatcacc ccttacttcc | 60 |
| aacaaagatg aaatgcgtct gaaagccgac tttcagccta gcatttgggg agatctcttc | 120 |
| cttacttgtc tcgacaatga tatcgatgct gaaactgaac aacgccacca acagttggaa | 180 |
| ggaggagtga ggaagatgat tgtggcacca atggctaatt caacccaaaa gttaaccttc | 240 |
| attgattcgg tccaaagact gggtgtgagt taccgattca ccaaagagat cgaagatgaa | 300 |
| cttgagaaca tctaccataa caacaatgat gccgaaaatg acctctacac tacatctctt | 360 |
| cgatttcgat tactccgaga gcatggattc aatgtttcat gtgaggtatt caacaagttt | 420 |
| aaagacgagc aaggggattt taagtcatca ttgacaagcg atgttcgagg attgttggag | 480 |
| ctttacgaag cttcgtattt gagggttcat ggggaagata tattggatga agcgatttct | 540 |
| ttcactactg accatttaac ccttgcagta gcaactttag aatatccttt gtctgaacat | 600 |
| gtttctcatg ctttgaaaaa atcaatccga agaggcttgc caaggattga ggcaaggcac | 660 |
| tatctttcag tataccaaga tattgaatcc cacaatacgg ctttgttgga gtttgctaag | 720 |
| atcgatttca acatgttaca acttttgcat aggaaagagc taagtgagaa ttgtagtggt | 780 |
| ggaaggattt agacttcaaa agaaagttgc catatgtaag agacagagtg gttgaatgtt | 840 |
| ttttttggat cctgggagtg tactttgagc cccaatattc acttggtaga agatatttga | 900 |
| caaaagtgat agctatgact tctgttatag atgatacata tgactcatat gcaacatatg | 960 |
| atgagcttat tccatataca aatgcaattg agaggtggga tatcaaatgc atagaccaac | 1020 |
| ttccagaata catgaaactg agctacaagg cattattaga tgtttatgaa gaaatggaac | 1080 |
| aactgatggc tgaggatgga agacaatatc gtgtagaata tgccaaaaat ataatgatac | 1140 |
| aacttgctca agctttcctt atggaggcca aatggactct tcaaaaccac aaaccatcat | 1200 |
| tcgaggagtt taaggctact gcattgcaaa ctactggtta tgccatgctt gctattacag | 1260 |
| ctttagttga catgggagat attgtaacac cagagacctt tacatgggct gctaataacc | 1320 |
| ctaagatcat tcaagcttct acaattattt gtaggtttat ggacgatgtt gctgagcaca | 1380 |
| agttcaagca gaggagagaa gatgatttct cgggaattga gtgttacatg aagaatatg | 1440 |
| gcgtaatggt acaagaagca tacaatgtgt tttacaagca tatcgagagt gcctggaagg | 1500 |
| atgtgaataa agggtttttg aaaccaaccg aaatgccaat agaagttttg aatcgtatac | 1560 |
| taaatcttgc aagggtgatg aatgtgcttt acaacgaagg tgatggctat acatatgttg | 1620 |
| ggaaagcaac taagggtatt atcagcatat tgctcattga accggtcact ctttgaaa | 1678 |

<210> SEQ ID NO 21
<211> LENGTH: 1687
<212> TYPE: DNA
<213> ORGANISM: Gossypium arboreum

<400> SEQUENCE: 21

```
aacacatcct agaaaatggc ttcacaagct tctcaagttc ttgcttcacc ccatcccgcc      60
atttcatccg aaaatcgacc caaggctgat tttcatcccg gtatttgggg tgatatgttc     120
atcatctgtc ctgatacgga tatcgatgct gcaactgaat tacaatatga agaattaaaa     180
gcacaagtga ggaagatgat tatggaacct gttgatgatt caaaccaaaa gttgcccttc     240
attgatgctg ttcaaagatt aggtgtgagt tatcattttg agaaagagat tgaagatgaa     300
ctagagaata tttaccgtga caccaacaac aatgatgcgg acaccgatct ctacactaca     360
gctcttcgat tccggttact tagagagcat ggcttcgata tttcttgtga tgcattcaac     420
aagttcaaag atgaggcagg gaacttcaag gcatcattga caagtgatgt gcaagggttg     480
ttggaacttt atgaagcttc ctatatgagg gtccatgggg aagatatact cgatgaagcc     540
atttctttca ccactgctca acttacactt gctctaccaa cttttacacca tcctttatcg     600
gaacaggtcg gccatgcctt aaagcagtct atccgaaggg gcttgccaag ggttgaggcc     660
cggaatttca tttcgatata caagatttta gaatcccata caaatcgtt gcttcaattt     720
gcaaagattg atttcaactt gttgcagctt ttgcatagga agagctaag tgagatctgc     780
aggtggtgga agatttaga cttttacaaga aaactaccat ttgcaagaga tagagtggtt     840
gaaggctatt tttggataat gggagtttac tttgaacccc aatactctct tggtagaaag     900
atgttgacaa aagtcatagc aatggcttcc attgttgatg atacttatga ttcatatgca     960
acctatgatg aactcattcc ctatacaaat gcaattgaaa ggtgggatat aaatgcatg    1020
aaccaactcc cgaattacat gaaaataagc tacaaggcac tattaaatgt ttatgaagaa    1080
atggaacagc tgttggcaaa tcaagggaga cagtaccgag ttgagtatgc gaaaaaggcg    1140
atgatacgtc ttgttcaagc ttacctttg gaggccaaat ggactcatca aaattataaa    1200
ccaacctttg aggaatttag agataatgca ttgccaacct ctggctatgc catgcttgct    1260
ataacggcgt ttgtcggcat gggcgaagtt ataaccctg agaccttcaa atgggccgcc    1320
agtgacccca agatcattaa ggcttccacc attatttgca ggttcatgga cgatattgct    1380
gaacataagt tcaaccatag gagagaagac gattgctcag caatcgaatg ttacatgaaa    1440
caatatgggg tgacagcgca ggaagcatac aatgaattca caaacacat tgagagttca    1500
tggaaagatg taaatgaaga gttcttgaaa ccgacagaaa tgccgacacc cgttctttgt    1560
cgtagcctca accttgctag ggttatggat gtacttaca gagaaggtga tggttataca    1620
catgttggga aagctgctaa aggtgggatc acttcattat tgattgatcc aatacaaatt    1680
tgaaaatt                                                             1687
```

<210> SEQ ID NO 22
<211> LENGTH: 1933
<212> TYPE: DNA
<213> ORGANISM: Gossypium arboreum
<400> SEQUENCE: 22

```
ccacttcgca gcaatattat tgcagttcct ggttggctac ctctgagttt tcaacttaaa      60
atttcttggt tttcctcaag aaggaagaag atgttgcaaa tagctttcag ctcgtattca     120
tggctgttga ctgctagcaa ccagaaagat ggaatgttgt tcccagtagc tttgtcattt     180
ttggtagcca tattgggaat ttcactgtgg cacgtatgga ccataaggaa gccaaagaaa     240
gacatcgccc cattaccgcc gggtcccgt gggttgccaa tagtgggata tcttccatat     300
cttggaactg ataatcttca cttggtgttt acagatttgg ctgcagctta cggtcccatc     360
```

-continued

```
tacaagcttt ggctaggaaa caaattatgc gtagtcatta gctcggcacc actggcgaaa      420
gaagtggttc gtgacaacga catcacattt tctgaaaggg atcctcccgt ttgtgcaaag      480
attattacct ttggcctcaa tgatattgta tttgattctt acagtagtcc agattggaga      540
atgaagagaa aagtgctggt acgtgaaatg cttagccata gtagcattaa agcttgttat      600
ggtctaagga gggaacaagt gcttaaaggc gtacaaaatg ttgctcaaag tgctggcaag      660
ccaattgatt ttggtgaaac ggcatttta acatcaatca atgcgatgat gagcatgctg       720
tggggtggca aacagggagg agagcggaaa ggggccgacg tttggggcca atttcgagat      780
ctcataaccg aactaatggt gatacttgga aaaccaaacg tttctgatat tttcccggtg      840
cttgcaaggt ttgacataca gggattggag aaggaaatga ctaaaatcgt taattctttc      900
gataagcttt tcaactccat gattgaagaa agagagaact ttagcaacaa attgagcaaa      960
gaagatggaa acactgaaac aaaagacttc ttgcagcttc tgttggacct caagcagaag     1020
aacgatagcg gaatatcgat aacaatgaat caagtcaagg ccttgctcat ggacattgtg     1080
gtcggtggaa ctgatacaac atcaaccatg atggaatgga caatggctga actaattgca     1140
aatcctgaag caatgaaaaa ggtgaagcaa gaaatagacg atgttgtcgg ttcggatggc     1200
gccgtcgatg agactcactt gcctaagttg cgctatctag atgctgcagt aaaggagacc     1260
ttccgattgc acccaccgat gccactcctt gtaccccgtt gcccgggcga ctcaagcaac     1320
gttggtggct atagcgtacc aaagggcacc agggtcttct taaacatttg gtgtattcag     1380
agggatccac agctttggga aaatccttta gaattcaagc ctgagaggtt cttgactgat     1440
catgagaagc tcgattattt aggaaacgat tcccggtaca tgccgtttgg ttctggaagg     1500
agaatgtgtg ccggagtatc tctcggtgaa aagatgttgt attcctcctt ggcagcaatg     1560
atccatgctt atgattggaa cttggccgac ggtgaagaaa atgacttgat tggcttattt     1620
ggaattatta tgaagaaaaa gaagccttta attcttgttc ctacaccaag accatcaaat     1680
ctccagcact atatgaagta actttactat tgtatttctt ttataccact ttattgcctc     1740
tttgtcatgt ttaggcaaca attctaagta ataagtttgg ctatatggtg aacaataatg     1800
tgtttattat acatcataag caatgagctc ttcccgaccc tagggcaata caatgatact     1860
gtgtattaag tgaaatcaac aaatctttta ttctaaaaaa aaaaaaaaaa aaaaaaaaa      1920 aaaaaaaaaa aaa                                                         1933
```

COTTON PLANT WITH SEED-SPECIFIC REDUCTION IN GOSSYPOL

CROSS REFERENCE TO RELATED APPLICATIONS

This application is a continuation of U.S. application Ser. No. 11/707,760, filed Feb. 16, 2007 now U.S. Pat. No. 7,999,148, which application claims the benefit of U.S. Provisional Patent Application Ser. No. 60/773,893, filed Feb. 16, 2006, the disclosures of which are incorporated herein by reference in their entireties.

TECHNICAL FIELD

The presently disclosed subject matter generally relates to modification of gene expression in plants, and more particularly to selective or tissue-specific reduction of gossypol levels in cotton. Still more particularly, the presently disclosed subject matter pertains to seed-specific reduction of gossypol levels in cottonseed.

BACKGROUND

Cotton has been cultivated for its fiber for over 7000 years. Despite the availability of synthetic alternatives, it continues to serve as the most important source of fiber for textiles. Cotton is grown in more than eighty countries and is a cash crop for more than 20 million farmers in developing countries in Asia and Africa where malnutrition and starvation are rampant (De Onis et al., 1993). An attribute of cotton not widely recognized is that for every 1 kilogram (kg) of fiber, the plant produces approximately 1.65 kg of seed. This makes cotton the third largest field crop in terms of edible oilseed tonnage in the world. However, the ability to utilize the seed and oil is hampered by the presence of a toxic terpenoid, gossypol. The presence of gossypol, a cardio- and hepatotoxic terpenoid unique to the tribe Gossypieae, in the seed glands renders cottonseed unsafe for human and monogastric animal consumption (Risco & Chase Jr., 1997).

A major portion of this abundant agricultural resource is utilized as feed for ruminant animals either as whole seeds or as meal following oil extraction; however, if consumed in sufficient amounts, cottonseed diminishes the reproductive performance of bulls (Chenoweth et al., 1994). During the processing of cottonseed, which involves moist heating, a double bond is formed between the ε-amino group of lysine and the aldehyde group in gossypol. Although bound gossypol is less toxic, the bioavailability of soluble protein and lysine in the meal is reduced. Additional chemical processing steps are needed to remove gossypol to make the oil fit for human use. Consumption of improperly refined oil has been known to cause sterility in men.

Cottonseed also contains 22.5% protein by weight of relatively high quality. The 44 million metric tons (MT) of cottonseed produced each year could provide the total protein requirements of half a billion people per year (50 g/day rate–9.4 million MT of available protein) if the seed were safe for human consumption. However, it is woefully underutilized because of the presence of toxic gossypol within seed glands (Lusas & Jividen, 1987). Thus, gossypol-free cottonseed represents an enormous source of protein that could significantly contribute to human nutrition and health particularly in developing countries (Bressani, 1965; Lambou et al., 1966; Alford et al., 1996) and help society meet the requirements of the predicted 50% increase in the world population in the next 50 years.

Gossypol and related terpenoids are also present throughout the cotton plant in the glands of bolls and foliage, and in roots. In addition, these terpenoids are also induced in response to microbial infections. These compounds protect the plant from both insects and pathogens (Hedin et al., 1992; Stipanovic et al., 1999). Elimination of gossypol from cottonseed has been a long-standing goal of geneticists. Attempts were made in the 1950s to meet this objective by developing so-called "glandless cotton" via conventional breeding techniques (McMichael, 1954; McMichael, 1959; McMichael, 1960; Miravalle & Hyer, 1962; Lusas & Jividen, 1987). Following the discovery of a glandless mutant (McMichael, 1954), several breeding programs were launched in the United States of America, Africa, and Asia to transfer the glandless trait into commercial varieties to produce gossypol-free cottonseed (McMichael, 1959; McMichael, 1960; Miravalle & Hyer, 1962; Lusas & Jividen, 1987). These programs provided cottonseed that could be fed to the more efficient feed-utilizing, monogastric animals and was even deemed safe for human consumption. However, these cotton varieties were a commercial disaster. Under field conditions, glandless plants were extraordinarily susceptible to attack by a host of insect pests because they constitutively lacked protective terpenoids (Bottger et al., 1964; Jenkins et al., 1966) and therefore, were rejected by the farmers.

During the last decade, a number of attempts have been made to utilize antisense technology to eliminate gossypol from cottonseed. However, these attempts have either been unsuccessful (Townsend et al., 2005), have resulted in a small reduction in seed gossypol, or have provided ambiguous results (Martin et al., 2003; Benedict et al., 2004). Despite the advances that have been made toward eliminating gossypol from cottonseed, the production of sufficiently useful products has remained elusive and the potential of cottonseed in contributing to human nutrition has remained unfulfilled.

SUMMARY

In accordance with some embodiments of the presently disclosed subject matter, a cotton plant with a significant seed-specific reduction in gossypol is provided. In some embodiments, a safer cottonseed by tissue-specific reduction of toxic gossypol through disruption of terpenoid biosynthesis is provided. In some embodiments, gossypol in the cottonseed is reduced to a safe level of less than about 0.02% that seen in non-transgenic seeds without affecting the levels of gossypol and other beneficial terpenoids in the foliage where these compounds play a protective role against certain insects.

In accordance with some embodiments, a cotton plant is provided that produces seeds with very low levels of toxic gossypol; however, it maintains normal levels of gossypol and related terpenoids in the foliage. The reduced gossypol cottonseed is a product that contains less than 0.02% of the levels of gossypol found in the parental, wild type seeds. Upon germination, however, this seed develops into a plant containing normal, wild type levels of gossypol and related terpenoids that provide protection against insect pests and diseases in the foliage.

An advantage of some embodiments of the presently disclosed subject matter is that gossypol levels are reduced only in the seeds and not in the foliage of the cotton plant.

In some embodiments, methods are provided that employ a seed-specific promoter in conjunction with RNAi silencing technology to selectively reduce gossypol in the seed without affecting the levels of gossypol and related terpenoids in the foliage and other plant tissues, where these compounds are involved in providing resistance to certain insect pests and diseases (for example, leaves, bracts, buds, bolls, and roots). Advantageously, in some embodiments, the low-gossypol trait is limited to the seeds.

The presently disclosed subject matter thus provides methods for reducing the level of gossypol in a seed of a cotton plant. In some embodiments, the methods comprise expressing in the seed a heterologous nucleic acid construct encoding a δ-cadinene synthase gene trigger sequence or a δ-cadinene-8-hydroxylase trigger sequence, wherein the expressing induces RNA interference (RNAi) in the seed, whereby the level of gossypol in the seed is reduced. In some embodiments, the construct comprises a seed-specific promoter DNA sequence operably linked to the δ-cadinene synthase gene trigger sequence or the δ-cadinene-8-hydroxylase trigger sequence, whereby the RNA interference is selectively induced in the seed and is substantially absent in other tissues of the cotton plant. In some embodiments, a level of gossypol in a tissue selected from the group consisting of foliage, leaves, bracts, buds, bolls, and roots of the treated cotton plant is substantially identical to the level of gossypol in a same tissue of an untreated cotton plant. In some embodiments, the level of at least one terpenoid other than gossypol in a tissue selected from the group consisting of foliage, leaves, bracts, buds, bolls, and roots of the treated cotton plant is substantially identical to the level of the same at least one terpenoid in the same tissue of an untreated cotton plant. In some embodiments, the level of gossypol in the seed is reduced to less than 600 ppm. In some embodiments, the level of gossypol in the seed is reduced to less than 0.02% by weight of the seed compared to a level of gossypol in a seed of an untreated cotton plant. In some embodiments, the δ-cadinene synthase gene trigger sequence comprises at least 15 consecutive nucleotides of any of SEQ ID NOs: 1 and 13-21 or the reverse complement thereof. In some embodiments, the δ-cadinene-8-hydroxylase gene trigger sequence comprises at least 15 consecutive nucleotides of SEQ ID NOs: 22 or the reverse complement thereof. In some embodiments, the heterologous nucleic acid construct comprises a first nucleotide sequence comprising at least 15 consecutive nucleotides of any of SEQ ID NOs: 1 and 13-22 or the reverse-complement thereof, an intervening sequence, and a second nucleotide sequence comprising the reverse-complement of the first nucleotide sequence, and further wherein transcription of the transgene produces a hairpin RNA molecule comprising (a) a double stranded region comprising an intermolecular hybridization of the first and second nucleotide sequences; and (b) a single stranded region comprising at least a part of the intervening sequence.

The presently disclosed subject matter also provides methods for producing a transgenic cotton plant bearing seed with a reduced gossypol content. In some embodiments, the methods comprise (a) stably transforming a host cotton plant cell with an expression construct comprising a seed-specific promoter sequence operably linked to a trigger sequence selected from the group consisting of a δ-cadinene synthase gene trigger sequence and a δ-cadinene-8-hydroxylase gene trigger sequence; (b) regenerating a transgenic plant from the stably transformed host cotton plant cell; and (c) growing the transgenic plant under conditions whereby seed that express the expression construct are produced, wherein the seed have a reduced gossypol content that is lower than that of a similarly situated non-transgenic cotton plant. In some embodiments, the seed-specific promoter sequence comprises a nucleotide sequence as set forth in one of SEQ ID NOs: 10-12. In some embodiments, transcription of the trigger sequence produces a hairpin structure that comprises a double-stranded region comprising a subsequence of an δ-cadinene synthase RNA or an δ-cadinene-8-hydroxylase RNA. In some embodiments, expression of the trigger sequence disrupts cadinane sesquiterpenoid biosynthesis in the seed to a greater extent than it does in the foliage of the plant. In some embodiments, the trigger sequence comprises at least 15 consecutive nucleotides of any of SEQ ID NOs: 1 and 13-22 or the reverse-complement thereof.

The presently disclosed subject matter also provides methods for reducing a level of gossypol in cottonseed. In some embodiments, the methods comprise selectively inducing RNA gene silencing in a seed of a cotton plant to interfere with expression of a target gene selected from the group consisting of a δ-cadinene synthase gene and a δ-cadinene-8-hydroxylase gene in the seed of the cotton plant without a significant reduction of expression of the target gene in the foliage of the plant. In some embodiments, the cotton plant is a transgenic cotton plant. In some embodiments, the transgenic cotton plant has a genome comprising at least one δ-cadinene synthase gene trigger sequence operably linked to a seed-specific promoter DNA sequence, and further wherein the trigger sequence is able to induce RNA gene silencing when expressed in the cottonseed of the plant. In some embodiments, the δ-cadinene synthase gene trigger sequence is selected from the group consisting of (a) SEQ ID NO: 1; (b) a nucleotide sequence at least 95% identical to SEQ ID NO: 1; and (c) a nucleotide sequence comprising a subsequence that is at least 95% identical to 20 consecutive nucleotides of one of SEQ ID NOs: 1 and 13-21. In some embodiments, the transgenic cotton plant has a genome comprising at least one δ-cadinene-8-hydroxylase gene trigger sequence operably linked to a seed-specific promoter DNA sequence, and further wherein the trigger sequence is able to induce RNA gene silencing when expressed in the cottonseed of the plant. In some embodiments, the δ-cadinene-8-hydroxylase gene trigger sequence is selected from the group consisting of (a) SEQ ID NO: 22; (b) a nucleotide sequence at least 95% identical to SEQ ID NO: 22; and (c) a nucleotide sequence comprising a subsequence that is at least 95% identical to 20 consecutive nucleotides of SEQ ID NO: 22. In some embodiments, the level of gossypol in cottonseed is less than 600 ppm. In some embodiments, the level of gossypol is reduced to less than 0.02% by weight of cottonseed compared to the level of gossypol in seed of a cotton plant that is not treated. In some embodiments, a level of a terpenoid in the foliage of the transgenic cotton plant is not significantly reduced as compared to a level of a terpenoid in the foliage of a cotton plant that is not treated.

The presently disclosed subject matter also provides methods for producing a cotton plant bearing low-gossypol seed. In some embodiments, the methods comprising transforming a host cotton plant cell with a DNA construct comprising, as operably linked components, a seed-specific promoter and a trigger sequence targeted to a gene involved in gossypol biosynthesis, whereby the trigger sequence is expressed in the plant cell; regenerating a plant from the transformed plant cell; and growing the plant under conditions whereby seed are produced, wherein the seed have a gossypol content lower than that of cottonseed of a wild type plant. In some embodiments, the seed-specific promoter is an α-globulin promoter. In some embodiments, the DNA construct comprises, as operably linked components, a seed-specific promoter, and a DNA sequence encoding an intron-containing hairpin transformation construct comprising a δ-cadinene synthase gene trigger sequence. In some embodiments, the δ-cadinene synthase gene trigger sequence comprises one of SEQ ID NOs: 1 and 13-21, or a nucleotide sequence comprising at least 15 consecutive nucleotides of one of SEQ ID NOs: 1 and 13-21. In some embodiments, the DNA construct comprises, as operably linked components, a seed-specific promoter, and a DNA sequence encoding an intron-containing hairpin transformation construct comprising a δ-cadinene-8-hydroxylase gene trigger sequence. In some embodiments, the δ-cadinene-8-hydroxylase gene trigger sequence comprises SEQ ID NO: 22 or a nucleotide sequence comprising at least 15 consecutive nucleotides of SEQ ID NO: 22. In some embodiments, expression of the trigger sequence disrupts cadinane sesquiterpenoid biosynthesis in the seed to a greater extent than in the foliage of the plant. In some embodiments, the DNA construct becomes integrated into a genome of the plant cell and the trigger sequence is expressed in the plant cell.

The presently disclosed subject matter also provides expression constructs that can be employed in the disclosed methods. In some embodiments, the expression cassette comprises (a) a seed-specific promoter; (b) a trigger sequence selected from the group consisting of a δ-cadinene synthase gene trigger sequence and a δ-cadinene-8-hydroxylase gene trigger sequence; (c) an intervening sequence; and (d) a sequence comprising a reverse-complement of the trigger sequence, wherein elements (a)-(d) are positioned in relation to each other such that expression of the expression construct in a cottonseed is capable of inducing RNA interference in the cottonseed to reduce gossypol production in the cotton seed. In some embodiments, the seed-specific promoter comprises an α-globulin B gene promoter. In some embodiments, the intervening sequence comprises an intron.

The presently disclosed subject matter also provides vectors for transforming host cotton plant cells. In some embodiments, the vector is a binary *Agrobacterium tumefactions* vector. In some embodiments, a T-DNA region of the binary *Agrobacterium tumefactions* vector comprises a seed-specific promoter operably linked to a DNA sequence encoding an intron-containing hairpin transformation cassette comprising a trigger sequence selected from the group consisting of a δ-cadinene synthase gene trigger sequence and a δ-cadinene-8-hydroxylase gene trigger sequence. In some embodiments, the seed-specific promoter comprises an α-globulin B gene promoter. In some embodiments, the α-globulin B gene promoter comprises SEQ ID NO: 10 or a functional fragment thereof. In some embodiments, the trigger sequence comprises at least 15 consecutive nucleotides of any of SEQ ID NOs: 1 and 13-22. In some embodiments, the δ-cadinene synthase trigger sequence is selected from the group consisting of (a) SEQ ID NO: 1; (b) a nucleotide sequence at least 95% identical to SEQ ID NO: 1; and (c) a nucleotide sequence comprising a subsequence that is at least 95% identical to 20 consecutive nucleotides of one of SEQ ID NOs: 1 and 13-21. In some embodiments, the δ-cadinene-8-hydroxylase trigger sequence is selected from the group consisting of (a) SEQ ID NO: 22; (b) a nucleotide sequence at least 95% identical to SEQ ID NO: 22; and (c) a nucleotide sequence comprising a subsequence that is at least 95% identical to 20 consecutive nucleotides of SEQ ID NO: 22. In some embodiments, the T-DNA region comprises nucleotide sequences encoding a cotton α-globulin B gene promoter; a first nucleotide sequence comprising a trigger sequence selected from the group consisting of a δ-cadinene synthase gene trigger sequence and a δ-cadinene-8-hydroxylase gene trigger sequence; an intervening sequence; and a second nucleotide sequence that comprises at least 15 consecutive nucleotides that can hybridize intramolecularly to at least 15 consecutive nucleotides of the trigger sequence. In some embodiments, the T-DNA region further comprises a transcription terminator selected from the group consisting of an octopine synthase terminator and a nopaline synthase terminator. In some embodiments, the T-DNA region further comprises a selectable marker operably linked to a promoter that is active in a cotton cell.

In some embodiments of the binary *Agrobacterium tumefactions* vector disclosed herein, the T-DNA region comprises (i) a cotton α-globulin B gene promoter; (ii) a first nucleotide sequence comprising a trigger sequence selected from the group consisting of a δ-cadinene synthase gene trigger sequence and a δ-cadinene-8-hydroxylase gene trigger sequence; (iii) an intervening sequence; (iv) a second nucleotide sequence that comprises at least 15 consecutive nucleotides that can hybridize intramolecularly to at least 15 consecutive nucleotides of the trigger sequence; and (v) an octopine synthase terminator, wherein elements (i)-(v) are operably linked. In some embodiments, the first nucleotide sequence comprises at least 15 consecutive nucleotides of any of SEQ ID NOs: 1 and 13-22 or the reverse complement thereof, and the second nucleotide sequence comprises a stretch of at least 15 consecutive nucleotides that is the reverse-complement of at least 15 consecutive nucleotides of the first nucleotide sequence. In some embodiments, the T-DNA region further comprises (vi) a nopaline synthase promoter; (vii) a neomycin phosphotransferase II coding sequence; and (viii) a nopaline synthase terminator, wherein elements (vi)-(viii) are operably linked.

The presently disclosed subject matter also provides transgenic cotton cells comprising the disclosed expression cassettes, transgenic cotton cells comprising the disclosed binary *Agrobacterium tumefactions* vectors, transgenic cotton plants comprising a plurality of the disclosed transgenic cells, transgenic cotton plants produced by the presently disclosed methods, progeny thereof, and transgenic seeds thereof.

The presently disclosed subject matter also provides cotton plants having a seed-specific reduction in gossypol and having wild type gossypol levels in foliage. In some embodiments, the gossypol in the cottonseed is reduced to a level of less than about 0.02% that seen in wild type seeds. In some embodiments, the presently disclosed subject matter provides seeds from the presently disclosed plants.

The presently disclosed subject matter also provides kits comprising the presently disclosed expression cassettes or the presently disclosed binary *Agrobacterium tumefactions* vectors and at least one reagent for introducing the presently disclosed expression cassettes or the presently disclosed binary *Agrobacterium tumefactions* vector into a plant cell. In some embodiments, the presently disclosed kits further comprise instructions for introducing the presently disclosed expression cassettes or the presently disclosed binary *Agrobacterium tumefactions* vectors into a plant cell.

It is an object of the presently disclosed subject matter to provide methods and compositions for selective or tissue-specific reduction of gossypol levels in cotton.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIG. 2 presents a nucleotide sequence of a 604 basepair (bp) internal fragment of a δ-cadinene synthase gene product that was used as an exemplary trigger sequence in an ihpRNA vector. The 604 bp sequence depicted in FIG. 2 corresponds to SEQ ID NO: 1.

FIG. 5A is a series of bar graphs showing gossypol levels in 10 individual seeds each from wild type control plants (black bars) and two independent RNAi transgenic lines, LCT66-2 (light gray bars) and LCT66-32 (white bars). The results from PCR analysis on DNA from the same individual seeds from RNAi lines are depicted under the graphs corresponding to the transgenic lines. Note that the gossypol levels in the null segregant seeds (dark gray bars) are similar to control values. Mean (±s.e.m.) gossypol values for the control seeds (n=10) and the transgene bearing seeds (n=8) from each of the transgenic lines are shown with the respective graphs. *The value for the transgenic line is significantly different from wild type control value at P<0 001.

FIG. 5B is a set of photomicrographs and chromatographs of sections of four mature $T_1$ seeds obtained from the transgenic line LCT66-32 (left panel). The seed at the top was a null segregant while the others were transgenic seeds. HPLC chromatograms (right panel) show the gossypol levels in the extracts from the same four seeds. Y-axis: absorbance at 272 nm and X-axis: elution time (min). Note the correlation between visible phenotype and the gossypol levels in the seed.

FIG. 7 is a set of autoradiographs depicting the results of Southern hybridization analyses on three low-seed-gossypol lines (LCT66-2, LCT66-32, and LCT66-81) used for various studies in this investigation. Genomic DNA (15 μg) was digested with EcoRI, and the blots were probed with either an nptII gene sequence (left) or an OCS terminator sequence (right). Because the low-seed-gossypol phenotype and PCR results for lines #LCT66-2 and LCT66-32 showed a strict 3:1 segregation, it is believed that the transgene copies were integrated at a single locus.

Figure 1:
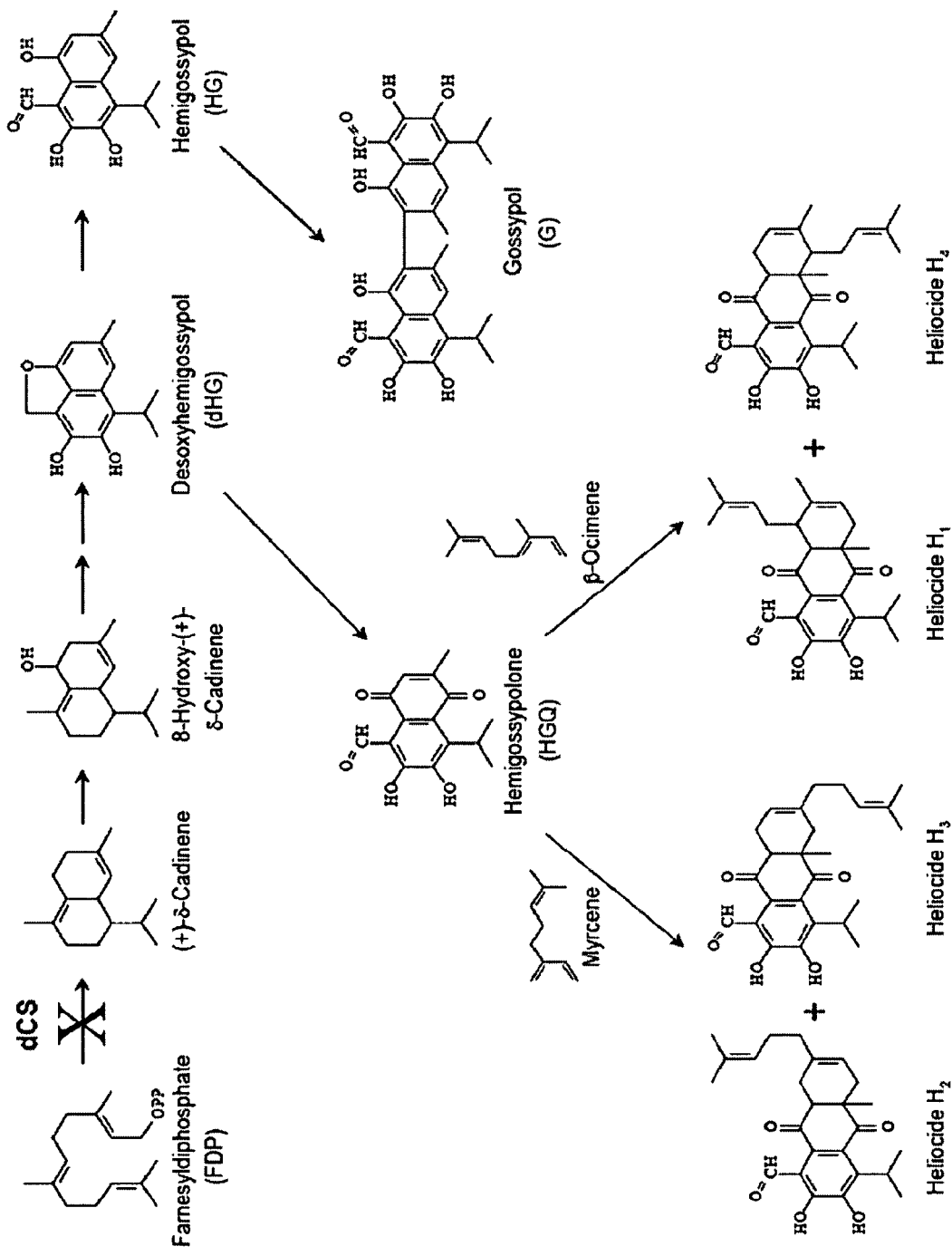
FIG. 1 is a schematic diagram depicting a proposed biosynthetic pathway to the syntheses of gossypol and other terpenoids in cotton plants. Chemical structures of certain terpenoids are also depicted.

Gossypol level in a pooled sample of 30 T$_2$ seeds obtained from a homozygous T$_1$ plant derived from a particular transgenic line.

FIG. 13 is a nucleic acid sequence alignment of various δ-cadinene synthase gene sequences from diploid and tetraploid cottons (see Table 1). The references at the left of each line refer to GENBANK® Accession Nos. and correspond to SEQ ID NOs: 13-21 as set forth in more detail hereinbelow. The asterisks below each grouping indicate positions where all nine sequences have the same nucleotide.

BRIEF DESCRIPTION OF THE SEQUENCE LISTING

SEQ ID NO: 1 is a nucleotide sequence of a 604 bp long internal fragment from a δ-cadinene synthase C subfamily cDNA clone from *Gossypium hirsutum* that was employed as a trigger sequence for modulating δ-cadinene synthase activity in cotton plants.

SEQ ID NOs: 2 and 3 are the nucleotide sequences of synthetic primers that can be employed together in the polymerase chain reaction (PCR) to amplify a 580 bp subsequence of the trigger region.

SEQ ID NOs: 4 and 5 are the nucleotide sequences of synthetic primers that can be employed together in the polymerase chain reaction (PCR) to amplify a 412 bp subsequence of the *Gossypium* histone 3 gene corresponding to nucleotides 115-526 of GENBANK® Accession No. AF024716.

SEQ ID NOs: 6 and 7 are the nucleotide sequences of synthetic primers that can be employed together in the polymerase chain reaction (PCR) to amplify a 416 bp subsequence from the 3'-end of the cDNA clone isolated in inventor's laboratory. These primers also amplify a 412 bp fragment of a *Gossypium arboreum* δ-cadinene synthase gene corresponding to nucleotides 1449-1860 of GENBANK® Accession No. U23205.

SEQ ID NOs: 8 and 9 are the nucleotide sequences of synthetic primers that can be employed together in the polymerase chain reaction (PCR) to amplify a 653-bp fragment from genomic DNA from plants carrying a pAGP-iHP-dCS transgene.

SEQ ID NO: 10 is the nucleotide sequence of an 1144 bp promoter fragment isolated from *Gossypium hirsutum*. This sequence corresponds to SEQ ID NO: 1 of PCT International Patent Application Publication No. WO 2003/052111, for which a U.S. National Stage Application was published as U.S. Patent Application Publication No. 2003/154516. The disclosure of each of these Patent Application Publications is incorporated herein in its entirety.

SEQ ID NO: 11 is the nucleotide sequence of an 1108 bp promoter fragment isolated from *Gossypium hirsutum*. This sequence corresponds to SEQ ID NO: 2 of PCT International Patent Application Publication No. WO 2003/052111.

SEQ ID NO: 12 is the nucleotide sequence of a 336 bp promoter fragment isolated from *Gossypium hirsutum*. This sequence corresponds to SEQ ID NO: 3 of PCT International Patent Application Publication No. WO 2003/052111.

SEQ ID NO: 13 is a nucleotide sequence of the subsequence of a *Gossypium arboreum* Cad1-C14 (XC14) gene sequence presented in FIG. 13. It corresponds to nucleotides 60-1740 of GENBANK® Accession No. U23205.

SEQ ID NO: 14 is a nucleotide sequence of the subsequence of a *Gossypium hirsutum* Cdn1-C4 gene sequence presented in FIG. 13. It corresponds to nucleotides 1-1660 of GENBANK® Accession No. AF270425.

SEQ ID NO: 15 is a nucleotide sequence of the subsequence of a *Gossypium hirsutum* Cdn1 gene sequence presented in FIG. 13. It corresponds to nucleotides 18-1698 of GENBANK® Accession No. U88318.

SEQ ID NO: 16 is a nucleotide sequence of the subsequence of a *Gossypium arboreum* Cad1-C2 gene sequence presented in FIG. 13. It corresponds to nucleotides 49-1729 of GENBANK® Accession No. Y16432.

SEQ ID NO: 17 is a nucleotide sequence of the subsequence of a *Gossypium arboreum* Cad1-C3 gene sequence presented in FIG. 13. It corresponds to nucleotides 699-836, 935-1199, 1301-1673, 2008-2225, 2335-2475, 2640-1890, and 3195-3492 of GENBANK® Accession No. AF174294.

SEQ ID NO: 18 is a nucleotide sequence of the subsequence of a *Gossypium arboreum* Cad1-C1 (XC1) gene sequence presented in FIG. 13. It corresponds to nucleotides 60-1348 and 1436-1740 of GENBANK® Accession No. U23206.

SEQ ID NO: 19 is a nucleotide sequence of the subsequence of a *Gossypium arboreum* Cad1-B gene sequence presented in FIG. 13. It corresponds to nucleotides 146-1576, 1677-1943, 2045-2418, 2741-2956, 3063-3201, 3367-3613, and 3900-4195 of GENBANK® Accession No. X95323.

SEQ ID NO: 20 is a nucleotide sequence of the subsequence of a *Gossypium hirsutum* Cdn-D1 gene sequence presented in FIG. 13. It corresponds to nucleotides 2069-2206, 2315-2579, 2681-3053, 3400-3618, 2697-3835, 4037-4285, and 4559-4854 of GENBANK® Accession No. AY800107.

SEQ ID NO: 21 is a nucleotide sequence of the subsequence of a *Gossypium arboreum* Cad1-A gene sequence presented in FIG. 13. It corresponds to nucleotides 82-1768 of GENBANK® Accession No. X96429.

DETAILED DESCRIPTION

Toward fulfilling the promise of cottonseed in contributing to the food requirements of the burgeoning world population, certain embodiments of the presently disclosed subject matter provide a new, low gossypol cottonseed that is engineered for use in human nutrition.

The presently disclosed subject matter relates in some embodiments to the use of RNA interference (RNAi) to disrupt gossypol production in a tissue (for example, seed)-specific manner. Disclosed herein is the discovery that targeted engineering of the gossypol biosynthetic pathway by interfering with the expression of the δ-cadinene synthase gene during seed development resulted in a significant reduction in cottonseed gossypol levels. Results from molecular analyses on developing transgenic embryos were consistent with the observed phenotype in the mature seeds. Importantly, the levels of gossypol and related terpenoids in the foliage, floral parts, and roots were not diminished, and thus remained available for plant defense against insects and diseases. These results illustrated that a single-step, targeted genetic modification applied to an underutilized agricultural byproduct provided a mechanism to open up a new source of nutrition for hundreds of millions of people. Similar approaches can be applied to eliminate toxins from other potential food sources to improve global food security.

Also disclosed herein is the successful use of a seed-specific promoter in conjunction with RNAi to disrupt gossypol biosynthesis only in the seed while retaining a full complement of gossypol and related terpenoids in the rest of the plant for maintaining its defensive capabilities against pests and diseases. In a representative embodiment, a binary plasmid vector was constructed containing a selectable marker gene expression cassette and another cassette to induce seed-specific silencing of delta-cadinene synthase gene family. U.S. Patent Application Publication No. 2003/0154516, filed Dec. 11, 2002 (the disclosure of which is hereby incorporated herein by reference), discloses a cotton α-globulin (also referred to here as alpha-globulin) promoter and methods for seed-specific expression of transgenes and gene silencing constructs.

In a representative embodiment, a silencing cassette was constructed in the following way. An isolated partial 604 bp sequence of the delta-cadinene synthase gene that had homology to published sequences of other homologs of this gene was chosen. This sequence was placed as inverted repeats on either side of an intron spacer, similar to techniques described in Wesley et al., 2001. See also U.S. Pat. No. 6,423,885; and U.S. Pat. No. 7,138,565. This inverted repeat sequence was placed under the control of a seed-specific, alpha-globulin promoter (Sunilkumar et al., 2002) from cotton for expression so that the transcription product forms a hairpin RNA structure that initiates RNAi mechanism to silence some or all members of the delta-cadinene synthase gene family in developing cotton embryos. The binary vector containing the silencing cassette was used to transform cotton using the *Agrobacterium* method (Rathore et al., 2006). Seeds from the transgenic plants were tested for the levels of gossypol and some lines were found to have seeds with significantly low levels of gossypol (<2% by weight of the levels found in parental wild type seeds; i.e., 0.02% by weight in modified seeds vs. 1% by weight in parental wild type seeds). When these low gossypol seeds were germinated, the foliage, floral parts, and roots of the resulting plants were found to have normal, wild type levels of gossypol and related terpenoids. These results demonstrated that cotton plants have been developed that show the reduced gossypol trait only in the seeds. Moreover, the results disclosed herein clearly demonstrate the feasibility of using an RNAi approach in a targeted manner to solve a long-standing problem of cottonseed toxicity and provide a new avenue to exploit the considerable quantities of protein and oil available in the global cottonseed output.

I. DEFINITIONS

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the articles "a", "an", and "the" refer to "one or more" when used in this application, including in the claims. For example, the phrase "a cell" refers to one or more cells. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

As used herein, the term "cell" is used in its usual biological sense. In some embodiments, the cell is present in an organism, for example, a plant including, but not limited to cotton. The cell can be eukaryotic (e.g., a plant cell, such as a cotton cell) or prokaryotic (e.g. a bacterium). The cell can be of somatic or germ line origin, totipotent, pluripotent, or differentiated to any degree, dividing or non-dividing. The cell can also be derived from or can comprise a gamete or embryo, a stem cell, or a fully differentiated cell.

As used herein, the terms "host cells" and "recombinant host cells" are used interchangeably and refer to cells (for example, cotton cells) into which the compositions of the presently disclosed subject matter (for example, an expression vector comprising a δ-cadinene synthase gene trigger sequence) can be introduced. Furthermore, the terms refer not only to the particular plant cell into which an expression construct is initially introduced, but also to the progeny or potential progeny of such a cell. Because certain modifications can occur in succeeding generations due to either mutation or environmental influences, such progeny might not, in fact, be identical to the parent cell, but are still included within the scope of the term as used herein.

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed, in some embodiments, ribonuclease activity. Determination of binding free energies for nucleic acid molecules is well known in the art. See e.g., Freier et al., 1986; Turner et al., 1987.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence.

As used herein, the term "gene" refers to a nucleic acid sequence that encodes an RNA, for example, nucleic acid sequences including, but not limited to, structural genes encoding a polypeptide. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation from one or more existing sequences.

As is understood in the art, a gene typically comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

The phrase "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell can also affect gene expression as defined herein.

However, in the case of genes that do not encode protein products, for example nucleic acid sequences that encode RNAs or precursors thereof that induce RNAi, the term "gene expression" refers to the processes by which the RNA is produced from the nucleic acid sequence. Typically, this process is referred to as transcription, although unlike the transcription of protein-coding genes, the transcription products of an RNAi-inducing RNA (or a precursor thereof) are not translated to produce a protein. Nonetheless, the production of a mature RNAi-inducing RNA from an RNAi-inducing RNA precursor nucleic acid sequence is encompassed by the term "gene expression" as that term is used herein.

The terms "heterologous gene", "heterologous DNA sequence", "heterologous nucleotide sequence", "exogenous nucleic acid molecule", "exogenous DNA segment", and "transgene" as used herein refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

As used herein, the term "isolated" refers to a molecule substantially free of other nucleic acids, proteins, lipids, carbohydrates, and/or other materials with which it is normally associated, such association being either in cellular material or in a synthesis medium. Thus, the term "isolated nucleic acid" refers to a ribonucleic acid molecule or a deoxyribonucleic acid molecule (for example, a genomic DNA, cDNA, mRNA, RNAi-inducing RNA or a precursor thereof, etc.) of natural or synthetic origin or some combination thereof, which (1) is not associated with the cell in which the "isolated nucleic acid" is found in nature, or (2) is operatively linked to a polynucleotide to which it is not linked in nature. Similarly, the term "isolated polypeptide" refers to a polypeptide, in some embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated", when used in the context of an "isolated cell", refers to a cell that has been removed from its natural environment, for example, as a part of an organ, tissue, or organism.

As used herein, the term "modulate" refers to an increase, decrease, or other alteration of any, or all, chemical and biological activities or properties of a biochemical entity, e.g., a wild type or mutant nucleic acid molecule. For example, the term "modulate" can refer to a change in the expression level of a gene or a level of an RNA molecule or equivalent RNA molecules encoding one or more proteins or protein subunits; or to an activity of one or more proteins or protein subunits that is upregulated or downregulated, such that expression, level, or activity is greater than or less than that observed in the absence of the modulator. For example, the term "modulate" can mean "inhibit" or "suppress", but the use of the word "modulate" is not limited to this definition.

As used herein, the terms "inhibit", "suppress", "down regulate", and grammatical variants thereof are used interchangeably and refer to an activity whereby gene expression or a level of an RNA encoding one or more gene products is reduced below that observed in the absence of a nucleic acid molecule of the presently disclosed subject matter. In some embodiments, inhibition with a nucleic acid sequence comprising a trigger sequence results in a decrease in the steady state expression level of a target RNA (e.g., a δ-cadinene synthase RNA). In some embodiments, inhibition with a nucleic acid sequence comprising a trigger sequence results in an expression level of a target gene that is below that level observed in the presence of an inactive or attenuated molecule that is unable to downregulate the expression level of the target. In some embodiments, inhibition of gene expression with a nucleic acid sequence comprising a trigger sequence of the presently disclosed subject matter is greater in the presence of the nucleic acid sequence comprising the trigger sequence molecule than in its absence. In some embodiments, inhibition of gene expression is associated with an enhanced rate of degradation of the mRNA encoded by the gene (for example, by dsRNA-mediated inhibition of gene expression).

The term "naturally occurring", as applied to an object, refers to the fact that an object can be found in nature. For example, a polypeptide or polynucleotide sequence that is present in an organism (including bacteria) that can be isolated from a source in nature and which has not been intentionally modified by man in the laboratory is naturally occurring. It must be understood, however, that any manipulation by the hand of man can render a "naturally occurring" object an "isolated" object as that term is used herein.

As used herein, the terms "nucleic acid" and "nucleic acid molecule" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., α-enantiomeric forms of naturally occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids", which comprise naturally occurring or modified nucleic acid bases attached to a polyamide backbone. Nucleic acids can be either single stranded or double stranded.

The terms "operably linked" and "operatively linked" are used interchangeably. When describing the relationship between two nucleic acid regions, each term refers to a juxtaposition wherein the regions are in a relationship permitting them to function in their intended manner. For example, a control sequence "operably linked" to a coding sequence can be ligated in such a way that expression of the coding sequence is achieved under conditions compatible with the control sequences, such as when the appropriate molecules (e.g., inducers and polymerases) are bound to the control or regulatory sequence(s). Thus, in some embodiments, the phrase "operably linked" refers to a promoter connected to a coding sequence in such a way that the transcription of that coding sequence is controlled and regulated by that promoter. Techniques for operably linking a promoter to a coding sequence are well known in the art; the precise orientation and location relative to a coding sequence of interest is dependent, inter alia, upon the specific nature of the promoter.

Thus, the term "operably linked" can refer to a promoter region that is connected to a nucleotide sequence in such a way that the transcription of that nucleotide sequence is controlled and regulated by that promoter region. Similarly, a nucleotide sequence is said to be under the "transcriptional control" of a promoter to which it is operably linked. Techniques for operably linking a promoter region to a nucleotide sequence are known in the art. In some embodiments, a nucleotide sequence comprises a coding sequence and/or an open reading frame. The term "operably linked" can also refer to a transcription termination sequence that is connected to a nucleotide sequence in such a way that termination of transcription of that nucleotide sequence is controlled by that transcription termination sequence.

The term "operably linked" can also refer to a transcription termination sequence that is connected to a nucleotide sequence in such a way that termination of transcription of that nucleotide sequence is controlled by that transcription termination sequence. In some embodiments, a transcription termination sequence comprises an octopine synthase terminator and in some embodiments a transcription termination sequence comprises a nopaline synthase terminator.

In some embodiments, more than one of these elements can be operably linked in a single molecule. Thus, in some embodiments multiple terminators, coding sequences, and promoters can be operably linked together. Techniques are known to one of ordinary skill in the art that would allow for the generation of nucleic acid molecules that comprise different combinations of coding sequences and/or regulatory elements that would function to allow for the expression of one or more nucleic acid sequences in a cell.

The phrases "percent identity" and "percent identical," in the context of two nucleic acid or protein sequences, refer to two or more sequences or subsequences that have in some embodiments at least 60%, in some embodiments at least 70%, in some embodiments at least 80%, in some embodiments at least 85%, in some embodiments at least 90%, in some embodiments at least 95%, in some embodiments at least 98%, and in some embodiments at least 99% nucleotide or amino acid residue identity, when compared and aligned for maximum correspondence, as measured using one of the following sequence comparison algorithms or by visual inspection. The percent identity exists in some embodiments over a region of the sequences that is at least about 50 residues in length, in some embodiments over a region of at least about 100 residues, and in some embodiments the percent identity exists over at least about 150 residues. In some embodiments, the percent identity exists over the entire length of a given region, such as a coding region.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm described in Smith & Waterman, 1981, by the homology alignment algorithm described in Needleman & Wunsch, 1970, by the search for similarity method described in Pearson & Lipman, 1988, by computerized implementations of these algorithms (GAP, BESTFIT, FASTA, and TFASTA in the GCG® WISCONSIN PACKAGE®, available from Accelrys, Inc., San Diego, Calif., United States of America), or by visual inspection. See generally, Ausubel et al., 1989.

One example of an algorithm that is suitable for determining percent sequence identity and sequence similarity is the BLAST algorithm, which is described in Altschul et al., 1990. Software for performing BLAST analyses is publicly available through the National Center for Biotechnology Information via the World Wide Web. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

As used herein, the terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide", and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8, or 10 amino acids long, at least 14 amino acids long, at least 20, 30, 40, or 50 amino acids long, at least 75 amino acids long, or at least 100, 150, 200, 300, 500, or more amino acids long. A fragment can retain one or more of the biological activities of the reference polypeptide. Further, fragments can include a sub-fragment of a specific region, which sub-fragment retains a function of the region from which it is derived.

As used herein, the term "primer" refers to a sequence comprising in some embodiments two or more deoxyribonucleotides or ribonucleotides, in some embodiments more than three, in some embodiments more than eight, and in some embodiments at least about 20 nucleotides of an exonic or intronic region. Such oligonucleotides are in some embodiments between ten and thirty bases in length.

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements. In some embodiments, a method of the presently disclosed subject matter employs a RNA polymerase III promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the cytomegalovirus (CMV) minimal promoter, the herpes simplex virus thymidine kinase (HSV-tk) minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operatively linked gene. For example, cell-type-specific or tissue-specific transcriptional regulatory elements can be added to minimal promoters to create recombinant promoters that direct transcription of an operatively linked nucleotide sequence in a cell-type-specific or tissue-specific manner.

Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types (in some embodiments, in all cell types) of an organism. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the β-actin promoter (see e.g., Williams et al., 1993), and other constitutive promoters known to those of skill in the art. "Tissue-specific" or "cell-type-specific" promoters, on the other hand, direct transcription in some tissues or cell types of an organism but are inactive in some or all others tissues or cell types. Exemplary tissue-specific promoters include those promoters described in more detail hereinbelow, as well as other tissue-specific and cell-type specific promoters known to those of skill in the art. In some embodiments, a tissue-specific promoter is a seed-specific promoter. In some embodiments, the seed-specific promoter comprises a nucleotide sequence as set forth in one or SEQ ID NOs: 10-12, or a functional fragment thereof.

When used in the context of a promoter, the term "linked" as used herein refers to a physical proximity of promoter elements, such that they function together to direct transcription of an operatively linked nucleotide sequence The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element. In some embodiments, a transcriptional regulatory sequence is a transcription termination sequence, alternatively referred to herein as a transcription termination signal.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species can be purified to essential homogeneity (contaminant species cannot be detected in the composition by conventional detection methods) wherein the composition consists essentially of a single species. A skilled artisan can purify a polypeptide of the presently disclosed subject matter using standard techniques for protein purification in light of the teachings herein. Purity of a polypeptide can be determined by a number of methods known to those of skill in the art, including for example, amino-terminal amino acid sequence analysis, gel electrophoresis, and mass-spectrometry analysis.

A "reference sequence" is a defined sequence used as a basis for a sequence comparison. A reference sequence can be a subset of a larger sequence, for example, as a segment of a full-length nucleotide or amino acid sequence, or can comprise a complete sequence. Generally, when used to refer to a nucleotide sequence, a reference sequence is at least 200, 300, or 400 nucleotides in length, frequently at least 600 nucleotides in length, and often at least 800 nucleotides in length. Because two proteins can each (1) comprise a sequence (i.e., a portion of the complete protein sequence) that is similar between the two proteins, and (2) can further comprise a sequence that is divergent between the two proteins, sequence comparisons between two (or more) proteins are typically performed by comparing sequences of the two proteins over a "comparison window" (defined hereinabove) to identify and compare local regions of sequence similarity.

The term "regulatory sequence" is a generic term used throughout the specification to refer to polynucleotide sequences, such as initiation signals, enhancers, regulators, promoters, and termination sequences, which are necessary or desirable to affect the expression of coding and non-coding sequences to which they are operatively linked. Exemplary regulatory sequences are described in Goeddel, 1990, and include, for example, the early and late promoters of simian virus 40 (SV40), adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nature and use of such control sequences can differ depending upon the host organism. In prokaryotes, such regulatory sequences generally include promoter, ribosomal binding site, and transcription termination sequences. The term "regulatory sequence" is intended to include, at a minimum, components the presence of which can influence expression, and can also include additional components the presence of which is advantageous, for example, leader sequences and fusion partner sequences.

In some embodiments, transcription of a polynucleotide sequence is under the control of a promoter sequence (or other regulatory sequence) that controls the expression of the polynucleotide in a cell-type in which expression is intended. It will also be understood that the polynucleotide can be under the control of regulatory sequences that are the same or different from those sequences which control expression of the naturally occurring form of the polynucleotide. As used herein, the phrase "functional derivative" refers to a subsequence of a promoter or other regulatory element that has substantially the same activity as the full length sequence from which it was derived. As such, a "functional derivative" of a seed-specific promoter can itself function as a seed-specific promoter.

Termination of transcription of a polynucleotide sequence is typically regulated by an operatively linked transcription termination sequence (for example, an RNA polymerase III termination sequence). In certain instances, transcriptional terminators are also responsible for correct mRNA polyadenylation. The 3' non-transcribed regulatory DNA sequence includes from in some embodiments about 50 to about 1,000, and in some embodiments about 100 to about 1,000, nucleotide base pairs and contains plant transcriptional and translational termination sequences. Appropriate transcriptional terminators and those that are known to function in plants include the cauliflower mosaic virus (CaMV) 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, a gamma coixin, oleosin 3, or other terminator from the genus *Coix* can be used.

As used herein, the term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an RNA molecule or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

As used herein, the phrase "double stranded RNA" refers to an RNA molecule at least a part of which is in Watson-Crick base pairing forming a duplex. As such, the term is to be understood to encompass an RNA molecule that is either fully or only partially double stranded. Exemplary double stranded RNAs include, but are not limited to molecules comprising at least two distinct RNA strands that are either partially or fully duplexed by intermolecular hybridization. Additionally, the term is intended to include a single RNA molecule that by intramolecular hybridization can form a double stranded region (for example, a hairpin). Thus, as used herein the phrases "intermolecular hybridization" and "intramolecular hybridization" refer to double stranded molecules for which the nucleotides involved in the duplex formation are present on different molecules or the same molecule, respectively.

As used herein, the phrase "double stranded region" refers to any region of a nucleic acid molecule that is in a double stranded conformation via hydrogen bonding between the nucleotides including, but not limited to hydrogen bonding between cytosine and guanosine, adenosine and thymidine, adenosine and uracil, and any other nucleic acid duplex as would be understood by one of ordinary skill in the art. The length of the double stranded region can vary from about 15 consecutive basepairs to several thousand basepairs. In some embodiments, the double stranded region is at least 15 basepairs, in some embodiments between 15 and 50 basepairs, in some embodiments between 50 and 100 basepairs, in some embodiments between 100 and 500 basepairs, in some embodiments between 500 and 1000 basepairs, and in some embodiments is at least 1000 basepairs. As describe hereinabove, the formation of the double stranded region results from the hybridization of complementary RNA strands (for example, a sense strand and an antisense strand), either via an intermolecular hybridization (i.e., involving 2 or more distinct RNA molecules) or via an intramolecular hybridization, the latter of which can occur when a single RNA molecule contains self-complementary regions that are capable of hybridizing to each other on the same RNA molecule. These self-complementary regions are typically separated by a stretch of nucleotides such that the intramolecular hybridization event forms what is referred to in the art as a "hairpin" or a "stem-loop structure". In some embodiments, the stretch of nucleotides between the self-complementary regions comprises an intron that is excised from the nucleic acid molecule by RNA processing in the cell.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "P-value". Those P-values that fall below a user-defined cutoff point are regarded as significant. In some embodiments, a P-value less than or equal to 0.05, in some embodiments less than 0.01, in some embodiments less than 0.005, and in some embodiments less than 0.001, are regarded as significant.

The term "substantially identical", in the context of two nucleotide sequences, refers to two or more sequences or subsequences that have in some embodiments at least about 70% nucleotide identity, in some embodiments at least about 75% nucleotide identity, in some embodiments at least about 80% nucleotide identity, in some embodiments at least about 85% nucleotide identity, in some embodiments at least about 90% nucleotide identity, in some embodiments at least about 95% nucleotide identity, in some embodiments at least about 97% nucleotide identity, and in some embodiments at least about 99% nucleotide identity, when compared and aligned for maximum correspondence, as measured using one of the following sequence comparison algorithms or by visual inspection. In one example, the substantial identity exists in nucleotide sequences of at least 17 residues, in some embodiments in nucleotide sequence of at least about 18 residues, in some embodiments in nucleotide sequence of at least about 19 residues, in some embodiments in nucleotide sequence of at least about 20 residues, in some embodiments in nucleotide sequence of at least about 21 residues, in some embodiments in nucleotide sequence of at least about 22 residues, in some embodiments in nucleotide sequence of at least about 23 residues, in some embodiments in nucleotide sequence of at least about 24 residues, in some embodiments in nucleotide sequence of at least about 25 residues, in some embodiments in nucleotide sequence of at least about 26 residues, in some embodiments in nucleotide sequence of at least about 27 residues, in some embodiments in nucleotide sequence of at least about 30 residues, in some embodiments in nucleotide sequence of at least about 50 residues, in some embodiments in nucleotide sequence of at least about 75 residues, in some embodiments in nucleotide sequence of at least about 100 residues, in some embodiments in nucleotide sequences of at least about 150 residues, and in yet another example in nucleotide sequences comprising complete coding sequences. In some embodiments, polymorphic sequences can be substantially, identical sequences. The term "polymorphic" refers to the occurrence of two or more genetically determined alternative sequences or alleles in a population. An allelic difference can be as small as one base pair. Nonetheless, one of ordinary skill in the art would recognize that the polymorphic sequences correspond to the same gene.

Another indication that two nucleotide sequences are substantially identical is that the two molecules specifically or substantially hybridize to each other under stringent conditions. In the context of nucleic acid hybridization, two nucleic acid sequences being compared can be designated a "probe sequence" and a "test sequence". A "probe sequence" is a reference nucleic acid molecule, and a "'test sequence" is a test nucleic acid molecule, often found within a heterogeneous population of nucleic acid molecules.

An exemplary nucleotide sequence employed for hybridization studies or assays includes probe sequences that are complementary to or mimic in some embodiments at least an about 14 to 40 nucleotide sequence of a nucleic acid molecule of the presently disclosed subject matter. In one example, probes comprise 14 to 20 nucleotides, or even longer where desired, such as 30, 40, 50, 60, 100, 200, 300, or 500 nucleotides or up to the full length of a given gene. Such fragments can be readily prepared by, for example, directly synthesizing the fragment by chemical synthesis, by application of nucleic acid amplification technology, or by introducing selected sequences into recombinant vectors for recombinant production. The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

By way of non-limiting example, hybridization can be carried out in 5×SSC, 4×SSC, 3×SSC, 2×SSC, 1×SSC, or 0.2×SSC for at least about 1 hour, 2 hours, 5 hours, 12 hours, or 24 hours (see Sambrook & Russell, 2001, for a description of SSC buffer and other hybridization conditions). The temperature of the hybridization can be increased to adjust the stringency of the reaction, for example, from about 25° C. (room temperature), to about 45° C., 50° C., 55° C., 60° C., or 65° C. The hybridization reaction can also include another agent affecting the stringency; for example, hybridization conducted in the presence of 50% formamide increases the stringency of hybridization at a defined temperature.

The hybridization reaction can be followed by a single wash step, or two or more wash steps, which can be at the same or a different salinity and temperature. For example, the temperature of the wash can be increased to adjust the stringency from about 25° C. (room temperature), to about 45° C., 50° C., 55° C., 60° C., 65° C., or higher. The wash step can be conducted in the presence of a detergent, e.g., SDS. For example, hybridization can be followed by two wash steps at 65° C. each for about 20 minutes in 2×SSC, 0.1% SDS, and optionally two additional wash steps at 65° C. each for about 20 minutes in 0.2×SSC, 0.1% SDS.

The following are examples of hybridization and wash conditions that can be used to clone homologous nucleotide sequences that are substantially identical to reference nucleotide sequences of the presently disclosed subject matter: a probe nucleotide sequence hybridizes in one example to a target nucleotide sequence in 7% sodium dodecyl sulfate (SDS), 0.5M $NaPO_4$, 1 mm ethylenediamine tetraacetic acid (EDTA) at 50° C. followed by washing in 2×SSC, 0.1% SDS at 50° C.; in some embodiments, a probe and test sequence hybridize in 7% sodium dodecyl sulfate (SDS), 0.5M $NaPO_4$, 1 mm EDTA at 50° C. followed by washing in 1×SSC, 0.1% SDS at 50° C.; in some embodiments, a probe and test sequence hybridize in 7% sodium dodecyl sulfate (SDS), 0.5M $NaPO_4$, 1 mm EDTA at 50° C. followed by washing in 0.5×SSC, 0.1% SDS at 50° C.; in some embodiments, a probe and test sequence hybridize in 7% sodium dodecyl sulfate (SDS), 0.5M $NaPO_4$, 1 mm EDTA at 50° C. followed by washing in 0.1×SSC, 0.1% SDS at 50° C.; in yet another example, a probe and test sequence hybridize in 7% sodium dodecyl sulfate (SDS), 0.5M $NaPO_4$, 1 mm EDTA at 50° C. followed by washing in 0.1×SSC, 0.1% SDS at 65° C.

Additional exemplary stringent hybridization conditions include overnight hybridization at 42° C. in a solution comprising or consisting of 50% formamide, 10×Denhardt's (0.2% Ficoll, 0.2% polyvinylpyrrolidone, 0.2% bovine serum albumin) and 200 mg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2× SSC, 0.1% SDS.

Hybridization can include hybridizing two nucleic acids in solution, or a nucleic acid in solution to a nucleic acid attached to a solid support, e.g., a filter. When one nucleic acid is on a solid support, a prehybridization step can be conducted prior to hybridization. Prehybridization can be carried out for at least about 1 hour, 3 hours, or 10 hours in the same solution and at the same temperature as the hybridization (but without the complementary polynucleotide strand).

Thus, upon a review of the present disclosure, stringency conditions are known to those skilled in the art or can be determined experimentally by the skilled artisan. See e.g., Ausubel et al., 1989; Sambrook & Russell, 2001; Agrawal, 1993; Tijssen, 1993; Tibanyenda et al., 1984; and Ebel et al., 1992.

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

As used herein, the term "target gene" refers to a gene expressed in a cell the expression of which is targeted for modulation using the methods and compositions of the presently disclosed subject matter. A target gene, therefore, comprises a nucleic acid sequence the expression level of which is downregulated by a nucleic acid sequence comprising a trigger sequence or a derivative thereof. Similarly, the terms "target RNA" or "target mRNA" refers to the transcript of a target gene to which the nucleic acid sequence comprising a trigger sequence is intended to bind, leading to modulation of the expression of the target gene. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

As used herein, the phrase "target RNA" refers to an RNA molecule (for example, an RNA molecule encoding a δ-cadinene synthase gene product) that is a target for modulation. Similarly, the phrase "target site" refers to a sequence within a target RNA that is "targeted" for cleavage mediated by a construct comprising a nucleic acid sequence comprising a trigger sequence that contains sequences within its antisense strand that are complementary to the target site. Also similarly, the phrase "target cell" refers to a cell that expresses a target RNA and into which a nucleic acid sequence comprising a trigger sequence is intended to be introduced. A target cell is in some embodiments a cell in a plant. For example, a target cell can comprise a target RNA expressed in a plant.

An nucleic acid sequence comprising a trigger sequence is "targeted to" an RNA molecule if it has sufficient nucleotide similarity to the RNA molecule that it would be expected to modulate the expression of the RNA molecule under conditions sufficient for the nucleic acid sequence comprising the trigger sequence and the RNA molecule to interact. In some embodiments, the interaction occurs within a plant cell. In some embodiments the interaction occurs under physiological conditions. As used herein, the phrase "physiological conditions" refers to in vivo conditions within a plant cell, whether that plant cell is part of a plant or a plant tissue, or that plant cell is being grown in vitro. Thus, as used herein, the phrase "physiological conditions" refers to the conditions within a plant cell under any conditions that the plant cell can be exposed to, either as part of a plant or when grown in vitro.

As used herein, the phrase "detectable level of cleavage" refers to a degree of cleavage of target RNA (and formation of cleaved product RNAs) that is sufficient to allow detection of cleavage products above the background of RNAs produced by random degradation of the target RNA. Production of RNAi-mediated cleavage products from at least 1-5% of the target RNA is sufficient to allow detection above background for most detection methods.

As used herein, the term "transcription" refers to a cellular process involving the interaction of an RNA polymerase with a gene that directs the expression as RNA of the structural information present in the coding sequences of the gene. The process includes, but is not limited to, the following steps: (a) the transcription initiation; (b) transcript elongation; (c) transcript splicing; (d) transcript capping; (e) transcript termination; (f) transcript polyadenylation; (g) nuclear export of the transcript; (h) transcript editing; and (i) stabilizing the transcript.

The term "transfection" refers to the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell can express a recombinant form of a polypeptide of the presently disclosed subject matter.

The transformation of a cell with an exogenous nucleic acid (for example, an expression vector) can be characterized as transient or stable. As used herein, the term "stable" refers to a state of persistence that is of a longer duration than that which would be understood in the art as "transient". These terms can be used both in the context of the transformation of cells (for example, a stable transformation), or for the expression of a transgene (for example, the stable expression of a vector-encoded nucleic acid sequence comprising a trigger sequence) in a transgenic cell. In some embodiments, a stable transformation results in the incorporation of the exogenous nucleic acid molecule (for example, an expression vector) into the genome of the transformed cell. As a result, when the cell divides, the vector DNA is replicated along with plant genome so that progeny cells also contain the exogenous DNA in their genomes.

In some embodiments, the term "stable expression" relates to expression of a nucleic acid molecule (for example, a vector-encoded nucleic acid sequence comprising a trigger sequence) over time. Thus, stable expression requires that the cell into which the exogenous DNA is introduced express the encoded nucleic acid at a consistent level over time. Additionally, stable expression can occur over the course of generations. When the expressing cell divides, at least a fraction of the resulting daughter cells can also express the encoded nucleic acid, and at about the same level. It should be understood that it is not necessary that every cell derived from the cell into which the vector was originally introduced express the nucleic acid molecule of interest. Rather, particularly in the context of a whole plant, the term "stable expression" requires only that the nucleic acid molecule of interest be stably expressed in tissue(s) and/or location(s) of the plant in which expression is desired. In some embodiments, stable expression of an exogenous nucleic acid is achieved by the integration of the nucleic acid into the genome of the host cell.

The term "vector" refers to a nucleic acid capable of transporting another nucleic acid to which it has been linked. One type of vector that can be used in accord with the presently disclosed subject matter is an *Agrobacterium* binary vector, i.e., a nucleic acid capable of integrating the nucleic acid sequence of interest into the host cell (for example, a plant cell) genome. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of plasmids. In the present specification, "plasmid" and "vector" are used interchangeably as the plasmid is the most commonly used form of vector. However, the presently disclosed subject matter is intended to include such other forms of expression vectors which serve equivalent functions and which become known in the art subsequently hereto.

The term "expression vector" as used herein refers to a DNA sequence capable of directing expression of a particular nucleotide sequence in an appropriate host cell, comprising a promoter operatively linked to the nucleotide sequence of interest which is operatively linked to transcription termination sequences. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. The nucleotide sequence of interest, including any additional sequences designed to effect proper expression of the nucleotide sequences, can also be referred to as an "expression cassette".

II. CONTROLLING AND ALTERING THE EXPRESSION OF NUCLEIC ACID MOLECULES

II.A. General Considerations

In studies of *C. elegans* development it was found that the lin-4 gene produced small RNAs of about 22 nucleotides (nt), instead of protein. It was further discovered that these small RNAs imperfectly paired to multiple sites in the 3'-untranslated region (3'-UTR) of lin-14 gene, mediating the translational repression of lin-14 message as part of the regulatory network that triggers the transition of developmental stages in the nematode (Lee et al., 1993; Wightman et al., 1993). These studies have led to the discovery of a new class of small, non-coding regulatory RNAs, termed microRNAs (miR-NAs), and, thus, of a new paradigm of gene expression regulation in eukaryotes (Lagos-Quintana et al., 2001; Lau et al., 2001; Lee & Ambros, 2001).

In a recent review, Bartel summarized the current knowledge of the biogenesis and functions of miRNAs in eukaryotes (Bartel, 2004). Briefly, the miRNA gene is presumably processed by RNA polymerase II or RNA polymerase III to the primary miRNA stem-loop transcript, called pri-miRNA (Lee Y et al., 2002). In mammals, the pri-miRNA is cleaved by the Drosha RNase III endonuclease at both stem strands near the stem-loop base, releasing an miRNA precursor (pre-miRNA) as an about. 60-70 nt stem-loop RNA molecule (Lee Y et al., 2002; Zeng & Cullen, 2003). The pre-miRNA is then transported into the cytoplasm where it is cleaved at both stem strands by Dicer, also an RNase III endonuclease, liberating the loop portion of the pre-miRNA and the stem portion of the duplex that comprises the mature miRNA of about 22 nt and the similar size miRNA* fragment derived from the opposing arm of the pre-miRNA (Lau et al., 2001; Lagos-Quintana et al., 2002; Aravin et al., 2003; Lim et al., 2003b). In plants, the nuclear cleavage of the pri-miRNA is mediated by a Dicer-like protein, DCL1, having a similar functionality as mammal Drosha (Reinhart et al., 2002; Lim et al., 2003b; Lee Y et al., 2002; Lee et al., 2003). The resulting plant pre-miRNA stem-loop transcripts are, however, generally more variable in size, ranging from about 60 to about 300 nt (Bartel & Bartel, 2003; Bartel, 2004; Lim et al., 2003b). It is believed that in plants, DCL1 performs a second cut in the nucleus on the pre-miRNA to liberate the miRNA:miRNA* duplex (Reinhart et al., 2002; Lim et al., 2003b; Lee Y et al., 2002; Lee et al., 2003).

After the export of the miRNA:miRNA* duplex to the cytoplasm, the miRNA pathway in plants and mammals appears to be quite similar, both involving helicase-like protein-mediated unwinding of the duplex to release the single-stranded mature miRNA (Bartel & Bartel, 2003; Bartel, 2004; Rhoades et al., 2002). The mature miRNA then recruits a ribonucleoprotein complex known as the RNA-induced silencing complex (RISC), while the miRNA* appears to be degraded. The miRNA guides the RISC to identify target messages based on perfect or near perfect complementarity between the miRNA and the target mRNA. Once such an mRNA is found, an endonuclease within the RISC cleaves the mRNA at a site near the middle of the miRNA complementarity, resulting in gene silencing (Hutvágner et al., 2000; Elbashir et al., 2001a; Elbashir et al., 2001b; Llave et al., 2002; Kasschau et al., 2003). In general, the miRNA in RISC will direct cleavage of the target mRNA if the complementarity between the target mRNA and the miRNA is sufficiently high. If such complementarity is not sufficiently high, however, the miRNA will direct the repression of protein translation rather than target mRNA cleavage (Bartel & Bartel, 2003; Bartel, 2004).

This miRNA-guided gene silencing pathway is highly similar to the key steps of siRNA-mediated gene silencing known as posttranscriptional gene silencing (PTGS) in plants and RNA interference (RNAi) in animals (Hamilton & Baulcombe, 1999; Hutvágner & Zamore, 2002). There is a distinction between miRNA and siRNA, however siRNAs, which can be exogenous sequences (for example, transgenes), mediate the silencing of the same genes from which they are derived. miRNAs, on the other hand, are typically endogenous and encoded by their own genes, and target different genes, setting up the gene regulation circuitry. However, artificial miRNAs can also be produced using a strategy outlined in Schwab et al., 2006, the disclosure of which is incorporated by reference herein, so this distinction might be more formal than functional.

One aspect of the presently disclosed subject matter provides compositions and methods for altering (e.g., decreasing) the level of nucleic acid molecules and/or polypeptides of the presently disclosed subject matter in plants. In particular, the nucleic acid molecules and polypeptides of the presently disclosed subject matter are expressed constitutively, temporally, or spatially (e.g., at developmental stages), in certain tissues, and/or quantities, which are uncharacteristic of non-recombinantly engineered plants. In some embodiments, the presently disclosed subject matter provides compositions and methods for decreasing an expression level of a δ-cadinene synthase gene and/or gene product (e.g., a δ-cadinene synthase RNA or a polypeptide encoded thereby) to decrease the accumulation of gossypol in one or more of the tissues of a cotton plant.

Embodiments of the presently disclosed subject matter provide an expression cassette comprising one or more elements operably linked in an isolated nucleic acid. In some embodiments, the expression cassette comprises one or more operably linked promoters, coding sequences, and/or promoters.

Further encompassed within the presently disclosed subject matter are recombinant vectors comprising an expression cassette according to the embodiments of the presently disclosed subject matter. Also encompassed are plant cells comprising expression cassettes according to the present disclosure, and plants comprising these plant cells. In some embodiments, the plant is a dicot. In some embodiments, the plant is cotton.

In some embodiments, the expression cassette is expressed in a specific location or tissue of a plant. In some embodiments, the location or tissue includes, but is not limited to, epidermis, root, vascular tissue, meristem, cambium, cortex, pith, leaf, flower, seed, and combinations thereof. In some embodiments, the location or tissue is a seed.

Embodiments of the presently disclosed subject matter also relate to an expression vector comprising an expression cassette as disclosed herein. In some embodiments, the expression vector comprises one or more elements including, but not limited to, a promoter sequence, an enhancer sequence, a selection marker sequence, a trigger sequence, an intron-containing hairpin transformation construct, an origin of replication, and combinations thereof.

In some embodiments, the expression vector comprises a eukaryotic expression vector, and in some embodiments, the expression vector comprises a prokaryotic expression vector. In some embodiments, the eukaryotic expression vector comprises a tissue-specific promoter. In some embodiments, the expression vector is operable in plants.

The presently disclosed subject matter further provides a method for modifying (i.e. increasing or decreasing) the concentration or composition of a polypeptide of the presently disclosed subject matter (e.g., a δ-cadinene synthase polypeptide) in a plant or part thereof. The method comprises in some embodiments introducing into a plant cell an expression cassette comprising a nucleic acid molecule of the presently disclosed subject matter as disclosed above to obtain a transformed plant cell or tissue (also referred to herein as a "transgenic" plant cell or tissue), and culturing the transformed plant cell or tissue. The nucleic acid molecule can be under the regulation of a constitutive or inducible promoter, and in some embodiments can be under the regulation of a tissue- or cell type-specific promoter. In some embodiments, the expression of the nucleic acid molecule in the plant cell or tissue results in a decrease in the amount of gossypol that accumulates in the plant cell or tissue. In some embodiments, the expression of the nucleic acid molecule in the plant cell or tissue results in a change in the level of one or more other terpenoids besides gossypol in the plant cell or tissue.

A plant or plant part having modified expression of a nucleic acid molecule of the presently disclosed subject matter can be analyzed and selected using methods known to those skilled in the art including, but not limited to, Southern blotting, DNA sequencing, and/or PCR analysis using primers specific to the nucleic acid molecule and detecting amplicons produced therefrom.

In general, the presently disclosed compositions and methods can result in an increase or a decrease in the level of a nucleic acid molecule, a polypeptide encoded by the nucleic acid molecule, and/or a product produced by a biological activity of the polypeptide (either directly by the polypeptide or in a biochemical pathway in which the polypeptide would normally take part) by in some embodiments at least 5%, in some embodiments at least 10%, in some embodiments at least 20%, in some embodiments at least 30%, in some embodiments at least 40%, in some embodiments at least 50%, in some embodiments at least 60%, in some embodiments at least 70%, in some embodiments at least 80%, and in some embodiments at least 90% relative to a native control plant, plant part, or cell lacking the expression cassette.

In some embodiments, the presently disclosed subject matter provides methods for reducing the level of gossypol in a seed of a transgenic cotton plant, the method comprising expressing in the seed a transgene encoding a δ-cadinene synthase gene trigger sequence, wherein the expressing induces RNA interference (RNAi) in the seed, whereby the level of gossypol in the seed is reduced. As used herein, the phrase "δ-cadinene synthase gene trigger sequence" refers to a recombinant nucleotide sequence that when expressed in a plant cell or tissue becomes a part of a nucleic acid molecule that induces RNA interference (RNAi) and/or post-transcriptional gene silencing (PTGS) against a δ-cadinene synthase gene product in the plant cell or tissue. In some embodiments, the δ-cadinene synthase gene trigger sequence comprises a subsequence of a δ-cadinene synthase gene that includes at least 15 consecutive nucleotides of one of SEQ ID NOs: 1 and 13-21. In some embodiments, the plant cell or tissue is a cotton cell or tissue. Methods and compositions for inducing RNAi directed against a δ-cadinene synthase gene product are discussed in more detail hereinbelow.

Additional gene products involved in the biosynthesis of gossypol can also be targeted for RNAi-based inhibition strategies that are designed to reduce gossypol in the seed of a cotton plant. An exemplary additional target gene is the cotton δ-cadinene-8-hydroxylase gene (also called CYP706B1 or P450 monooxygenase), the nucleotide sequence for which is disclosed as GENBANK® Accession No. AF332974 (see also SEQ ID NO: 22). The cotton δ-cadinene-8-hydroxylase gene is described also in U.S. Patent Application Publication No. 20020187538, the disclosure of which is incorporated herein by reference in its entirety.

Using the techniques set forth herein, compositions and methods that can be employed to target the cotton δ-cadinene-8-hydroxylase gene can also be generated. For example, vectors including, but not limited to *A. tumefaciens* transformation vectors can be produced that include a trigger sequence based on the full length sequence of the δ-cadinene-8-hydroxylase gene (SEQ ID NO: 22) or a fragment thereof. These vectors can be employed to transform cotton cells to reduce gossypol in seeds that are derived from the transformed cotton cells.

II.B. Alteration of Expression of Nucleic Acid Molecules

In some embodiments, the presently disclosed subject matter takes advantage of the ability of short, double stranded RNA molecules to modulate the expression of cellular genes, a process referred to as RNA interference (RNAi) or post transcriptional gene silencing (PTGS). As used herein, the terms "RNA interference" and "post-transcriptional gene silencing" are used interchangeably and refer to a process of sequence-specific down regulation of gene expression mediated by a small interfering RNA (siRNA) or micro RNA (miRNA). See generally Fire et al., 1998; U.S. Pat. No. 6,506,559; U.S. Pat. No. 7,005,423. The process of post-transcriptional gene silencing is thought to be an evolutionarily conserved cellular defense mechanism that has evolved to prevent the expression of foreign genes (Fire, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of dsRNA in cells triggers various responses, one of which is RNAi. RNAi appears to be different from the interferon response to dsRNA, which results from dsRNA-mediated activation of an RNA-dependent protein kinase (PKR) and 2',5'-oligoadenylate synthetase, resulting in non-specific cleavage of mRNA by ribonuclease L.

The presence of long dsRNAs in plant or animal cells stimulates the activity of the enzyme Dicer, a ribonuclease III. Dicer catalyzes the degradation of dsRNA into short stretches of dsRNA referred to as small interfering RNAs (siRNA; Bernstein et al., 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., 2001b).

RNAi has been described in several cell type and organisms. Fire et al., 1998 described RNAi in *C. elegans*. Wianny & Zernicka-Goetz, 1999 disclose RNAi mediated by dsRNA in mouse embryos. Hammond et al., 2000 were able to induce RNAi in *Drosophila* cells by transfecting dsRNA into these cells. Elbashir et al., 2001a demonstrated the presence of RNAi in cultured mammalian cells including human embryonic kidney and HeLa cells by the introduction of duplexes of synthetic 21 nucleotide RNAs.

Experiments using *Drosophila* embryonic lysates revealed certain aspects of siRNA length, structure, chemical composition, and sequence that are involved in RNAi activity. See Elbashir et al., 2001c. In this assay, 21 nucleotide siRNA duplexes were most active when they contain 3'-overhangs of two nucleotides. Also, the position of the cleavage site in the target RNA was shown to be defined by the 5'-end of the siRNA guide sequence rather than the 3'-end (Elbashir et al., 2001b).

Other studies have indicated that a 5'-phosphate on the target-complementary strand of a siRNA duplex is required for siRNA activity and that ATP is utilized to maintain the 5'-phosphate moiety on the siRNA (Nykanen et al., 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359,180).

Other references disclosing the use of dsRNA and RNAi include PCT International Publication Nos. WO 01/75164 (in vitro RNAi system using cells from *Drosophila* and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi). See also PCT International Patent Application Publication Nos. WO 99/32619, WO 99/53050, or WO 99/61631. The disclosure of each of these references is incorporated herein by reference in its entirety.

Thus, alteration of the expression of a target gene product (e.g., a δ-cadinene synthase gene product) can be obtained by double stranded RNA (dsRNA) interference (RNAi). For example, the entirety, or in some embodiments a portion, of a nucleotide sequence of the presently disclosed subject matter, can be comprised in a DNA molecule. The size of the DNA molecule can depend on the size of the dsRNA that is desired, and is in some embodiments less than about 50 nucleotides (e.g., about 15, 20, 25, 30, 35, 40, 45, or 50 nucleotides, or any integer length there between), in some embodiments about 50-100 nucleotides, and in some embodiments from 100 to 1000 nucleotides or more. Two copies of the DNA molecule are linked, separated by a spacer DNA molecule, such that the first and second copies are in opposite orientations. In some embodiments, the first copy of the DNA molecule is the reverse-complement (also known as the non-coding strand) and the second copy is the coding strand; in some embodiments, the first copy is the coding strand, and the second copy is the reverse complement. The size of the spacer DNA molecule is highly variable, and is in some embodiments 200 to 10,000 nucleotides, in some embodiments 400 to 5000 nucleotides, and in some embodiments 600 to 1500 nucleotides in length. The spacer is in some embodiments a random piece of DNA, in some embodiments a random piece of DNA without homology to the target organism for dsRNA interference, and in some embodiments a functional intron that is effectively spliced by the target organism.

The two copies of the DNA molecule separated by the spacer are operably linked to a promoter functional in a plant cell, and introduced in a plant cell in which the nucleotide sequence is expressible. In some embodiments, the DNA molecule comprising the nucleotide sequence, or a portion thereof, is stably integrated in the genome of the plant cell. In some embodiments, the DNA molecule comprising the nucleotide sequence, or a portion thereof, is comprised in an extrachromosomally replicating molecule. Several publications describing this approach are cited for further illustration (Waterhouse et al., 1998; Chuang & Meyerowitz, 2000).

In transgenic plants containing one of the DNA molecules disclosed immediately above, the expression of the nucleotide sequence corresponding to the nucleotide sequence comprised in the DNA molecule is in some embodiments reduced. In some embodiments, the nucleotide sequence in the DNA molecule is at least 70% identical to the nucleotide sequence the expression of which is reduced, in some embodiments it is at least 80% identical, in some embodiments it is at least 90% identical, in some embodiments it is at least 95% identical, and in some embodiments it is at least 99% identical.

II.C. Construction of Plant Expression Vectors

Coding sequences intended for expression in transgenic plants can be first assembled in expression cassettes operably linked to a suitable promoter expressible in plants. The expression cassettes can also comprise any further sequences required or selected for the expression of the transgene. Such sequences include, but are not limited to, transcription terminators, extraneous sequences to enhance expression such as introns, vital sequences, and sequences intended for the targeting of the transgene-encoded product to specific organelles and cell compartments. These expression cassettes can then be easily transferred to the plant transformation vectors disclosed below. The following is a description of various components of typical expression cassettes.

II.C.1. Promoters

The selection of the promoter used in expression cassettes can determine the spatial and temporal expression pattern of the transgene in the transgenic plant. Selected promoters can express transgenes in specific cell types (such as leaf epidermal cells, mesophyll cells, root cortex cells) or in specific tissues or organs (roots, leaves, flowers, or seeds, for example) and the selection can reflect the desired location for accumulation of the transgene. Alternatively, the selected promoter can drive expression of the gene under various inducing conditions. Promoters vary in their strength; i.e., their abilities to promote transcription. Depending upon the host cell system utilized, any one of a number of suitable promoters can be used, including the gene's native promoter. The following are non-limiting examples of promoters that can be used in expression cassettes.

II.C.1.a. Constitutive Expression: the Ubiquitin Promoter

Ubiquitin is a gene product known to accumulate in many cell types and its promoter has been cloned from several species for use in transgenic plants (e.g. sunflower—Binet et al., 1991; maize—Christensen & Quail, 1989; and *Arabidopsis*—Callis et al., 1990). The *Arabidopsis* ubiquitin promoter is suitable for use with the nucleotide sequences of the presently disclosed subject matter. The ubiquitin promoter is suitable for gene expression in transgenic plants, both monocotyledons and dicotyledons. Suitable vectors are derivatives of pAHC25 or any of the transformation vectors disclosed herein, modified by the introduction of the appropriate ubiquitin promoter and/or intron sequences.

II.C.1.b. Constitutive Expression: the CaMV 35S Promoter

Construction of the plasmid pCGN1761 is disclosed in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker that includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those disclosed below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that can enhance translation. This is particularly useful when overexpression is desired. For example, pCGN1761ENX can be modified by optimization of the translational initiation site as disclosed in Example 37 of U.S. Pat. No. 5,639,949, incorporated herein by reference.

II.C.1.c. Constitutive Expression: the Actin Promoter

Several isoforms of actin are known to be expressed in most cell types and consequently the actin promoter can be used as a constitutive promoter. In particular, the promoter from the rice ActI gene has been cloned and characterized (McElroy at al., 1990). A 1.3 kilobase (kb) fragment of the promoter was found to contain all the regulatory elements required for expression in rice protoplasts. Furthermore, expression vectors based on the ActI promoter have been constructed (McElroy et al., 1991). These incorporate the ActI-intron 1, AdhI 5' flanking sequence (from the maize alcohol dehydrogenase gene) and AdhI-intron 1 and sequence from the CaMV 35S promoter. Vectors showing highest expression were fusions of 35S and ActI intron or the ActI 5' flanking sequence and the ActI intron. Optimization of sequences around the initiating ATG (of the β-glucuronidase (GUS) reporter gene) also enhanced expression.

The promoter expression cassettes disclosed in McElroy et al., 1991, can be easily modified for gene expression. For example, promoter-containing fragments are removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al., 1993).

II.C.1.d. Inducible Expression: PR-1 Promoters

The double 35S promoter in pCGN1761ENX can be replaced with any other promoter of choice that will result in suitably high expression levels. By way of example, one of the chemically regulatable promoters disclosed in U.S. Pat. No. 5,614,395, such as the tobacco PR-1a promoter, can replace the double 35S promoter. Alternately, the *Arabidopsis* PR-1 promoter disclosed in Lebel et al., 1998, can be used. The promoter of choice can be excised from its source by restriction enzymes, but can alternatively be PCR-amplified using primers that carry appropriate terminal restriction sites. Should PCR-amplification be undertaken, the promoter can be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., 1992). pCIB1004 is cleaved with NcoI and the resulting 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is accomplished by cleavage with XhoI and blunting with T4 polymerase, followed by cleavage with HindIII, and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those disclosed herein. Various chemical regulators can be employed to induce expression of the selected coding sequence in the plants transformed according to the presently disclosed subject matter, including the benzothiadiazole, isonicotinic acid, and salicylic acid compounds disclosed in U.S. Pat. Nos. 5,523,311 and 5,614,395.

II.C.1.e. Inducible Expression: an Ethanol-Inducible Promoter

A promoter inducible by certain alcohols or ketones, such as ethanol, can also be used to confer inducible expression of a coding sequence of the presently disclosed subject matter. Such a promoter is for example the alcA gene promoter from *Aspergillus nidulans* (Caddick et al., 1998). In *A. nidulans*, the alcA gene encodes alcohol dehydrogenase I, the expression of which is regulated by the AlcR transcription factors in presence of the chemical inducer. For the purposes of the presently disclosed subject matter, the CAT coding sequences in plasmid palcA:CAT comprising a alcA gene promoter sequence fused to a minimal 35S promoter (Caddick et al., 1998) are replaced by a coding sequence of the presently disclosed subject matter to form an expression cassette having the coding sequence under the control of the alcA gene promoter. This is carried out using methods known in the art.

II.C.1.f. Inducible Expression: a Glucocorticoid-Inducible Promoter

Induction of expression of a nucleic acid sequence of the presently disclosed subject matter using systems based on steroid hormones is also provided. For example, a glucocorticoid-mediated induction system is used (Aoyama & Chua, 1997) and gene expression is induced by application of a glucocorticoid, for example a synthetic glucocorticoid, for example dexamethasone, at a concentration ranging in some embodiments from 0.1 mM to 1 mM, and in some embodiments from 10 mM to 100 mM. For the purposes of the presently disclosed subject matter, the luciferase gene sequences Aoyama & Chua are replaced by a nucleic acid sequence of the presently disclosed subject matter to form an expression cassette having a nucleic acid sequence of the presently disclosed subject matter under the control of six copies of the GAL4 upstream activating sequences fused to the 35S minimal promoter. This is carried out using methods known in the art. The trans-acting factor comprises the GAL4 DNA-binding domain fused to the transactivating domain of the herpes viral polypeptide VP16 fused to the hormone-binding domain of the rat glucocorticoid receptor. The expression of the fusion polypeptide is controlled either by a promoter known in the art or disclosed herein. A plant comprising an expression cassette comprising a nucleic acid sequence of the presently disclosed subject matter fused to the 6×GAL4/minimal promoter is also provided. Thus, tissue- or organ-specificity of the fusion polypeptide is achieved leading to inducible tissue- or organ-specificity of the nucleic acid sequence to be expressed.

II.C.1.g. Root Specific Expression

Another pattern of gene expression is root expression. A suitable root promoter is the promoter of the maize metallothionein-like (MTL) gene disclosed in de Framond, 1991, and also in U.S. Pat. No. 5,466,785, each of which is incorporated herein by reference. This "MTL" promoter is transferred to a suitable vector such as pCGN 1761 ENX for the insertion of a selected gene and subsequent transfer of the entire promoter-gene-terminator cassette to a transformation vector of interest.

II.C.1.h. Wound-Inducible Promoters

Wound-inducible promoters can also be suitable for gene expression. Numerous such promoters have been disclosed (e.g. Xu et al., 1993; Logemann et al., 1989; Rohrmeier & Lehle, 1993; Firek et al., 1993; Warner et al., 1993) and all are suitable for use with the presently disclosed subject matter. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA that is wound induced and which can be used to isolate the cognate promoter using standard techniques. Similarly, Firek et al. and Warner et al. have disclosed a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to the presently disclosed subject matter, and used to express these genes at the sites of plant wounding.

II.C.1.i. Pith-Preferred Expression

PCT International Publication WO 93/07278, which is herein incorporated by reference, describes the isolation of the maize trpA gene, which is preferentially expressed in pith cells. The gene sequence and promoter extending up to −1726 basepairs (bp) from the start of transcription are presented. Using standard molecular biological techniques, this promoter, or parts thereof, can be transferred to a vector such as pCGN 1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

II.C.1.j. Leaf-Specific Expression

A maize gene encoding phosphoenol carboxylase (PEPC) has been disclosed by Hudspeth & Grula, 1989. Using standard molecular biological techniques, the promoter for this gene can be used to drive the expression of any gene in a leaf-specific manner in transgenic plants.

II.C.1.k. Pollen-Specific Expression

WO 93/07278 describes the isolation of the maize calcium-dependent protein kinase (CDPK) gene that is expressed in pollen cells. The gene sequence and promoter extend up to 1400 bp from the start of transcription. Using standard molecular biological techniques, this promoter, or parts thereof can be transferred to a vector such as pCGN 1761 where it can replace the 35S promoter and be used to drive the expression of a nucleic acid sequence of the presently disclosed subject matter in a pollen-specific manner.

II.C.1.l. Seed-Specific Expression

In some embodiments of the presently disclosed subject matter, a δ-cadinene synthase gene trigger sequence is expressed in a seed-specific fashion in a cotton plant. Seed-specific promoters can include those promoters associated with genes involved with the production of seed storage proteins, which typically are expressed at high levels during seed development and for which expression is tightly controlled both spatially and temporally in the developing seed.

As such, regulatory sequences from genes encoding seed storage proteins can represent a valuable source of promoters that can be utilized to drive the expression of transgenes in a seed-specific manner. The promoters from the soybean β-conglycinin genes, the French bean phaseolin gene, the sunflower helianthinin gene, and the carrot Dc3 promoter are examples of some of the well-characterized seed-specific promoters from dicots (see U.S. Patent Application Publication No. 2003/0154516 and references cited therein, the entire disclosures of which are incorporated by reference herein). Additional promoters that have been shown to be seed-specific in cotton include the soybean (*Glycine max*) lectin promoter described in Townsend & Llewellyn, 2002, and the Gh-sp promoter that was derived from a seed protein gene and is described in Song et al., 2000.

In some embodiments, a seed-specific promoter comprises a promoter from the cotton seed-specific α-globulin gene. The 5' regulatory region of this gene, or subsequences thereof, when operably linked to either the coding sequence of a transgene comprising a δ-cadinene synthase gene trigger sequence, direct expression of the δ-cadinene synthase gene trigger sequence in a plant seed. Sequences that can direct seed-specific transgene expression include instant SEQ ID NOs: 10-12, which correspond to SEQ ID NOs: 1-3 of PCT International Patent Application Publication No. WO 2003/052111, the entire disclosure of which is incorporated herein by reference.

II.C.2. Transcriptional Terminators

A variety of transcriptional terminators are available for use in expression cassettes. These are responsible for termination of transcription and correct mRNA polyadenylation. Appropriate transcriptional terminators are those that are known to function in plants and include the CaMV 35S terminator, the tml terminator, the nopaline synthase terminator, the octopine synthase terminator, and the pea rbcS E9 terminator. These can be used in both monocotyledons and dicotyledons. In addition, a gene's native transcription terminator can be used.

II.C.3. Sequences for the Enhancement or Regulation of Expression

Numerous sequences have been found to enhance gene expression from within the transcriptional unit and these sequences can be used in conjunction with the genes of the presently disclosed subject matter to increase their expression in transgenic plants.

Various intron sequences have been shown to enhance expression, particularly in monocotyledonous cells. For example, the introns of the maize AdhI gene have been found to significantly enhance the expression of the wild type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV; the "W-sequence"), Maize Chlorotic Mottle Virus (MCMV), and Alfalfa Mosaic Virus (AMV) have been shown to be effective in enhancing expression (see e.g., Gallie et al., 1987; Skuzeski et al., 1990). Other leader sequences known in the art include, but are not limited to, picornavirus leaders, for example, EMCV (encephalomyocarditis virus) leader (5' noncoding region; see Elroy-Stein et al., 1989); potyvirus leaders, for example, from Tobacco Etch Virus (TEV; see Allison et al., 1986); Maize Dwarf Mosaic Virus (MDMV; see Kong & Steinbiss 1998); human immunoglobulin heavy-chain binding polypeptide (BiP) leader (Macejak & Sarnow, 1991); untranslated leader from the coat polypeptide mRNA of alfalfa mosaic virus (AMV; RNA 4; see Jobling & Gehrke, 1987); tobacco mosaic virus (TMV) leader (Gallie et al., 1989); and Maize Chlorotic Mottle Virus (MCMV) leader (Lommel et al., 1991). See also Della-Cioppa et al., 1987.

II.D. Construction of Plant Transformation Vectors

Numerous transformation vectors available for plant transformation are known to those of ordinary skill in the plant transformation art, and the genes pertinent to the presently disclosed subject matter can be used in conjunction with any such vectors. The selection of vector will depend upon the selected transformation technique and the target species for transformation. For certain target species, different antibiotic or herbicide selection markers might be employed. Selection markers used routinely in transformation include the nptII gene, which confers resistance to kanamycin and related antibiotics (Messing & Vieira, 1982; Bevan et al., 1983); the bar gene, which confers resistance to the herbicide phosphinothricin (White et al., 1990; Spencer et al., 1990); the hph gene, which confers resistance to the antibiotic hygromycin (Blochinger & Diggelmann, 1984); the dhfr gene, which confers resistance to methotrexate (Bourouis & Jarry, 1983); the EPSP synthase gene, which confers resistance to glyphosate (U.S. Pat. Nos. 4,940,935 and 5,188,642); and the mannose-6-phosphate isomerase gene, which provides the ability to metabolize mannose (U.S. Pat. Nos. 5,767,378 and 5,994,629).

II.D.1. Vectors Suitable for *Agrobacterium* Transformation

Many vectors are available for transformation using *Agrobacterium tumefaciens*. These typically carry at least one T-DNA border sequence and include vectors such as pBIN19 (Bevan, 1984). Below, the construction of two typical vectors suitable for *Agrobacterium* transformation is disclosed.

II.D.1.a. pCIB200 and pCIB2001

The binary vectors pCIB200 and pCIB2001 are used for the construction of recombinant vectors for use with *Agrobacterium* and are constructed in the following manner. pTJS75kan is created by NaiI digestion of pTJS75 (Schmidhauser & Helinski, 1985) allowing excision of the tetracycline-resistance gene, followed by insertion of an AccI fragment from pUC4K carrying an NPTII sequence (Messing & Vieira, 1982: Bevan et al., 1983: McBride et al., 1990). XhoI linkers are ligated to the EcoRV fragment of PCIB7 which contains the left and right T-DNA borders, a plant selectable nos/nptII chimeric gene and the pUC polylinker (Rothstein et al., 1987), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites, also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

II.D.1.b. pCIB10 and Hygromycin Selection Derivatives Thereof

The binary vector pCIB10 contains a gene encoding kanamycin resistance for selection in plants, T-DNA right and left border sequences, and incorporates sequences from the wide host-range plasmid pRK252 allowing it to replicate in both *E. coli* and *Agrobacterium*. Its construction is disclosed by Rothstein et al., 1987. Various derivatives of pCIB10 can be constructed which incorporate the gene for hygromycin B phosphotransferase disclosed by Gritz & Davies, 1983. These derivatives enable selection of transgenic plant cells on hygromycin only (pCIB743), or hygromycin and kanamycin (pCIB715, pCIB717).

II.D.2. Vectors Suitable for Non-*Agrobacterium* Transformation

Transformation without the use of *Agrobacterium tumefaciens* circumvents the requirement for T-DNA sequences in the chosen transformation vector, and consequently vectors lacking these sequences can be utilized in addition to vectors such as the ones disclosed above that contain T-DNA sequences. Transformation techniques that do not rely on *Agrobacterium* include transformation via particle bombardment, protoplast uptake (e.g. polyethylene glycol (PEG) and electroporation), and microinjection. The choice of vector depends largely on the species being transformed. Below, the construction of typical vectors suitable for non-*Agrobacterium* transformation is disclosed.

II.D.2.a. pCIB3064 pCIB3064 is a pUC-derived vector suitable for direct gene transfer techniques in combination with selection by the herbicide BASTA® (glufosinate ammonium or phosphinothricin). The plasmid pCIB246 comprises the CaMV 35S promoter in operational fusion to the *E. coli* β-glucuronidase (GUS) gene and the CaMV 35S transcriptional terminator and is disclosed in the PCT International Publication WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich, England, and the 400 bp SmaI fragment containing the bar gene from *Streptomyces viridochromogenes* is excised and inserted into the HpaI site of pCIB3060 (Thompson et al., 1987). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

II.D.2.b. pSOG19 and pSOG35 pSOG35 is a transformation vector that utilizes the *E. coli* dihydrofolate reductase (DHFR) gene as a selectable marker conferring resistance to methotrexate. PCR is used to amplify the 35S promoter (~800 bp), intron 6 from the maize Adh1 gene (~550 bp), and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (BD Biosciences Clontech, Palo Alto, Calif., United States of America) that comprises the pUC19 vector backbone and the nopaline synthase terminator. Assembly of these fragments generates pSOG19 that contains the 35S promoter in fusion with the intron 6 sequence, the GUS leader, the DHFR gene, and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI, and EcoRI sites available for the cloning of foreign substances.

II.E. Transformation

Once a nucleic acid sequence of the presently disclosed subject matter has been cloned into an expression system, it is transformed into a plant cell. The receptor and target expression cassettes of the presently disclosed subject matter can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation-mediated uptake, particle bombardment-mediated delivery, or microinjection. Examples of these techniques are disclosed in Paszkowski et al., 1984; Potrykus et al., 1985; and Klein et al., 1987. In each case the transformed cells are regenerated to whole plants using standard techniques known in the art.

*Agrobacterium*-mediated transformation is a useful technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which can depend on the complement of vir genes carried by the host *Agrobacterium* strain either on a co-resident Ti plasmid or chromosomally (e.g. strain CIB542 for pCIB200 and pCIB2001 (Uknes et al., 1993). The transfer of the recombinant binary vector to *Agrobacterium* is accomplished by a triparental mating procedure using *E. coli* carrying the recombinant binary vector, a helper *E. coli* strain that carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, 1988).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050; 5,036,006; and 5,100,792; all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

In some embodiments, the plant species transformed is a member of the genus Gossypium. Techniques for transforming Gossypium are disclosed in, for example, U.S. Pat. Nos. 5,004,863; 5,159,135; 5,164,310; 5,846,797; 5,929,300; 5,998,207; 5,986,181; 6,479,287; 6,483,013; 6,573,437; 6,620,990; 6,624,344; 6,660,914; 6,730,824; 6,858,777; and 7,122,722; PCT International Patent Application Publication Nos. WO 97/43430; WO 00/53783; WO 00/77230; and Rathore et al., 2006, the disclosure of each of which is incorporated herein by reference in its entirety. The production and characterization of transgenic cotton are also disclosed in the following United States patents, the disclosures of which are incorporated by reference in their entireties: U.S. Pat. Nos. 5,188,960; 5,338,544; 5,474,925; 5,495,070; 5,521,078; 5,602,321; 5,608,142; 5,608,148; 5,597,718; 5,620,882; 5,633,435; 5,827,514; 5,869,720; 5,880,275; 5,981,834; 6,054,318; 6,107,549; 6,218,188; 6,308,458; 6,329,570; 6,448,476; 6,472,588; 6,559,363; 6,563,022; 6,703,540; 6,710,228; 6,753,463; 6,818,807; 6,943,282; 6,472,588; 6,559,363; 6,563,022; 6,703,540; 6,710,228; 6,753,463; 6,818,807; 6,943,282; 6,974,898; 7,041,877; 7,053,270; and 7,091,400.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Hairpin RNA Construct and Cotton Transformation

Figure 3:
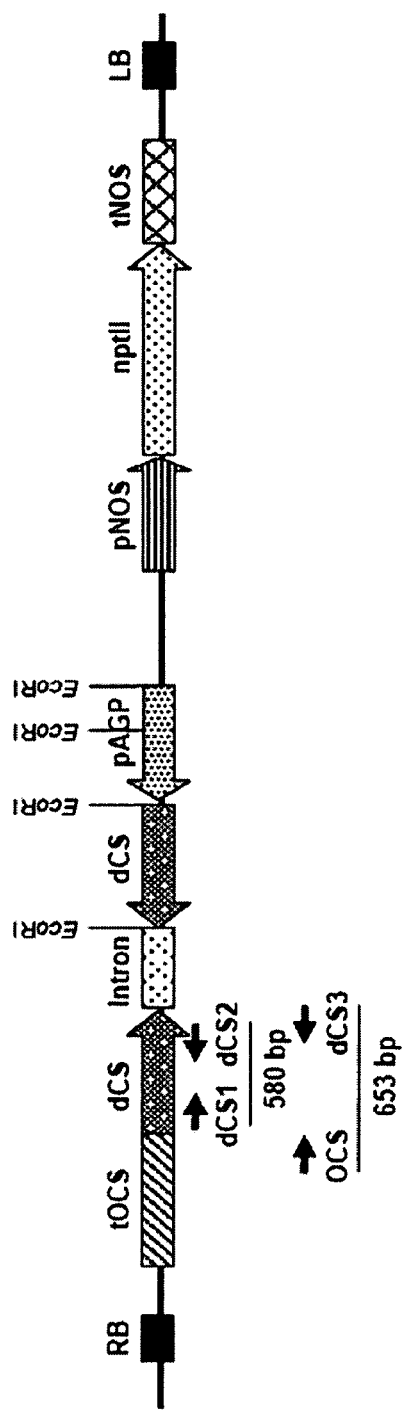
FIG. 3 is a schematic diagram depicting the T-DNA region of *A. tumefaciens* binary vector pAGP-iHP-dCS. Arrows below the depiction of the construct indicate the positions of the primers used in the PCR analyses. RB: right T-DNA border; tOCS: octopine synthase terminator; dCS: 604-bp δ-cadinene synthase sequence; pAGP: cotton α-globulin promoter; pNOS: nopaline synthase promoter; nptII: neomycin phosphotransferase II; tNOS: nopaline synthase terminator; LB: left T-DNA border.

A clone of a δ-cadinene synthase gene was obtained by probing a cDNA library prepared from staged embryo mRNA from G. hirsutum (cv. Coker 312) with the G. arboreum cad1-C1 (XC1) gene (GENBANK® Accession No. U23205). Sequencing confirmed that the clone belonged to the δ-cadinene synthase C subfamily. A 604 bp long internal fragment amplified from the cDNA clone used as the trigger sequence (SEQ ID NO: 1) is shown in FIG. 2. It bore 80% to greater than 99% homology to corresponding subsequences of various published δ-cadinene synthase gene sequences from diploid and tetraploid cottons (see Table 1). This sequence was utilized to make an intron-containing hairpin (ihp) construct using the pHANNIBAL/pART27 system (Wesley et al., 2001). The seed-specific promoter from the cotton α-globulin B gene (SEQ ID NO: 10; see also Sunilkumar et al., 2002) was used to control the expression of the ihpRNA sequence. The final hairpin clone pAGP-iHP-dCS (depicted in FIG. 3), which harbors nptII as the plant selectable marker gene, was introduced into Agrobacterium strain LBA4404, which was then used to transform a G. hirsutum cv. Coker 312 as described in Sunilkumar & Rathore, 2001.

TABLE 1

Homology of the 604 by dCS Trigger Sequence to Various Isoforms of the δ-cadinene Synthase Gene from Cotton

| δ-cadinene synthase gene | GENBANK® Accession No. | Plant source | Percent Homology to SEQ ID NO: 1 |
|---|---|---|---|
| Cad1-C14 (XC14) | U23205 | G. arboreum | 99.8 |
| Cdn1-C4 | AF270425 | G. hirsutum | 98.8 |
| Cdn1 | U88318 | G. hirsutum | 98.5 |
| Cad1-C2 | Y16432 | G. arboreum | 96.4 |
| Cad1-C3 | AF174294 | G. arboreum | 96.2 |
| Cad1-C1 (XC1) | U23206 | G. arboreum | 96.0 |
| Cad1-B | X95323 | G. arboreum | 92.9 |
| Cdn-D1 | AY800107 | G. hirsutum | 90.9 |
| Cad1-A | X96429 | G. arboreum | 80.9 |

Example 2

Determination of Gossypol and Other Terpenoids

Levels of gossypol and related terpenoids in cottonseed and other tissues were determined by utilizing the HPLC-based methods described in Stipanovic et al., 1988 and Benson et al., 2001. Briefly, kernel from individual mature cottonseed (dry weight ranged from 70-95 mg) was ground to a fine powder using agate mortar and pestle. Approximately 20 mg of kernel powder from each seed was saved for DNA extraction the remaining portion was weighed, mixed with 5 ml of solvent containing ethanol:ether:water:glacial acetic acid (59:17:24:0.2) by vortexing, and incubated at room temperature for 1 hour. The sample was then centrifuged for 5 minutes at 2800×g. A 50 µl fraction of the extract was analyzed on a Hewlett-Packard 1090 liquid chromatograph as described in Stipanovic et al., 1988.

A fully expanded third leaf from either a wild type or each of the 10 $T_1$ plants from the two RNAi transgenic lines was used for the terpenoid aldehyde analysis. Flower bud (5-7 mm diameter), bracts (0 dpa), boll (1 dpa), and root tissues were collected from three replicate, PCR-positive, transgenic $T_1$ plants each from line LCT66-2 and line LCT66-32. Tissues collected from three null segregant plants and three wild type plants, grown under the same conditions and at the same time as $T_1$ transformants in the greenhouse, served as controls. The tissue samples were dried in a lyophilizer and ground to a fine powder. The powder (dry weight ranged from 50 to 100 mg) was extracted with 5 ml of solvent containing acetonitrile:water:phosphoric acid (80:20:0.1) by ultrasonification for 3 minutes. The sample was centrifuged for 5 minutes at 2800× g. A 50 µl fraction of the extract was analyzed on HPLC as described hereinabove.

Example 3

RNA Isolation

RNA was isolated from one half of the 35 dpa embryo that was stored in RNALATER® solution (Ambion, Austin, Tex., United States of America). The embryo was ground in 550 µl of RNA isolation buffer (4M guanidine isothiocyanate, 30 mM disodium citrate; 30 mM β-mercaptoethanol) with Proteinase K (1.5 mg per sample) using mortar and pestle. The extract was then processed using the RNEASY® Plant Mini Kit (Qiagen, Valencia, Calif., United States of America; Catalogue No. 74904) for RNA isolation.

Example 4

Duplex RT-PCR Analysis

Total RNA (400 ng) was reverse transcribed with oligo (dT) primers using the TAQMAN® Reverse Transcription Reagents (Applied Biosystems, Inc, Foster City, Calif., United States of America; Catalogue No. N808-0234) in a 10 µl reaction. The reaction conditions were as per manufacturer's instructions. 2 µl of the synthesized first-strand cDNA was used for PCR amplification of δ-cadinene synthase cDNA and an internal control, histone 3 (GENBANK® Accession No. AF024716) cDNA in the same reaction. The following primers were used: dCS1: 5'-ATG CCG AGA ACG ACC TCT ACA-3' (SEQ ID NO: 2); dCS2: 5'-ACT TTT GTC AAC ATC TTT CTA CCA AG-3' (SEQ ID NO: 3); His.3F: 5'-GAA GCC TCA TCG ATA CCG TC-3' (SEQ ID NO: 4); and His3R: 5'-CTA CCA CTA CCA TCA TGG C-3' (SEQ ID NO: 5). The PCR conditions were as follows: 94° C. for 5 minutes; 30 cycles of 94° C. for 30 seconds, 50° C. for 30 seconds, and 72° C. for 45 seconds; and a final extension at 72° C. for 10 minutes. Primers dCS1 and dCS2 amplify a 580 bp fragment from the δ-cadinene synthase cDNA. Primers His3F and His3R amplify a 412 bp fragment from the cotton histone 3 cDNA. PCR products were analyzed by gel electrophoresis on a 1.6% agarose gel in TBE buffer.

Example 5

Northern Hybridization Analysis

Total RNA was extracted from five pooled 35-dpa $T_2$ embryos. Denatured total RNA (18 µg) was separated by electrophoresis on a 1.5% agarose gel containing formaldehyde and transferred onto HYBOND™-N⁺ (GE Healthcare Bio-Sciences Corp., Piscataway, N.J., United States of America) membrane as described in Sambrook & Russell, 2001. A radio-labeled ($^{32}$P-dCTP) 416-bp DNA fragment PCR amplified from the 3' end of δ-cadinene synthase using the primers 5'-CAT AGG AGA GAA GAC GAT TGC TCA GC-3' (SEQ ID NO: 6) and 5'-GGA AAT GAA TAC AAA GAC AG-3' (SEQ ID NO: 7) was used as a probe. Hybridization was performed at 60° C. for 16 hours in a solution containing 0.5 M sodium phosphate buffer (pH 7.2), 1 mM EDTA, 7% SDS, and 1% BSA. Blots were washed for 10 minutes at room temperature with 2×SSC and 0.1% SDS solution followed by two washes at 60° C. for 10 minutes each with 0.5×SSC and 0.1% SDS solution.

Example 6

DNA Isolation from Immature Embryo and Mature Cottonseed Kernel

Developing embryos were collected from wild type and $T_0$ transgenic plants from the greenhouse at 35 dpa, sliced along the axis into two halves and stored in RNALATER® solution (Ambion, Austin, Tex., United States of America; Catalogue No. 7020) at −80° C. One half was used for DNA isolation while the other half was saved for RNA isolation. The immature embryo half or approximately 20 mg of the kernel powder from mature seed was transferred to a 1.5 ml microfuge tubes and further ground with a pellet pestle (Fischer Scientific International, Fair Lawn, N.J., United States of America; Catalogue No. K749520-0000) in 350 µl of extraction buffer (200 mM Tris, pH 8.0; 25 mM EDTA; 200 mM NaCl; 0.5% SDS). An additional 350 µl extraction buffer was added to the tube and the sample was mixed well. This mixture was then centrifuged at 13,000 rpm (16060×g HERAEUS® BIOFUGE® Pico, HERAEUS®, Osterode, Germany) at room temperature for 5 minutes. The supernatant was transferred to a fresh tube and extracted twice with equal volume of chloroform:isoamyl alcohol (24:1) followed by centrifugation at 5,000 rpm. The DNA from the aqueous phase was precipitated with equal volume of cold isopropanol. The DNA precipitate was lifted out with a Pasteur pipette and transferred to a fresh microfuge tube containing 1 ml of 70% ethanol. Following centrifugation at 13,000 rpm for 5 minutes, the pellet obtained was air dried and dissolved in 0.1×TE buffer. The sample was treated with DNase-free RNase at a final concentration of 20 µg/ml for 15 minutes at 37° C. The DNA was then precipitated with ¹⁄₁₀th the volume of 3 M Sodium acetate, pH 5.2 and two volumes of 100% ethanol and centrifuged at 13,000 rpm for 10 minutes. The DNA pellet was washed with 70% ethanol, air dried, and dissolved in water.

Example 7

DNA Isolation from Cotton Leaf

Approximately 200 mg leaf tissue from a newly opened cotton leaf was ground in 500 µl of extraction buffer (0.35 M glucose, 0.1 M Tris-HCl, pH 8.0, 0.005 M EDTA, 2% PVP-40; just prior to use, ascorbic acid was added to a final concentration of 1 mg/ml and β-mercaptoethanol was added to a final concentration of 2 µl/ml) in a microfuge tube using a pellet pestle. The sample was centrifuged at 13,000 rpm at 4° C. for 20 minutes. The pellet was resuspended in 400 µl of lysis buffer (0.14 M sorbitol, 0.22 M Tris-HCl (pH 8.0), 0.8 M NaCl, 0.22 M EDTA, 1% PVP-40; just prior to use, CTAB was added to a final concentration of 0.8%, ascorbic acid was added to a final concentration of 1 mg/ml, β-mercaptoethanol was added to a final concentration of 2 µl/ml, N-lauroylsarcosine was added to a final concentration of 10 mg/ml, and Proteinase K was added to a final concentration of 5 µg/ml) and incubated at 65° C. for 30 minutes. 480 µl of chloroform:isoamyl alcohol (24:1) was mixed thoroughly with the lysate followed by centrifugation at 13,000 rpm at room temperature for 20 minutes. The upper aqueous phase was transferred to a fresh microfuge tube and the DNA was precipitated with an equal volume of cold isopropanol. The DNA precipitate was lifted out with a Pasteur pipette, transferred to a fresh microfuge tube, and washed with 1 ml of 70% ethanol. Following centrifugation at 13,000 rpm for 5 minutes, the pellet obtained was air dried, dissolved in 500 µl of 0.1×TE, and treated with DNase-free RNase at a final concentration of 20 µg/ml for 15 minutes at 37° C. The DNA was then precipitated with ¹⁄₁₀th the volume of 3 M Sodium acetate, pH 5.2 and two volumes of 100% ethanol, and centrifuged at 13,000 rpm

Example 8

PCR Analysis to Detect the Intron-Containing Hairpin (ihp)-dCS Transgene

Genomic DNA (100 ng) from mature seed, immature embryo, or leaf tissue was used for PCR analysis. The following primers were used: dCS3: 5'-TCT ACA ATA GAA GCC ATT GC-3' (SEQ ID NO: 8); OCS: 5'-GCG ATC ATA GGC GTC TCG-3' (SEQ ID NO: 9). The PCR conditions were as follows: 94° C. for 5 min; 35 cycles of 94° C. for 30 seconds, 50° C. for 30 seconds, and 72° C. for 45 seconds; and a final extension at 72° C. for 10 minutes. The OCS/dCS3 primers amplified a 653-bp fragment from the genomic DNA from transgenic tissues. PCR products were analyzed by gel electrophoresis on a 1.2% agarose gel in TBE buffer.

Example 9

Southern Hybridization Analysis

Fifteen micrograms of genomic DNA, isolated following the protocol described by Chaudhry et al., 1999, was digested with EcoRI and separated on 1% agarose gel in TAE buffer. Blotting was carried out as described by Sambrook & Russell, 2001. DNA fragments specific to the nptII gene or octopine synthase terminator were used as probes. Labeling, hybridization, and posthybridization washing conditions were same as for Northern hybridization analysis.

Example 10

δ-Cadinene Synthase Enzyme Assay

Enzyme extract was prepared by grinding 1 g of 35-dpa embryos frozen in liquid nitrogen following the procedure described by Martin et al., 2003. The enzyme assay was performed in a 300 µl reaction mixture containing 255 µl of enzyme extract, 27 mM potassium fluoride, 1 mM magnesium chloride, 200 µM (1RS)-[1-$^2$H]-(E,E)-farnesyl diphosphate (FDP) at 30° C. for 20 minutes. The reaction mix was then extracted with 300 µl of hexane:ethyl acetate (3:1). One microliter of the organic phase was analyzed for deuterated δ-cadinene by a GC-MS instrument fitted with an AGE BP1 (25×0.25-mm) column. The sample was run in a splitless mode with an injector temperature of 250° C. The initial temperature of the instrument was 40° C., and the temperature was increased at a rate of 10° C. min$^{-1}$ until 180° C., followed by 20° C. min$^{-1}$ up to 270° C. (1 minute hold). The flow of helium was constant at 1 ml min$^{-1}$. The area of the peak (total ions) corresponding to δ-cadinene was used as a measure of enzyme activity.

Discussion of the EXAMPLES

Gossypol and other sesquiterpenoids are derived from (+)-δ-cadinene. The enzyme δ-cadinene synthase catalyzes the first committed step involving the cyclization of farnesyl diphosphate to (+)-δ-cadinene (see FIG. 1). Disclosed herein is the discovery that disrupting the cadinane sesquiterpenoid biosynthesis exclusively in the seed at this point in the pathway does not have any undesirable consequences. A 604 bp sequence from a δ-cadinene synthase cDNA clone obtained from a *Gossypium hirsutum* developing embryo library was chosen as the trigger sequence (see FIG. 2). The selected portion of the clone has 80.9 to 99.8% homology to several other published sequences of δ-cadinene synthase genes from the diploid (G. arboreum) and tetraploid (G. hirsutum) cottons (Chen et al., 1995; Townsend et al., 2005; see also Table 1).

Figure 4:
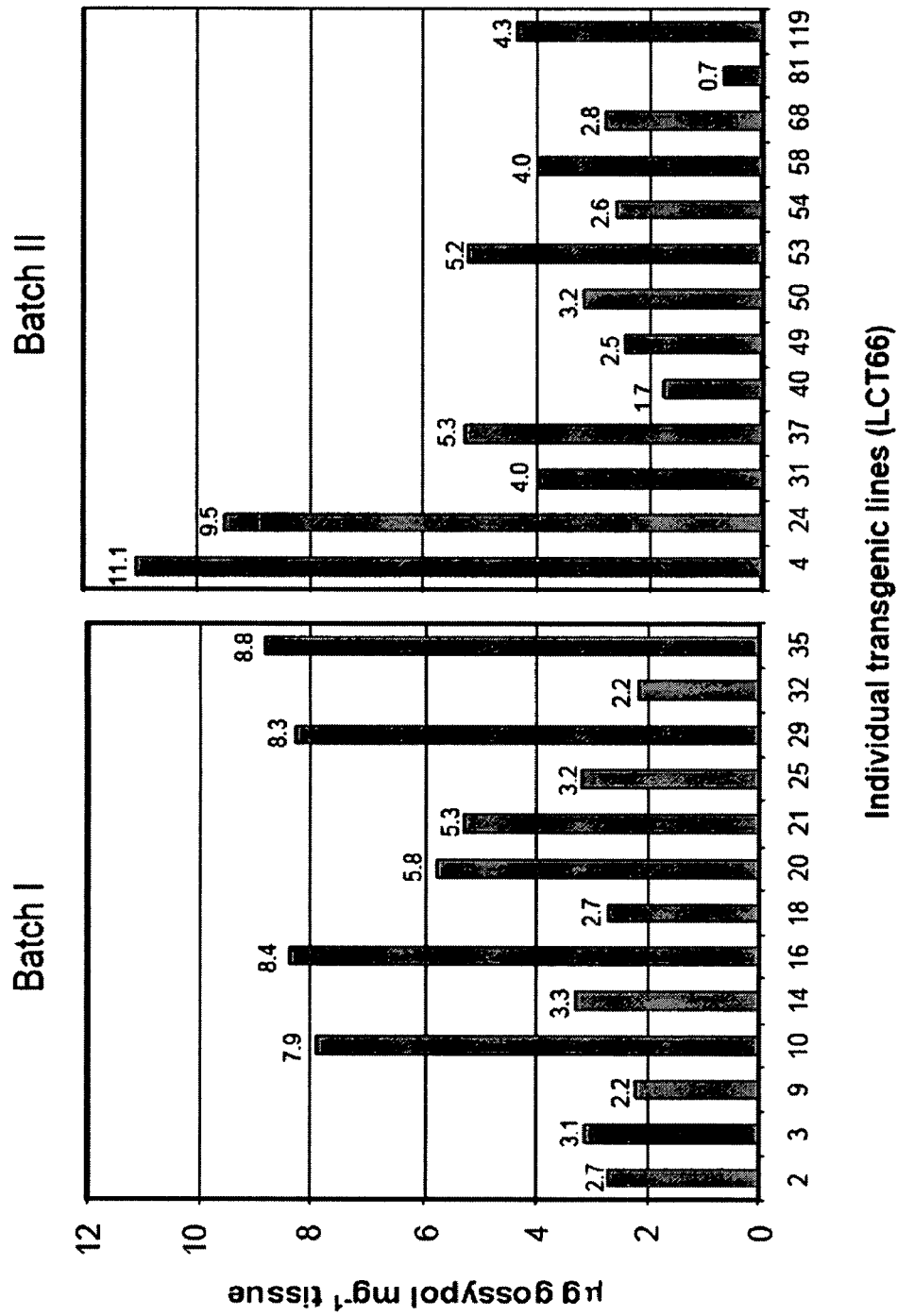
FIG. 4 is a set of two bar graphs showing levels of gossypol in pooled samples of 30 mature $T_1$ seeds from 26 independent transgenic lines. The results presented are for two separate batches of transgenic plants recovered at different stages of the project. Note that the $T_1$ seeds are segregating for the transgene, and therefore the gossypol levels in the pooled seeds presented here also includes the values from the contaminating null segregant seeds.

This trigger sequence is expected to target some or all members of the δ-cadinene synthase gene family including Cad1-A, as it bears several stretches (20-35 bp) of perfect homology to these sequences (see FIG. 13 for an alignment of the sequences cited in Table 1). An intron-containing hairpin (ihp) transformation construct was made using the pHANNI-BAL/pART27 system (Smith et al., 2000; Wesley et al., 2001; see FIG. 3). The transcription of the ihpRNA sequence was under the control of a highly seed-specific α-globulin B gene promoter from cotton (Sunilkumar et al., 2002). Cotton (*G. hirsutum*, cv. Coker 312) was transformed using the *Agrobacterium tumefaciens* method (Rathore et al., 2006) and the transgenic T$_0$ plants were grown to maturity in a greenhouse. A pooled sample of 30 T$_1$ seeds from each of the 26 independent transgenic lines was analyzed by HPLC for gossypol (Stipanovic et al., 1988), which is the predominant form of terpenoid in this tissue. Several of these lines produced seeds with significantly low levels of gossypol (see FIG. 4).

Figure 5A:
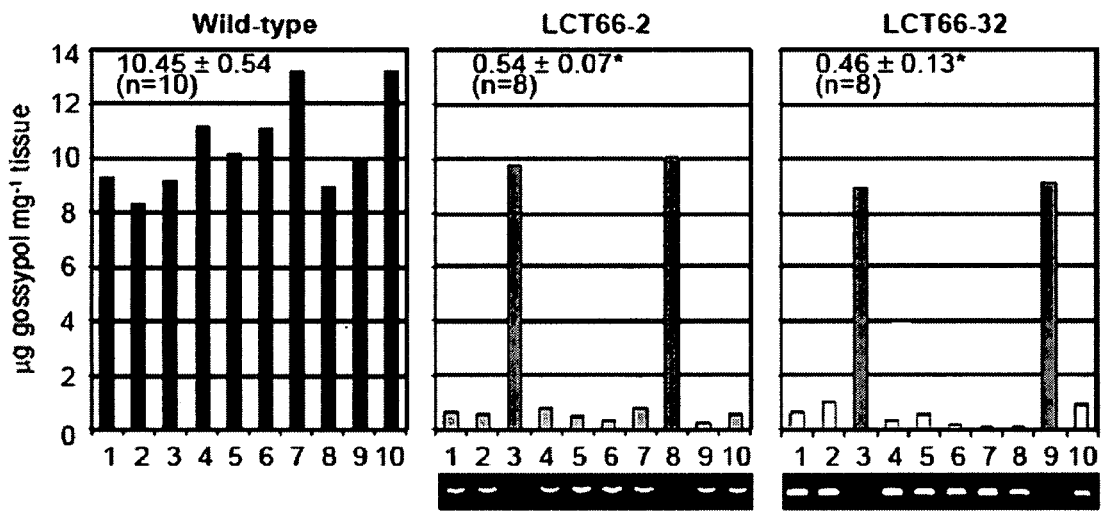
FIGS. 5A and 5B present the results of experiments that showed reductions in gossypol levels in the transgenic cottonseeds from RNAi lines.

Ten mature T1 seeds each from eight of these selfed T$_0$ lines, which were regenerated from the first batch of transformation experiments, were individually analyzed for gossypol. The results from two of these lines (LCT66-2 and LCT66-32) along with 10 wild type control seeds are shown in FIG. 5A.

Figure 5B:
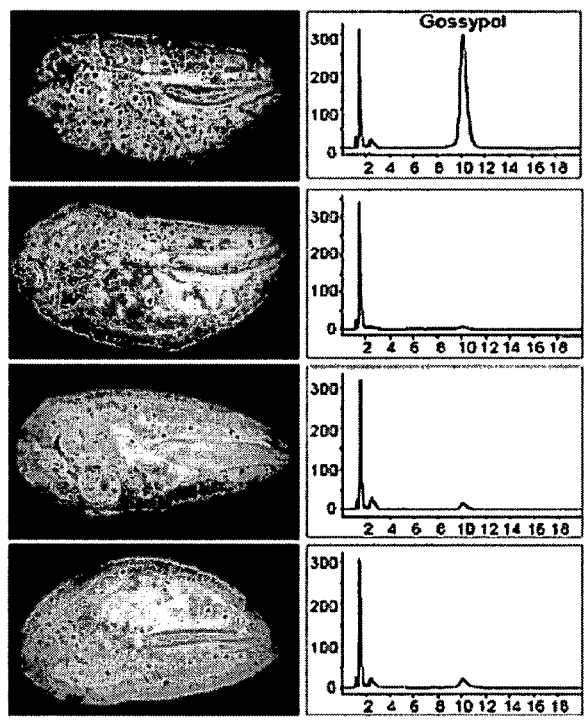

All transgene-containing mature seeds, identified by PCR analysis, showed a dramatic and significant reduction in the level of gossypol. The co-segregation of the reduced seed-gossypol trait with the presence of the transgene was unambiguous. The null segregant seeds did not show any reductions in the gossypol levels. Also, the low gossypol phenotype is clearly noticeable in lighter colored and smaller sized glands in the transgenic seeds (see FIG. 5B). Compared to an average gossypol value of 10 µg/mg in wild type seeds, individual transgenic seeds showed values as low as 0.1 µg/mg, a 99% reduction.

Figure 6:
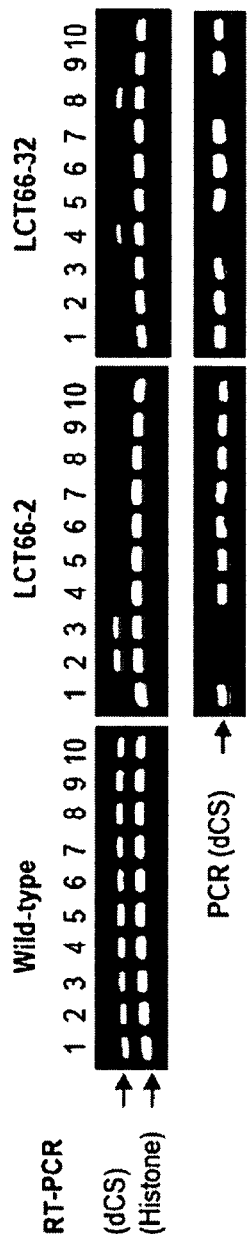
FIG. 6 is a set of photographs depicting the results of RT-PCR analyses showing reductions in δ-cadinene synthase (dCS) expression levels in the transgenic, developing embryos from RNAi lines. RT-PCR analysis in 10 individual, developing embryos (35 dpa) each from wild type control plants and the two RNAi transgenic lines. Transcripts from histone 3 gene of cotton were amplified as internal controls in the duplex RT-PCR analyses. The results from PCR analysis on DNA from the same individual embryos from the RNAi lines are also shown to illustrate a correlation between reduced dCS transcripts with the presence of the transgene.

The activity of the target δ-cadinene synthase gene is expected to be high in the developing cotton embryos around 35 days post anthesis (dpa; Meng et al., 1999). RT-PCR analyses were conducted to determine the levels of δ-cadinene synthase transcripts during this stage in developing embryos from wild type control plants and the two transgenic lines. The presence of the transgene in the embryos from the transgenic lines was independently confirmed by PCR. The results presented in FIG. 6 clearly showed the suppression of δ-cadinene synthase gene activity in the transgene-containing embryos from the two transgenic lines. As expected, the transcript levels in the null segregant embryos were similar to control values suggesting that they remained unaffected by the neighboring embryos that were undergoing RNAi-induced silencing. Thus, the molecular data supported and confirmed results of the biochemical analysis presented earlier.

Genomic DNA from three lines that were characterized more extensively were subjected to Southern blot analysis, and the results showed integration of the transgene in the genomes of these lines (see FIG. 7).

Figure 8:
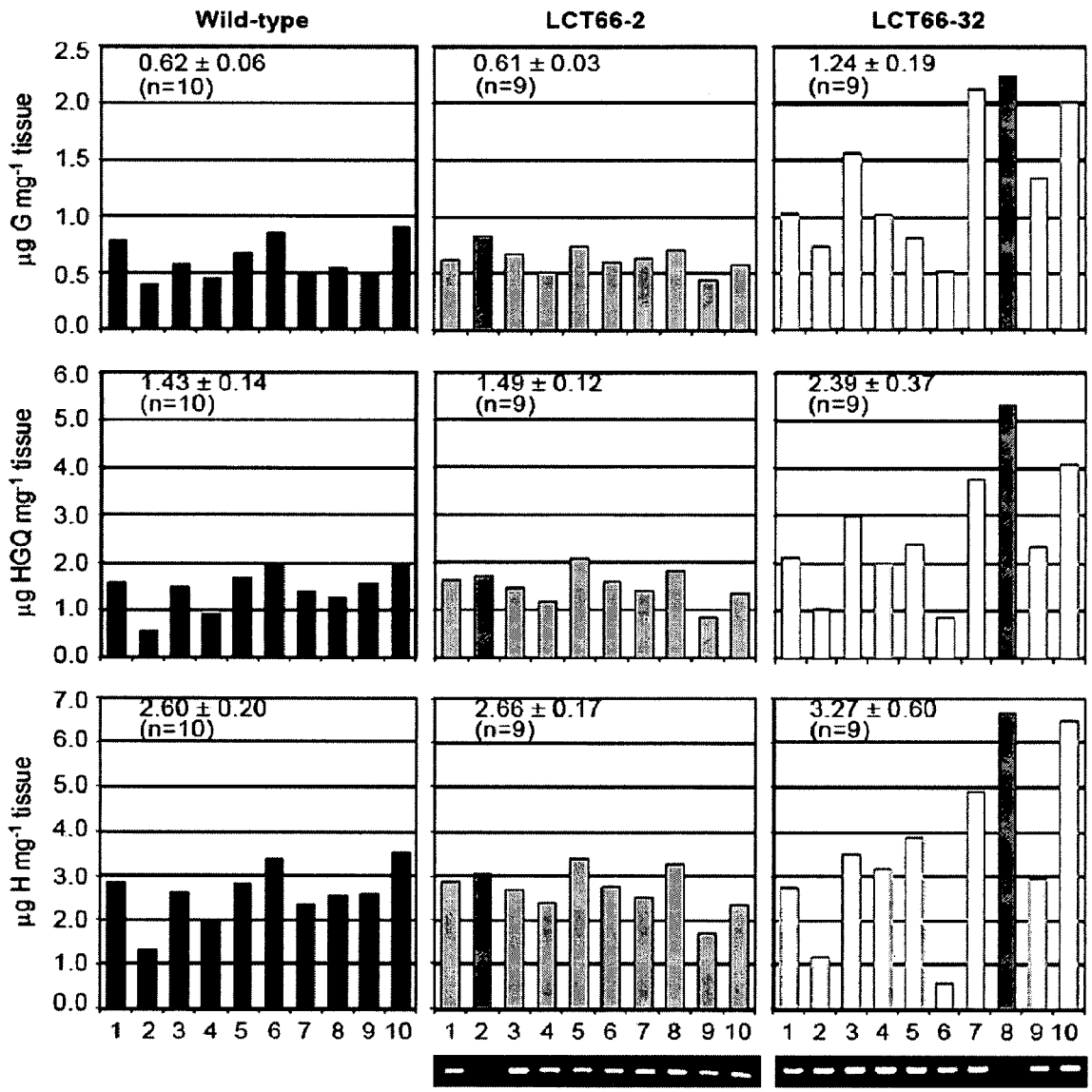
FIG. 8 is a set of bar graphs and photographs showing that the levels of gossypol and related terpenoids in the foliage of transgenic progeny from RNAi lines are not reduced. The levels of gossypol (G), hemigossypolone (HGQ), and, total heliocides (H) in leaf tissues from 10 individual wild type control plants and the T1 progeny of the two RNAi transgenic lines. The results from PCR analysis on DNA from the same individual progeny plants from the RNAi lines are depicted under the respective graphs. Mean (±s.e.m.) values for terpenoid levels in the leaf tissue of control plants (n=10) and the transgene bearing T1 plants (n=9) from each of the transgenic lines are shown with the respective graphs. The key to the bar shading is as in FIG. 5A.

The terpenoid present in cottonseed is almost exclusively gossypol, whereas in the leaf, hemigossypolone and heliocides H$_1$, H$_2$, H$_3$, and H$_4$ occur together with gossypol. These compounds are derived from the same biosynthetic pathway (see FIG. 1) and their presence and induction in the aerial parts protects the cotton plant from insects and diseases (Hedin et al., 1992; Stipanovic et al., 1999). The leaves from transgenic and control plants were examined for the levels of these protective compounds. A different batch of 10 seeds from each of the transgenic lines and 10 wild type control seeds were germinated and grown in soil in a greenhouse and leaf tissue from each was analyzed for terpenoids (Benson et al., 2001). The levels of gossypol, hemigossypolone, and heliocides in the foliage of control and T1 transgenic plants are presented in FIG. 8. Transgene-bearing plants were identified by PCR analysis. The data showed clearly that the presence of the transgene, which resulted in a significant reduction in gossypol in the seed, did not diminish gossypol and related terpenoids in the leaves. Moreover, levels of the other protective terpenoids, hemigossypolone and the heliocides, were not reduced in the leaves of transgenic plants.

Figure 9:
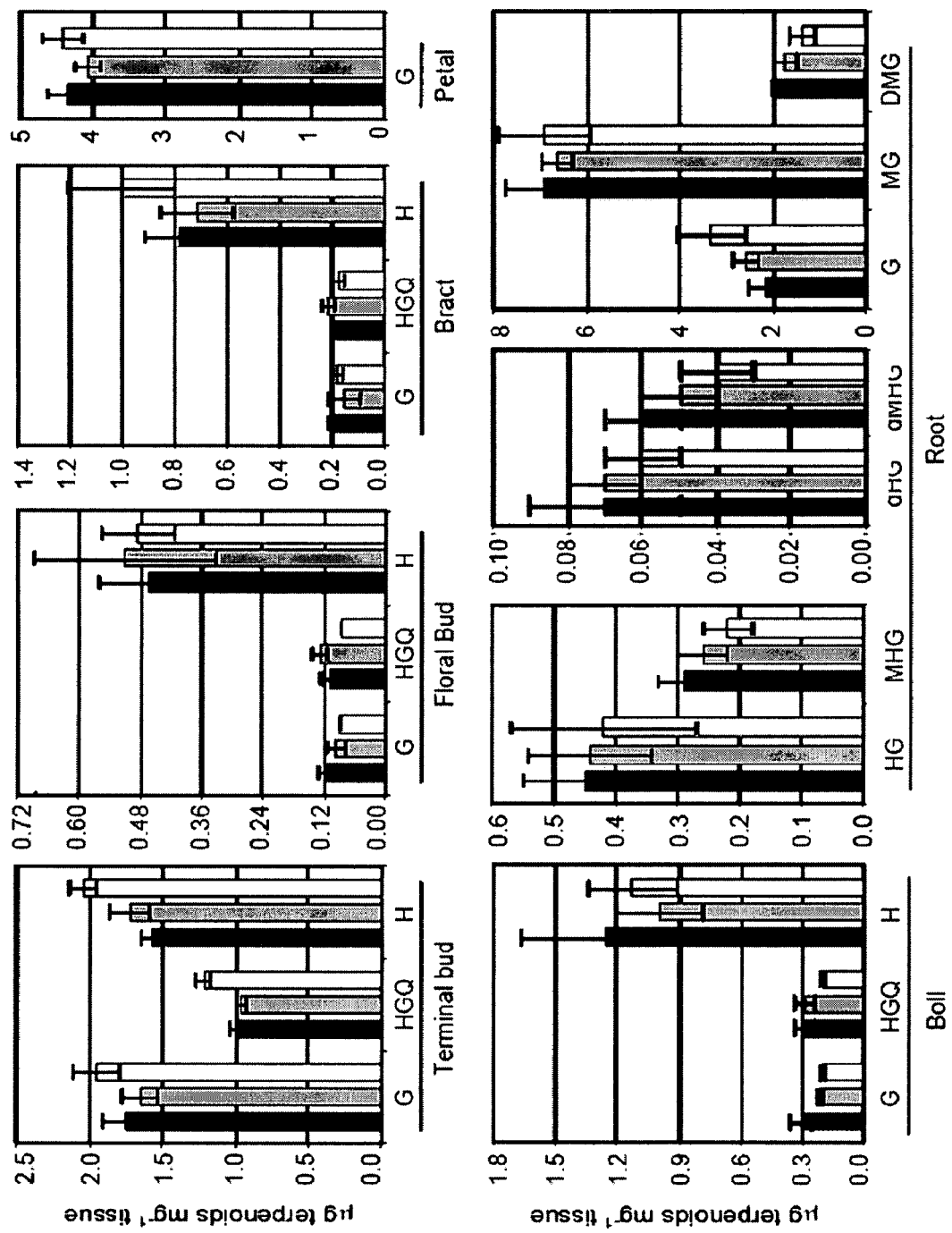
FIG. 9 is a set of bar graphs showing that the levels of gossypol and related terpenoids in terminal buds, bracts, floral organs, bolls, and roots of transgenic progeny from RNAi lines are not reduced. The levels of terpenoids in various organs of wild type control plants (black bar), $T_1$ transgenic progeny from RNAi line LCT66-2 (light gray bar), and $T_1$ transgenic progeny from RNAi line LCT66-32 (white bar). The results shown are mean (±s.e.m.) terpenoid values in tissue samples taken from three individual plants in each category. Note that in petals, gossypol was the only terpenoid detected and in the root tissue, the terpenoids detected were: gossypol (G), gossypol-6-methyl ether (MG), gossypol-6,6'-dimethyl ether (DMG), hemigossypol (HG), desoxyhemigossypol (dHG), hemigossypol-6-methyl ether (MHG), and desoxyhemigossypol-6,6'-methyl ether (dMHG).

In addition to the leaves, other tissues that are targeted by insects as well as roots were also examined for terpenoid levels. The levels of the protective terpenoids were not reduced in the terminal buds, bracts (epicalyx), floral buds, petals, bolls, and roots in the progeny from the RNAi transgenic lines compared to the values observed in the wild type plants (see FIG. 9). Taken together, the results show that the low-gossypol phenotype is seed-specific and therefore, the terpenoid-dependent defensive capabilities should not be compromised in the transgenic lines. Thus, by using modern molecular tools, the major shortcoming of the glandless cotton previously created via conventional breeding has been overcome.

Figure 10:
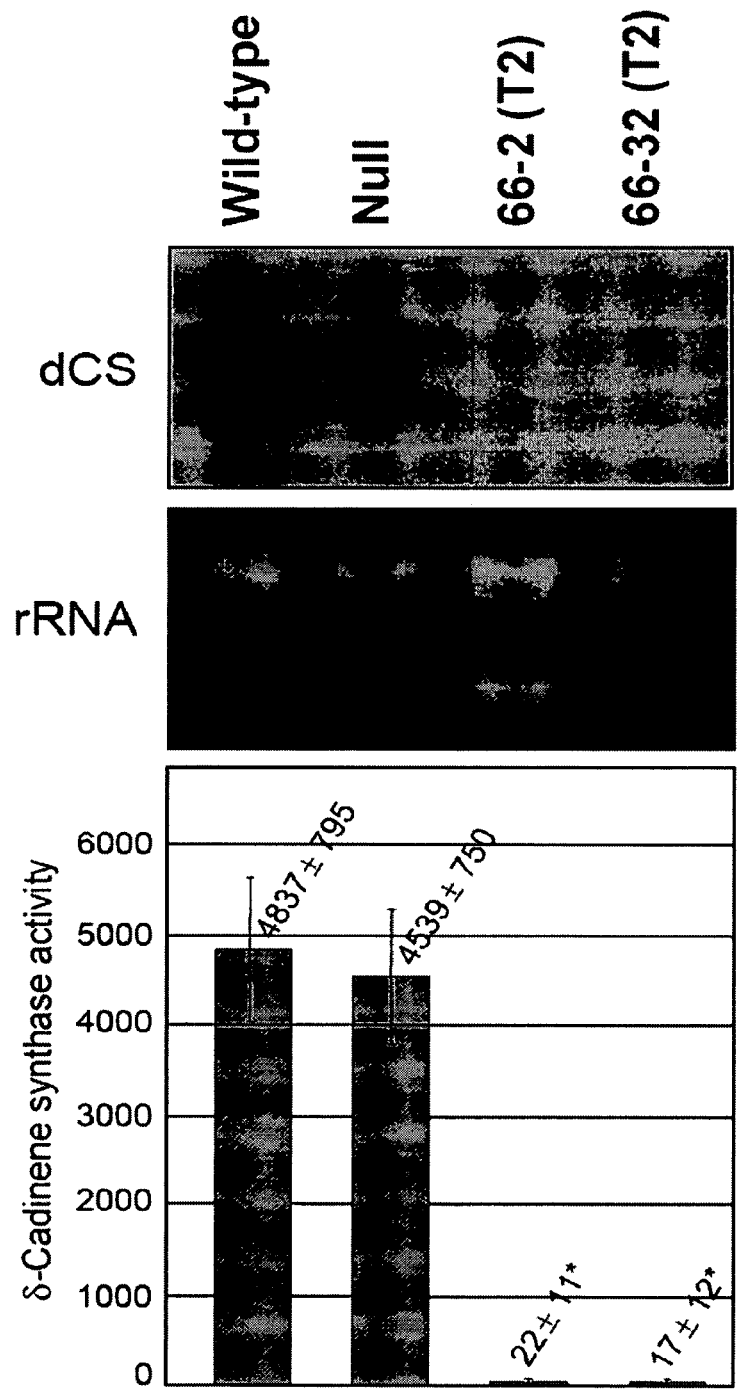
FIG. 10 is an autoradiograph, a photograph, and a bar graph showing that the δ-cadinene synthase transcripts and enzyme activities are significantly reduced in developing embryos from the RNAi lines. Separate sets of embryos (35 dpa) isolated from wild type plants, null segregant plants, and homozygous $T_1$ plants from lines LCT66-2 and LCT66-32 were used for each type of analysis. (Top) The hybridization band (dCS) on a Northern blot; (Middle) ethidium bromide-stained RNA gel before blotting; (Bottom) δ-cadinene synthase activities. The enzyme activity is presented as total ion peak area of δ-cadinene generated min-1 mg-1 embryo. Enzyme activity results are mean (±s.e.m.) of values obtained from three separate sets of embryo samples from each type of plant. *, The value for the transgenic line is significantly different from the control (wild type and null segregant) value at P=0.004.

Homozygous T1 progeny from transgenic lines LCT66-2 and LCT66-32 and null segregant plants of the same generation were identified and grown in the greenhouse. Developing embryos (35 dpa) from these plants and wild type control plants were examined for the δ-cadinene synthase transcripts and enzyme activities. The data showed significant reductions for both the target message and enzyme activity (see FIG. 10), thus confirming the results of RT-PCR analyses discussed hereinabove and lending support to the notion that the low-gossypol cottonseed phenotype was due to targeted knockdown of the δ-cadinene synthase gene.

Figure 11:
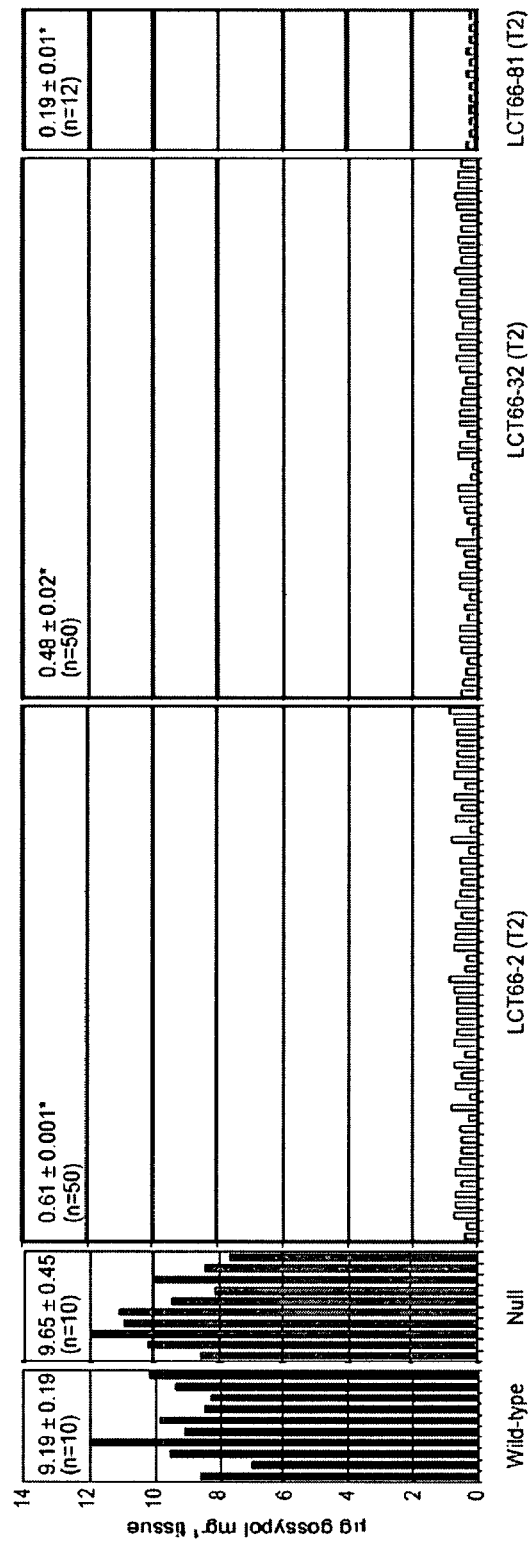
FIG. 11 is a set of bar graphs showing that the low-seed-gossypol trait is successfully transmitted to $T_2$ generation seeds in the transgenic RNAi lines. Gossypol levels in: 10 individual seeds each from wild type control plant and a null segregant plant; 50 individual $T_2$ seeds each from homozygous $T_1$ plants that were derived from their respective parental transgenic lines, LCT66-2 and LCT66-32; and 12 individual $T_2$ seeds from homozygous $T_1$ plant that was derived from the parental transgenic line LCT66-81. Mean (±s.e.m.) gossypol values for control and transgenic seeds are shown with the respective graphs. *, The value for the transgenic line is significantly different from the control (wild type and null segregant) value at P=0.001.
Figure 12:
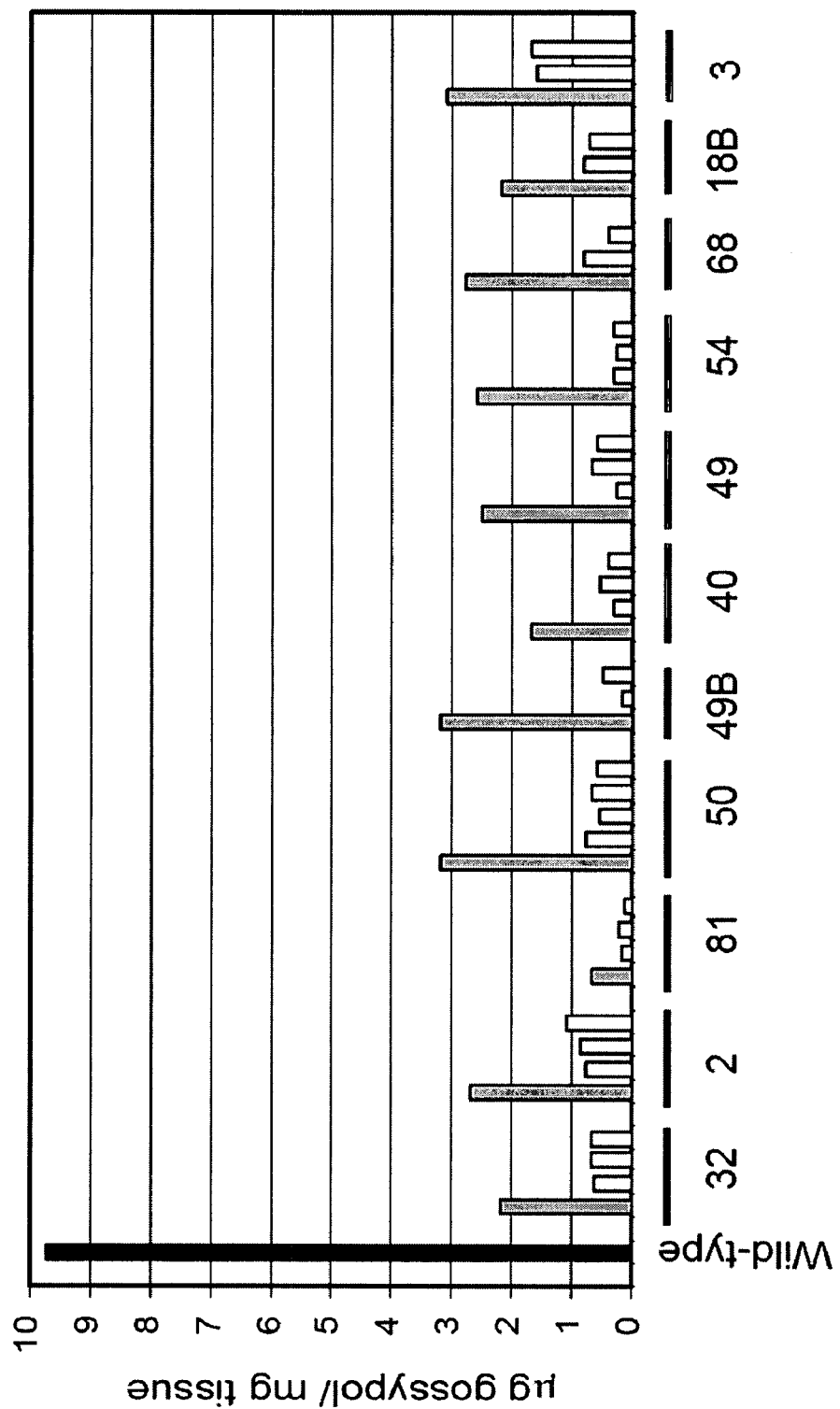
FIG. 12 is a bar graph showing that the low seed-gossypol trait is inherited and maintained in the $T_2$ generation in 11 different transgenic lines. Black bar: Gossypol level in a pooled sample of 30 seeds from wild type control plants. Gray bar: Gossypol level in a pooled sample of 30 $T_1$ seeds that were obtained from each of the 11 transgenic lines. White bar.

In order to confirm stability of the transgenic trait, homozygous $T_1$ progeny from transgenic lines LCT66-2, LCT66-32 and LCT66-81 were grown to maturity in the greenhouse and individual $T_2$ seeds obtained from these plants were analyzed for gossypol levels. The results from these analyses showed clearly that the low seed-gossypol trait was successfully inherited and stably maintained in both RNAi lines (see FIG. 11). The United Nations Food and Agriculture Organization and World Health Organization (FAO/WHO) permit up to 0.6 μg/mg (600 ppm) free gossypol in edible cottonseed products (Lusas & Jividen, 1987). The levels of gossypol in the seeds from the RNAi lines fell within these safety limits. Gossypol analyses performed using pooled samples of $T_2$ seeds obtained from these three (LCT66-2, LCT66-32 and LCT66-81) and an additional eight transgenic lines further confirmed that the low seed-gossypol trait is inherited and maintained in the $T_2$ generation (see FIG. 12).

Extensive efforts in several laboratories over the last decade to eliminate gossypol from cottonseed using antisense method have proven unsuccessful (Townsend et al., 2005), resulted in small reduction in seed gossypol, or provided ambiguous results (Martin et al, 2003; Benedict et al., 2004). Disclosed herein is an RNAi approach coupled with a tissue-specific promoter that can be employed to significantly and selectively reduce the toxic terpenoid gossypol from cottonseed without diminishing the levels of this and related defensive terpenoids in parts of the plant usually attacked by insects.

Several lines of evidence suggest that RNAi-mediated silencing remains confined to the tissues that express the hpRNA-encoding transgene in cotton. The null segregant embryos, which are developing within the same ovary as the transgene-bearing silenced embryos, remain unaffected in their levels of the transcripts corresponding to the target gene (see FIG. 6). Furthermore, gossypol levels in the mature null segregant seeds were not reduced (see FIGS. 5A and 5B). These results showed that the silenced status of transgenic embryos did not spread to the neighboring null segregant embryos, suggesting that individual embryos developed in seclusion and were not influenced by the RNAi-induced, silenced status of the neighboring embryos. Taken together, the results disclosed herein suggested that the silencing signal from the developing, δ-cadinene synthase-suppressed cotton embryo would be unlikely to spread and reduce the levels of terpenoids in non-target tissues, such as the foliage, roots, etc.

The results described herein also demonstrate that targeted gene silencing can be used to modulate biosynthetic pathways in a particular tissue in a way that is not possible by traditional breeding.

Gossypol values in the seeds from some of the lines are well below the limit deemed safe for human consumption by FAO/WHO. Thus, cotton, that has served the clothing needs of humanity for millennia, has the potential to make a significant contribution to its nutritional requirements.

While exemplary embodiments of the presently disclosed subject matter have been shown and described, modifications thereof can be made by one skilled in the art without departing from the spirit and teachings of the presently disclosed subject matter. For example, in addition to the representative methods set forth herein, it can be possible to reduce gossypol in cottonseed by targeting a different enzyme involved in the biosynthesis of gossypol by using a different seed-specific promoter. It is also possible to prevent gland formation in the seed to eliminate gossypol by seed-specific knockout of genes involved in the gland formation.

REFERENCES

The disclosures of the references listed below, as well as all other references cited in the specification, including but not limited to patents, patent applications, scientific publications, and database entries (e.g., GENBANK® entries, including all annotations and references cited therein), are hereby incorporated herein by reference to the extent that they describe materials, methods, or other details supplementary to those set forth herein.

Agrawal S (ed.) *Methods in Molecular Biology*, volume 20, Humana Press, Totowa, N.J., United States of America.
Alford et al. (1996) *Iant Foods Hum Nutr* 49:1-11.
Allison et al. (1986) *Virology* 154:9-20.
Altschul et al. (1990) *J Mol Biol* 215:403-410.
Aoyama & Chua (1997) *Plant J* 11:605-12.
Aravin et al. (2003) *Dev Cell* 5:337-350.
Ausubel et al., eds (1989) *Current Protocols in Molecular Biology*. Wiley, New York, N.Y., United States of America.
Bartel & Bartel (2003) *Plant Physiol* 132:709-717.
Bartel (2004) *Cell* 116:281-297.
Benedict et al. (2004) *Phytochem* 65:1351-1359.
Benson et al. (2001) *J Agric Food Chem* 49:2181-2184.
Bernstein et al. (2001) *Nature* 409:363-366.
Bevan (1984) *Nucl Acids Res* 12:8711.
Bevan et al. (1983) *Nature* 304:184-187.

Binet et al. (1991) *Plant Mol Biol* 17:395-407.
Blochinger & Diggelmann (1984) *Mol Cell Biol* 4:2929-2931.
Bottger et al. (1964) *J Econ Ento* 57:283-285.
Bourouis & Jarry (1983) *EMBO J* 2:1099-1104.
Bressani (1965) *Food Technol* 19:1655-1662.
Caddick et al. (1998) *Nat Biotechnol* 16:177-80.
Callis et al. (1987) *Genes Dev* 1:1183-1200.
Canadian Patent Application No 2,359,180.
Chaudhry et al. (1999) *Plant Mol Biol Rep* 17:1-7.
Chen et al. (1995) *Arch Biochem Biophys* 324:255-266.
Chenoweth et al. (1994) *Theriogenol* 42:1-13.
Chibbar et al. (1993) *Plant. Cell Rep* 12:506-509.
Christensen & Quail (1989) *Plant Mol Biol* 12:619-632.
Chuang & Meyerowitz (2000) *Proc Natl Acad Sci USA* 97:4985-90.
de Framond (1991) *FEBS Lett* 290:103-106.
De Onis et al. (1993) *Bull World Health Organ* 71:703-712.
Della-Cioppa et al. (1987) *Plant Physiol* 84:965.
Ebel et al. (1992) *Biochem* 31:12083-12086.
Elbashir et al. (2001a) *Nature* 411:494-498.
Elbashir et al. (2001b) *Genes Dev* 15:188-200.
Elbashir et al. (2001c) *EMBO J* 20:6877-88.
Elbashir et al. (2002) Analysis of gene function in somatic mammalian cells using small interfering DNAs, *Methods* 26:199-213.
Elroy-Stein et al. (1989) *Proc Natl Acad Sci USA* 86:6126-30.
European Patent Application Publications EP 0 332 104 and EP 0 392 225.
Fire (1999) *Trends Genet* 15:358-363.
Fire et al. (1998) *Nature* 391:806-811.
Firek et al. (1993) *Plant Mol Biol* 22:129-142.
Freier et al. (1986) *Proc Natl Acad Sci USA* 83:9373-9377.
Gallie et al. (1987) *Nucl Acids Res* 15:8693-8711.
Gallie et al. (1989) *Plant Cell* 1:301.
Goeddel (1990) in *Methods in Enzymology*, Volume 185, Academic Press, San Diego, Calif., United States of America.
Gritz & Davies (1983) *Gene* 25:179.
Hamilton & Baulcombe (1999) *Science* 286:950-952.
Hammond et al. (2000) *Nature* 404:293-296.
Hedin et al. (1992) *J Econ Entomol* 85:359-364.
Henikoff & Henikoff (1992) *Proc Natl Acad Sci USA* 89:10915-10919.
Höfgen & Willmitzer (1988) *Nucl Acids Res* 16:9877.
Hudspeth & Grula (1989) *Plant Molec Biol* 12:579-589.
Hutvágner & Zamore (2002) *Curr Opin Genet Dev* 12:225-232.
Hutvágner et al. (2000) *RNA* 6:1445-1454.
Jenkins et al. (1966) *J Econ Entomol* 59:352-356.
Jobling & Gehrke (1987) *Nature* 325:622.
Karlin & Altschul (1993) *Proc Natl Acad Sci USA* 90:5873-5877.
Kasschau et al. (2003) *Dev Cell* 4:205-217.
Klein et al. (1988) *Bio/Technology* 6:559.
Kong & Steinbiss (1998) *Arch Virol* 143:1791-1799.
Lagos-Quintana et al. (2001) *Science* 294:853-858.
Lagos-Quintana et al. (2002) *Curr Biol* 12:735-739.
Lambou et al. (1966) *Economic Botany* 20:256-267.
Lau et al. (2001) *Science* 294:858-862.
Lebel et al. (1998) *Plant J* 16:223-33.
Lee & Ambros (2001) *Science* 294:862-864.
Lee et al. (1993) *Cell* 75:843-854.
Lee et al. (2003) *Nature* 425:415-419.
Lee Y et al. (2002) *EMBO J* 21:4663-4670.
Lim et al. (2003b) *Genes Dev* 17:991-1008.
Llave et al. (2002). *Science* 297:2053-2056.
Logemann et al. (1989) *Plant Cell* 1:151-158.
Lommel et al. (1991) *Virology* 181:382.
Lusas & Jividen (1987) *J Amer Oil Chem Soc* 64:839-854.
Macejak & Sarnow, (1991) *Nature* 353:90-94.
Martin et al, (2003) *Phytochem* 62:31-38.
McBride et al. (1990) *Plant Mol. Biol.* 14: 266.
McElroy et al. (1990) *Plant Cell* 2:163-71.
McElroy et al. (1991) *Mol Gen Genet* 231:150-160.
McMichael (1954) *Agron J* 46:527-528.
McMichael (1959) *Agron J* 51:630.
McMichael (1960) *Agron J* 52:385-386.
Meng et al. (1999) *J Nat Prod* 62:248-252.
Messing & Viera (1982) *Gene* 19:259.
Miravalle & Hyer (1962) *Crop Sci* 2:395-397.
Needleman & Wunsch (1970) *J Mol Biol* 48:443-453.
Nykanen et al. (2001) *Cell* 107:309-321.
Paszkowski et al. (1984) *EMBO J.* 3:2717.
PCT International. Publication Nos WO 93/07278; WO 97/43430; WO 99/32619; WO 99/53050; WO 99/61631; WO 00/44914; WO 00/53783; WO 00/63364; WO 00/77230; WO 01/04313; WO 01/36646; WO 01/68836; WO 01/75164; WO 01/92513; WO 02/055692; WO 02/44321; and WO 02/055693; and WO 03/052111.
Pearson & Lipman (1988) *Proc Natl Acad Sci USA* 85:2444-2448.
Potrykus (1985) *Trends Biotech.* 7:269.
Rathore et al. (2006) in *Methods in Molecular Biology, Vol. 343: Agrobacterium Protocols*. $2^{nd}$ Ed., Vol. 1, Wang (ed.), Humana Press Inc., Totowa, N.J., United States of America, pp. 267-279.
Reinhart et al. (2002) *Genes Dev* 16:1616-1626.
Rhoades et al. (2002) *Cell* 110:513-520.
Risco & Chase Jr (1997) in *Handbook of Plant and Fungal Toxicants* (D'Mello, ed.), CRC Press, Boca Raton, Fla., United States of America, pp. 87-98.
Rohrmeier & Lehle (1993) *Plant Mol Biol* 22:783-792.
Rothstein et al. (1987) *Gene* 53:153.
Sambrook & Russell (2001) *Molecular Cloning: A Laboratory Manual*, 3rd ed. Cold Spring Harbor Laboratory Press, Cold Spring Harbor, N.Y.
Sambrook & Russell (2001) *Molecular Cloning: A Laboratory Manual, Third Edition*, Cold Spring Harbor Laboratory Press, Cold Spring Harbor, N.Y., United States of America.
Schmidhauser & Helinski (1985) *J Bacteriol* 164:446.
Schwab et al. (2006) *Plant Cell* 18:1121-1133.
Skuzeski et al. (1990) *Plant Mol Biol* 15:65-79.
Smith & Waterman (1981) *Adv Appl Math* 2:482-489.
Smith et al. (2000) *Nature* 407:319-320.
Song et al. (2000) *J Cotton Sci* 4:217-223.
Spencer et al. (1990) *Theor Appl Genet* 79:625.
Stipanovic et al. (1988) *J Agric Food Chem* 36:509-515.
Stipanovic et al. (1999) in *Biologically Active Natural Products—Agrochemicals* (Cutler & Cutler, eds.), CRC Press, Boca Raton, Fla., United States of America, pp. 211-220.
Sunilkumar & Rathore (2001) *Mol Breeding* 8:37-52.
Sunilkumar et al. (2002) *Transgenic Res* 11:347-359.
Thompson et al. (1987) *EMBO J.* 6:2519.
Tibanyenda et al. (1984) *Eur J Biochem* 139:19-27.
Tijssen (1993) *Laboratory Techniques in Biochemistry and Molecular Biology—Hybridization with Nucleic Acid Probes*. Elsevier, N.Y., United States of America.
Townsend & Llewellyn (2002) *Funct Plant Biol* 29:835-843.
Townsend et al. (2005) *Plant Physiol* 138:516-528.
Turner et al. (1987) *Cold Spring Harb Symp Quant Biol LII:* 123-133.
U.S. Patent Application Publication No. 20030154516.

Uknes et al. (1992) *Plant Cell* 4:645-656.
Uknes et al. (1993) *Plant Cell* 5:159-169.
U.S. Pat. Nos. 4,940,935; 4,945,050; 5,004,863; 5,036,006; 5,100,792; 5,159,135; 5,164,310; 5,188,642; 5,188,960; 5,338,544; 5,466,785; 5,474,925; 5,495,070; 5,521,078; 5,523,311; 5,597,718; 5,602,321; 5,608,142; 5,608,148; 5,614,395; 5,620,882; 5,633,435; 5,639,949; 5,767,378; 5,827,514; 5,846,797; 5,869,720; 5,880,275; 5,929,300; 5,981,834; 5,986,181; 5,994,629; 5,998,207; 6,054,318; 6,107,549; 6,218,188; 6,308,458; 6,329,570; 6,423,885; 6,448,476; 6,472,588; 6,479,287; 6,483,013; 6,506,559; 6,559,363; 6,563,022; 6,573,437; 6,620,990; 6,624,344; 6,660,914; 6,703,540; 6,710,228; 6,730,824; 6,753,463; 6,818,807; 6,858,777; 6,943,282; 6,974,898; 7,005,423; 7,041,877; 7,053,270; 7,091,400; 7,138,565; and 7,122,722.

Warner et al. (1993) *Plant J* 3:191-201.
Waterhouse et al. (2001) *Nature* 411:834-842.
Wesley et al. (2001) *Plant J* 27:581-590.
White et al. (1990) *Nucl Acids Res* 18:1062.
Wianny & Zernicka-Goetz (1999) *Nature Cell Biol* 2:70-75.
Wightman et al. (1993) *Cell* 75:855-862.
Xu et al. (1993) *Plant Mol Biol* 22:573-588.
Zeng & Cullen (2003) *RNA* 9:112-123.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for reducing the level of gossypol in a seed of a cotton plant, the method comprising expressing in the seed a heterologous nucleic acid construct comprising a DNA sequence comprising at least 20 consecutive nucleotides of SEQ ID NO:1 and the reverse complement thereof operably linked to a seed-specific promoter DNA sequence, whereby RNA interference is substantially absent in parts of the cotton plant other than the seed, and wherein said expressing induces RNA interference-mediated reduction of gossypol levels in the seed.

2. The method of claim 1, wherein a level of gossypol in a tissue selected from the group consisting of foliage, leaves, bracts, buds, bolls, and roots of the treated cotton plant is substantially identical to the level of gossypol in a same tissue of a cotton plant not expressing the heterologous nucleic acid construct.

3. The method of claim 1, wherein the level of at least one terpenoid other than gossypol in a tissue selected from the group consisting of foliage, leaves, bracts, buds, bolls, and roots of the treated cotton plant is substantially identical to the level of the same at least one terpenoid in the same tissue of a cotton plant not expressing the heterologous nucleic acid construct.

4. The method of claim 1, wherein the heterologous nucleic acid construct comprises a transgene comprising a first nucleotide sequence, an intervening sequence, and a second nucleotide sequence comprising the reverse-complement of the first nucleotide sequence, and further wherein transcription of the transgene produces a hairpin RNA molecule comprising:
  (a) a double stranded region comprising an intermolecular hybridization of the first and second nucleotide sequences; and
  (b) a single stranded region comprising at least a part of the intervening sequence.

5. A method for producing a transgenic cotton plant bearing seed with a reduced gossypol content, the method comprising:
  (a) stably transforming a host cotton plant cell with an expression construct comprising a seed-specific promoter sequence operably linked to a DNA sequence comprising at least 20 consecutive nucleotides of SEQ ID NO:1 and the reverse-complement thereof;

(b) regenerating a transgenic plant from the stably transformed host cotton plant cell; and (c) growing the transgenic plant under conditions whereby seed that express the expression construct are produced, wherein the seed have a reduced gossypol content as a result of the expression of the construct in the seed.

6. The method of claim 5, wherein the seed-specific promoter sequence comprises a nucleotide sequence as set forth in one of SEQ ID NOs: 10-12.

7. The method of claim 5, wherein expression of the DNA sequence disrupts cadinane sesquiterpenoid biosynthesis in the seed to a greater extent than it does in the foliage of the plant.

8. An expression cassette comprising:
(a) a seed-specific promoter;
(b) DNA sequence comprising at least 20 consecutive nucleotides of SEQ ID NO:1;
(c) an intervening sequence; and
(d) a sequence comprising a reverse-complement of the DNA sequence of (b), wherein elements (a)-(d) are positioned in relation to each other such that expression of the expression cassette in a cotton seed results in RNA interference-mediated reduction of-gossypol production in the cotton seed.

9. The expression cassette of claim 8, wherein the seed-specific promoter comprises an α-globulin B gene promoter.

10. The expression cassette of claim 8, wherein the intervening sequence comprises an intron.

11. A binary *Agrobacterium tumefaciens* vector for transforming a host cotton plant cell, wherein a T-DNA region of the vector comprises a seed-specific promoter operably linked to a DNA sequence encoding an intron-containing hairpin cassette comprising a DNA sequence comprising at least 20 consecutive nucleotides of SEQ ID NO:1 and the reverse-complement thereof wherein expression of the hairpin cassette in a cotton plant reduces the level of gossypol in the seed.

12. The binary *Agrobacterium tumefaciens* vector of claim 11, wherein the seed-specific promoter comprises an α-globulin B gene promoter.

13. The binary *Agrobacterium tumefaciens* vector of claim 12, wherein the α-globulin B gene promoter comprises SEQ ID NO: 10 or a functional fragment thereof.

14. The binary *Agrobacterium tumefaciens* vector of claim 11, wherein the T-DNA region comprises nucleotide sequences encoding:
(a) a cotton α-globulin B gene promoter;
(b) a first nucleotide sequence comprising at least 20 consecutive nucleotides of SEQ ID NO:1;
(c) an intervening sequence; and
(d) a second nucleotide sequence that comprises at least 20 consecutive nucleotides that can hybridize intramolecularly to (b).

15. The binary *Agrobacterium tumefaciens* vector of claim 14, wherein the T-DNA region further comprises a transcription terminator.

16. The binary *Agrobacterium tumefaciens* vector of claim 14, wherein the T-DNA region further comprises a selectable marker operably linked to a promoter that is active in a cotton cell.

17. The binary *Agrobacterium tumefaciens* vector of claim 11, wherein the T-DNA region comprises:
(i) a cotton α-globulin B gene promoter;
(ii) a first nucleotide sequence comprising at least 20 consecutive nucleotides of SEQ ID NO:1;
(iii) an intervening sequence;
(iv) a second nucleotide sequence that comprises at least 20 consecutive nucleotides that can hybridize intramolecularly to (ii); and
(v) an octopine synthase terminator, wherein elements (i)-(v) are operably linked.

18. The binary *Agrobacterium tumefaciens* vector of claim 16, wherein the T-DNA region further comprises:
(vi) a nopaline synthase promoter;
(vii) a neomycin phosphotransferase II coding sequence; and
(viii) a nopaline synthase terminator, wherein elements (vi)-(viii) are operably linked.

19. A transgenic cotton cell comprising the expression cassette of claim 8.

20. A transgenic cotton cell comprising the T-DNA of the binary *Agrobacterium tumefaciens* vector of claim 18.

21. A transgenic cotton plant produced by the method of claim 5, or the progeny thereof, wherein the transgenic cotton plant or progeny thereof comprises the expression construct.

22. Transgenic seed from the plant of claim 21, comprising the expression construct.

23. A transgenic cotton plant comprising the expression cassette of claim 8.

24. A seed from the plant of claim 23, comprising the expression cassette.

25. A kit comprising the expression cassette of claim 8 or the binary *Agrobacterium tumefaciens* vector of claim 11 and at least one reagent for introducing the expression cassette or the binary *Agrobacterium tumefaciens* vector into a plant cell.

26. The kit of claim 25, further comprising instructions for introducing the expression cassette or the binary *Agrobacterium tumefaciens* vector into a plant cell.

27. The binary *Agrobacterium tumefaciens* vector of claim 15, wherein the transcription terminator is selected from the group consisting of an octopine synthase terminator and a nopaline synthase terminator.

* * * * *

UNITED STATES PATENT AND TRADEMARK OFFICE
CERTIFICATE OF CORRECTION

| | | |
|---|---|---|
| PATENT NO. | : 8,987,554 B2 | Page 1 of 1 |
| APPLICATION NO. | : 13/109682 | |
| DATED | : March 24, 2015 | |
| INVENTOR(S) | : Keerti S. Rathore et al. | |

It is certified that error appears in the above-identified patent and that said Letters Patent is hereby corrected as shown below:

On the Title Page, Item (63), please insert --Provisional application No. 60/773,893, filed Feb. 16, 2006--

Signed and Sealed this
Seventh Day of July, 2015

Michelle K. Lee
*Director of the United States Patent and Trademark Office*